US006538181B1

(12) United States Patent
Stalker et al.

(10) Patent No.: US 6,538,181 B1
(45) Date of Patent: *Mar. 25, 2003

(54) GLYCOGEN BIOSYNTHETIC ENZYMES IN PLANTS

(75) Inventors: David M. Stalker, Davis; Christine K. Shewmaker, Woodland; Janette V. Oakes, Davis, all of CA (US)

(73) Assignee: Calgene LLC, Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/384,361

(22) Filed: Aug. 26, 1999

Related U.S. Application Data

(60) Division of application No. 08/484,434, filed on Jun. 7, 1995, now Pat. No. 5,969,214, which is a continuation of application No. 08/016,881, filed on Feb. 11, 1993, now abandoned, which is a continuation-in-part of application No. 07/735,065, filed on Jul. 24, 1991, now Pat. No. 5,349,123, which is a continuation-in-part of application No. 07/731,226, filed on Jul. 16, 1991, now abandoned, which is a continuation-in-part of application No. 07/632,383, filed on Dec. 21, 1990, now abandoned, said application No. 08/016,881, is a continuation-in-part of application No. 07/536,392, filed on Jun. 11, 1990, now abandoned.

(51) Int. Cl.$^7$ .................. C12N 15/82; C12N 15/31; C12N 5/04; A01H 5/00; C12P 19/04
(52) U.S. Cl. .................. 800/284; 800/278; 800/288; 435/419; 536/23.2; 536/23.7
(58) Field of Search .................. 536/23.2, 23.6, 536/23.7, 24.1; 435/69.7, 69.8, 101, 194, 412, 419, 417, 468, 469; 800/278, 284, 287, 288, 294, 317.2, 320, 320.1, 320.2, 320.3

(56) References Cited

U.S. PATENT DOCUMENTS

| | | | | |
|---|---|---|---|---|
| 5,349,123 A | * | 9/1994 | Shewmaker et al. | 800/205 |
| 5,498,830 A | * | 3/1996 | Barry et al. | 800/205 |
| 5,969,214 A | * | 10/1999 | Stalker et al. | 800/205 |

OTHER PUBLICATIONS

Kumar et al. J. Biological Chemistry 261(34): 16256–16259, Dec. 1986.*
Willmitzer et al. Plant Polymeric Carbohydrates. pp. 33–39, Jan. 1993.*
Kossmann et al. Progress in Biotechnology 10: 271–278, Apr. 1995.*
Sweetlove et al. Biochem. J. 320: 493–498, 1996.*

* cited by examiner

Primary Examiner—David T. Fox

(57) ABSTRACT

The present invention is directed to the modification of reserve polysaccharides in plants. Specifically, it has been found that host plants can be successfully transformed with a nucleic acid sequence capable of expressing a chimeric reserve polysaccharide modification enzyme gene sequence which will synthesize novel reserve polysaccharides in plants or convert the transformed plant's endogenous starch reserves to novel starch degradation products.

7 Claims, 33 Drawing Sheets

GLGA-40

| | | | | | |
|---|---|---|---|---|---|
| GATCTAACAG | GAGCGATAAT | GCAGGTTTTA | CATGTATGTT | CAGAGATGTT | CCCGCTGCTT | 60 |
| AAAACCGGCG | GTCTGGCTGA | TGTTATTGGG | GCATTACCCG | CAGCACAAAT | CGCAGACGGC | 120 |
| GTTGACGCTC | GCGTACTGTT | GCCTGCATTT | CCCGATATTC | GCCGTGGGCGT | GACCGATGCG | 180 |
| CAGGTAGTAT | CCCGTCGTGA | TACCTTCGCC | GGACATATCA | CGCTGTGTGTT | CGGTCATTAC | 240 |
| AACGGGGTTG | GCATTTACCT | GATTGACGCG | CCGCATCTCT | ATGATCGTCC | GGGAAGCCCG | 300 |
| TATCACGATA | CCAACTTATT | TGCCTATACC | GACAACGTAT | TGCGTTTTGC | GCTGCTGGGG | 360 |
| TGGGTTGGGG | CAGAAATGGC | CAGCGGGGCTT | GACCCATTCT | GGCGTCCTGA | TGTGGTGCAT | 420 |
| GCGCACGACT | GGCATGCAGG | CCTTGCGCCT | GGGTATCTGG | CGGCGGCCGG | GCGTCCGGCG | 480 |
| AAGTCGGTGT | TTACTGGGCA | CAACCTGGCC | TATCAAGGCA | TGTTTTATGC | ACATCACATG | 540 |

FIG. 1A

```
AATGACATCC AATTGCCATG GTCATTCTTT AATATTCATG GGCTGGGAATT CAACGGACAA    600
ATCTCTTTCC TGAAGGCCGG TCTGTACTAT GCCGATCACA TTACGGGCGGT CAGTCCAACC    660
TACGCTCGCG AGATCACCGA ACCGCAGTTT GCCTACGGTA TGGAAGGTCT GTTGCAACAG    720
CGTCACCGTG AAGGGCGTCT TTCCGGGGTA CTGAACGGGCG TGGACGAGAA AATCTGGAGT    780
CCAGAGACGG ACTTACTGTT GGCCTCGCGT TACACCCCGCG ATACGTTGGA AGATAAAGCG    840
GAAAATAAGC GCCAGTTACA AATGCAATG GGGCTTAAGG TTGACGATAA AGTGCCGCTT    900
TTTGCAGTGG TGAGCCGTCT GACCAGCCAG AAAGGTCTCG ACCTGGTGCT GGAAGCCTTA    960
CCGGGTCTTC TGGAGCAGGG CGGGCAGCTG GCGCTACTCG GCGCGGGGCGA TCCGGTGCTG   1020
CAGGAAGGTT TCCTTGCGGC GGCAGCGGGAA TACCCCGGTC AGGTGGGCGT TCAGATTGGC   1080
```

FIG. 1B

```
TATCACGAAG CATTTTCGCA TCGCATTATG GGCGGCGCGG ACGTCATTCT GGTGCCCAGC 1140
CGTTTTGAAC CGTGCGGGCTT AACGCAACTT TATGGATTGA AGTACGGTAC GCTGCCGTTA 1200
GTGCGGCGCA CCGGTGGGCT TGCTGATACG GTTTCTGACT GTTCTCTTGA GAACCTTGCA 1260
GATGGCGTCC CCAGTGGGTT TGTCTTTGAA GATAGTAATG CCTGGTCGCT GTTACGGGCT 1320
ATTCGACGTG CTTTTGTACT GTGGTCCCGT CCTTCACTGT GGCGGTTTGT GCAACGTCAG 1380
GCTATGGCAA TGGATTTTAG CTGGCAGGTC GCGGCGAAGT CGTACCGTGA GCTTTACTAT 1440
CGCTCGAAAT AGTTTTCAGT CGAC                                        1464
```

FIG. 1C

GLGA-40

MET Gln Val Leu His Val Cys Ser Glu MET Phe Pro Leu Leu Lys Thr
 1               5                  10                  15

Gly Gly Leu Ala Asp Val Ile Gly Ala Leu Pro Ala Ala Gln Ile Ala
            20                  25                  30

Asp Gly Val Asp Ala Arg Val Leu Leu Pro Ala Phe Pro Asp Ile Arg
            35                  40                  45

Arg Gly Val Thr Asp Ala Gln Val Val Ser Arg Arg Asp Thr Phe Ala
            50                  55                  60

Gly His Ile Thr Leu Leu Phe Gly His Tyr Asn Gly Val Gly Ile Tyr
65                  70                  75                  80

Leu Ile Asp Ala Pro His Leu Tyr Asp Arg Pro Gly Ser Pro Tyr His
                85                  90                  95

Asp Thr Asn Leu Phe Ala Tyr Thr Asp Asn Val Leu Arg Phe Ala Leu
                100                 105                 110

FIG. 2 A

Leu Gly Trp Val Gly Ala Glu MET Ala Ser Gly Leu Asp Pro Phe Trp
115                 120                 125

Arg Pro Asp Val Val His Ala His Asp Trp His Ala Gly Leu Ala Pro
130                 135                 140

Ala Tyr Leu Ala Ala Arg Gly Arg Pro Ala Lys Ser Val Phe Thr Gly
145                 150                 155                 160

His Asn Leu Ala Tyr Gln Gly MET Phe Tyr Ala His His MET Asn Asp
165                 170                 175

Ile Gln Leu Pro Trp Ser Phe Phe Asn Ile His Gly Leu Glu Phe Asn
180                 185                 190

Gly Gln Ile Ser Phe Leu Lys Ala Gly Leu Tyr Tyr Ala Asp His Ile
195                 200                 205

Thr Ala Val Ser Pro Thr Tyr Ala Arg Glu Ile Thr Glu Pro Gln Phe
210                 215                 220

FIG. 2 B

Ala Tyr Gly MET Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
            245                 250                 255

Thr Asp Leu Leu Ala Ser Arg Tyr Thr Arg Asp Thr Leu Glu Asp
            260                 265                 270

Lys Ala Glu Asn Lys Arg Gln Leu Gln Ile Ala MET Gly Leu Lys Val
            275                 280                 285

Asp Asp Lys Val Pro Leu Phe Ala Val Val Ser Arg Leu Thr Ser Gln
290                 295                 300

Lys Gly Leu Asp Leu Val Leu Glu Ala Leu Pro Gly Leu Leu Glu Gln
305                 310                 315                 320

Gly Gly Gln Leu Ala Leu Leu Gly Ala Gly Asp Pro Val Leu Gln Glu
            325                 330                 335

FIG. 2 C

Gly Phe Leu Ala Ala Ala Glu Tyr Pro Gly Gln Val Gly Val Gln
340                     345                 350

Ile Gly Tyr His Glu Ala Phe Ser His Arg Ile MET Gly Gly Ala Asp
355                     360                 365

Val Ile Leu Val Pro Ser Arg Phe Glu Pro Cys Gly Leu Thr Gln Leu
370                     375                 380

Tyr Gly Leu Lys Tyr Gly Thr Leu Pro Leu Val Arg Arg Thr Gly Gly
385                     390                 395                 400

Leu Ala Asp Thr Val Ser Asp Cys Ser Leu Glu Asn Leu Ala Asp Gly
405                     410                 415

Val Ala Ser Gly Phe Val Phe Glu Asp Ser Asn Ala Trp Ser Leu Leu
420                     425                 430

Arg Ala Ile Arg Arg Ala Phe Val Leu Trp Ser Arg Pro Ser Leu Trp
435                     440                 445

FIG. 2 D

Arg Phe Val Gln Arg Gln Ala MET Ala MET Asp Phe Ser Trp Gln Val
450                     455                 460

Ala Ala Lys Ser Tyr Arg Glu Leu Tyr Tyr Arg Ser Lys
465                     470                 475

FIG. 2 E

```
GATCTAGGAG CGATA ATG GTT AGT TTA GAG AAG AAC GAT CAC TTA ATG         48
                MET Val Ser Leu Glu Lys Asn Asp His Leu MET
                 1                  5                      10

TTG GCG CGC CAG CTG CCA TTG AAA TCT GTT GCC CTG ATA CTG GCG GGA      96
Leu Ala Arg Gln Leu Pro Leu Lys Ser Val Ala Leu Ile Leu Ala Gly
            15                  20                  25

GGA CGT GGT ACC CGC CTG AAG GAT TTA ACC AAT AAG CGA GCA AAA CCG     144
Gly Arg Gly Thr Arg Leu Lys Asp Leu Thr Asn Lys Arg Ala Lys Pro
        30                  35                  40

GCC GTA CAC TTC GGC GGT AAG TTC CGC ATT ATC GAC TTT GCG CTG TCT     192
Ala Val His Phe Gly Gly Lys Phe Arg Ile Ile Asp Phe Ala Leu Ser
    45                  50                  55

AAC TGC ATC AAC TCC GGG ATC CGT CGT ATG GGC GTG ATC ACC CAG TAC     240
Asn Cys Ile Asn Ser Gly Ile Arg Arg MET Gly Val Ile Thr Gln Tyr
60                  65                  70                  75

CAG TCC CAC ACT CTG GTG CAG CAC ATT CAG CGC GGC TGG TCA TTC TTC     288
Gln Ser His Thr Leu Val Gln His Ile Gln Arg Gly Trp Ser Phe Phe
            80                  85                  90
```

FIG. 3A

```
AAT GAA GAA ATG AAC GAG TTT GTC GAT CTG CTG CCA GCA CAG CAG AGA    336
Asn Glu Glu MET Asn Glu Phe Val Asp Leu Leu Pro Ala Gln Gln Arg
         95                  100                 105

ATG AAA GGG GAA AAC TGG TAT CGC GGC ACC GCA GAT GCG GTC ACC CAA    384
MET Lys Gly Glu Asn Trp Tyr Arg Gly Thr Ala Asp Ala Val Thr Gln
        110                 115                 120

AAC CTC GAC ATT ATC CGC CGT TAT AAA GCG GAA TAC GTG GTG ATC CTG    432
Asn Leu Asp Ile Ile Arg Arg Tyr Lys Ala Glu Tyr Val Val Ile Leu
        125                 130                 135

GCG GGC GAC CAT ATC TAC AAG CAA GAC TAC TCG CGT ATG CTT ATC GAT    480
Ala Gly Asp His Ile Tyr Lys Gln Asp Tyr Ser Arg MET Leu Ile Asp
        140                 145                 150                 155

CAC GTC GAA AAA GGC GCA CGT TGC ACC GTT GCT TGT ATG CCA GTA CCG    528
His Val Glu Lys Gly Ala Arg Cys Thr Val Ala Cys MET Pro Val Pro
        160                 165                 170

ATT GAA GAA GCC TCC GCA TTT GGC GTT ATG GCG GTT GAT GAG AAC GAT    576
Ile Glu Glu Ala Ser Ala Phe Gly Val MET Ala Val Asp Glu Asn Asp
        175                 180                 185
```

FIG. 3B

```
AAA ATT ATC GAA TTC GTT GAA AAA CCT GCT AAC CCG CCG TCA ATG CCG    624
Lys Ile Ile Glu Phe Val Glu Lys Pro Ala Asn Pro Pro Ser MET Pro
        190                 195                 200

AAC GAT CCG AGC AAA TCT CTG GCG AGT ATG GGT ATC TAC GTC TTT GAC    672
Asn Asp Pro Ser Lys Ser Leu Ala Ser MET Gly Ile Tyr Val Phe Asp
        205                 210                 215

GCC GAT TAT CTG TAT GAA CTG CTG GAA GAC GAT CGC GAT GAG AAC        720
Ala Asp Tyr Leu Tyr Glu Leu Leu Glu Asp Asp Arg Asp Glu Asn
        220                 225                 230                235

TCC AGC CAC GAC TTT GGC AAA GAT TTG ATT CCC AAG ATC ACC GAA GCC    768
Ser Ser His Asp Phe Gly Lys Asp Leu Ile Pro Lys Ile Thr Glu Ala
        240                 245                 250

GGT CTG GCC TAT GCG CAC CCG TTC CCG CTC TCT TGC GTA CAA TCC GAC    816
Gly Leu Ala Tyr Ala His Pro Phe Pro Leu Ser Cys Val Gln Ser Asp
        255                 260                 265
```

FIG. 3C

```
CCG GAT GCC GAG CCG TAC TGG CGC GAT GTG GGT ACG CTG GAA GCT TAC    864
Pro Asp Ala Glu Pro Tyr Trp Arg Asp Val Gly Thr Leu Glu Ala Tyr
270                 275                 280

TGG AAA GCG AAC CTC GAT CTC GCC TCT GTG GTG CCG GAA CTG GAT ATG    912
Trp Lys Ala Asn Leu Asp Leu Ala Ser Val Val Pro Glu Leu Asp MET
        285                 290                 295

TAC GAT CGC AAT TGG CCA ATT CGC ACC TAC AAT GAA TCA TTA CCG CCA    960
Tyr Asp Arg Asn Trp Pro Ile Arg Thr Tyr Asn Glu Ser Leu Pro Pro
300                 305                 310                 315

GCG AAA TTC GTG CAG GAT CGC TCC GGT AGC CAC GGG ATG ACC CTT AAC    1008
Ala Lys Phe Val Gln Asp Arg Ser Gly Ser His Gly MET Thr Leu Asn
            320                 325                 330

TCA CTG GTT TCC GAC GGT TGT GTG ATC TCC GGT TCG GTG GTG CAG        1056
Ser Leu Val Ser Asp Gly Cys Val Ile Ser Gly Ser Val Val Gln
335                 340                 345

TCC GTT CTG TTC TCG CGC GTT CGC GTG AAT TCA TTC TGC GAC ATT GAT    1104
Ser Val Leu Phe Ser Arg Val Arg Val Asn Ser Phe Cys Asp Ile Asp
350                 355                 360
```

FIG. 3D

```
TCC GCC GTA TTG TTA CCG GAA GTA TGG GTA GGT CGC TCG TGC CGT CTG    1152
Ser Ala Val Leu Leu Pro Glu Val Trp Val Gly Arg Ser Cys Arg Leu
365                 370                 375

CGC CGC TGC GTC ATC GAT CGT GCT TGT GTT ATT CCG GAA GGC ATG GTG    1200
Arg Arg Cys Val Ile Asp Arg Ala Cys Val Ile Pro Glu Gly MET Val
    380                 385                 390                 395

ATT GGT GAA AAC GCA GAG GAA GAT GCA CGT CGT TTC TAT CGT TCA GAA    1248
Ile Gly Glu Asn Ala Glu Glu Asp Ala Arg Arg Phe Tyr Arg Ser Glu
            400                 405                 410

GAA GGC ATC GTG CTG GTA ACG CGC GAA ATG CTA CGG AAG TTA GGG CAT    1296
Glu Gly Ile Val Leu Val Thr Arg Glu MET Leu Arg Lys Leu Gly Ilis
        415                 420                 425

AAA CAG GAG CGA TAATGCAGGG TCGAC                                    1323
Lys Gln Glu Arg
430
```

FIG. 3E

```
     XbaI HindIII  EcoRV
       |    |        |
  1  TCTAGAAGCTTGGATATCTGGCAGCAGAAAAACAAGTAGTTGAGAACTAAG       51
     SerArgSerLeuAspIleTrpGlnGlnLysAsnLys . LeuArgThrLys
     LeuGluAlaTrpIleSerGlySerArgLysSerArgLysGlu . GluLeuAr
           LysLeuGlyTyrLeuAlaAlaGluLysGlnValValGluAsn . G
         2                                                        7                 16

PvuII
                                             NspBII
                                              |
 52  AAGAAGAAAATGGCTTCCTCAATGATCTCCTCCCCAGCTGTTACCACCGTC         102
     LysLysLysMETAlaSerSerMETIleSerSerProAlaValThrThrVal
     gArgArgLysTrpLeuProGln . SerProProGlnLeuLeuProProSer
     luGluGluAsnGlyPheLeuAsnAspLeuLeuProSerCysTyrHisArgG
                                                                    89
                                                                    89

StyI
                                                              NcoI
         NaeI                                                 DsaI
          |                                                    |
     HindII  HgiCI
       |     |
103  AACCGTGCCGGTGCCGGCATGGTTGCTCCATTCACCGGCCTCAAATCCATG          153
     AsnArgAlaGlyAlaGlyMETValAlaProPheThrGlyLeuLysSerMET
     rThrValProValProAlaTrpLeuLeuHisSerProAlaSerAsnProTr
     lnProCysArgCysArgHisGlyCysSerIleHisArgProGlnIleHisG
        103         113                                             150
                                                                    150
                                                                    150
                              118

FIG. 4A
```

```
                                            BbvII                          NheI
                                              |                              |
154  GCTGGCTTCCCCACGAGGAAGACCAACAATGACATTACCTCCATTGCTAGC  204
     AlaGlyPheProThrArgLysThrAsnAsnAspIleThrSerIleAlaSer
     pLeuAlaSerProArgGlyArgProThrMETThrLeuProProLeuLeuAl
     lyTrpLeuProHisGluGluAspGlnGln . HisTyrLeuHisCys . G
                                179                       200

SphI
              BspMI      NspI                                 [MfeI]
              [AvaIII]    |                    HaeI             |
              |           |                     |               |
     Ksp632I
       |
205  AACGGTGGAAGAGTACAATGCATGCAGGTGTGGCCTCCAATTGGAAAGAAG  255
     AsnGlyGlyArgValGlnCysMETGlnValTrpProProIleGlyLysLys
     aThrValGluGluTyrAsnAlaCysArgCysGlyLeuGlnLeuGluArgAr
     lnArgTrpLysSerThrMETHisAlaGlyValAlaSerAsnTrpLysGluG
              208          220    222      229   238     242
                                           229

XhoI
              BamHI
                |
256  AAGTTTGAGACTCTTTCCTGGGATCC  281
     LysPheGluThrLeuSerTrpAsp
     gSerLeuArgLeuPheProGlyIle
     luVal . AspSerPheLeuGlySer
                         277
                         277
```

FIG. 4B

```
X          10         20         30         40         50         60         70
X          :          :          :          :          :          :          :
           CTCGAGATTTGTCAAATCAGGCTCAAAGATCGTTTTTCATATCGGAATGAGGATTTTATTTATTCTTTTA
           :          :          :          :          :          :          :
           ATTTGTCAAATCAGGCTCAAAGATCGTTTTTCATATCGGAATGAGGATTTTATTTATTCTTTTA
X          10         20         30         40         50         60

80         90        100        110        120        130        140
           :          :          :          :          :          :          :
           AAAATAAAGAGGTGTTGAGCTAAACAATTTCAAATCTCATCACACATATGGGGTCAGCCACAAAAATAAA
           :          :          :          :          :          :          :
           AAAATAAAGAGGTGTTGAGCTAAACAATTTCAAATCTCATCACACATATGGGGTCAGCCACAAAAATAAA
           70         80         90        100        110        120        130

150        160        170        180        190        200        210
           :          :          :          :          :          :          :
           GAACGGTTGGAACGGATCTATTATATATAATAATACTAATAATAAAGAATAGAAAAAGGAAAGTGAGTGAGGTGCGAG
           :          :          :          :          :          :          :
           GAACGGTTGGAACGGATCTATTATATATAATAATACTAATAATAAAGAATAGAAAAAGGAAAGTGAGTGAGGTGCGAG
          140        150        160        170        180        190        200

220        230        240        250        260        270        280
           :          :          :          :          :          :          :
           GGAGAGAATCTGTTTACTATCAGAGTCGATCATGTGTCAGTTTTATCGATATGACTCTGACTTCAACTGA
           :          :          :          :          :          :          :
           GGAGAGAATCTGTTTACTATCAGAGTCGATCATGTGTCAGTTTTATCGATATGACTCTGATTTCAACTGA
          210        220        230        240        250        260        270

290        300        310        320        330        340
           :          :          :          :          :          :
           GTTTAAGCAATTCTGATAAGGCGAGGAAAATCACAGTGCTGAA-TCTAGAAAAATCTCATAGTGTGAGAT
           :          :          :          :          :          :
           GTTTAAGCAATTCTGATAAGGCGAGGAAAATCACAGTGCTGAAATCTAGAAAAATCTCATAGTGTGAGAT
          280        290        300        310        320        330        340
```

FIG. 5A

```
                  360       370       380       390       400       410
                   :....:....:....:....:....:....:....:....:....:....:....:....:
        AAGTCTCAACAAAAACGTTGAGTCCATAGAGGGGGGTGTATGTGACACCCCAACCTTCAGCAAAAGAAAACC
        ::::::::::::::::::::::::::::::::::::::::::::::::::::::::::::::::::::::::
        AAGTCTCAACAAAAACGTTGAGTCCATAGAGGGGGGTGTATGTGACACCCCAACCTTCAGCAAAAGAAAACC
                  350       360       370       380       390       400       410

430       440       450       460       470       480
                   :....:....:....:....:....:....:....:....:....:....:....:....:
        TCCCCTCAAGAAGGACATTTGCGGTGCTAAACAATTTCAAGTCTCATCACACATATATATTATATAATAC
        ::::::::::::::::::::::::::::::::::::::::::::::::::::::::::::::::::::::::
        TCCCCTCAAGAAGGACATTTGCGGTGCTAAACAATTTCAAGTCTCATCACACATATATATTATATAATAC
                  420       430       440       450       460       470       480

500       510       520       530       540       550
                   :....:....:....:....:....:....:....:....:....:....:....:....:
        TAATAAAGAATAGAAAAAGGAAAGGTAAACATCACTAATGACAGTTGCGGTGCAAAGTGAGTGAGATAAT
        ::::::::::::::::::::::::::::::::::::::::::::::::::::::::::::::::::::::::
        TAATAAAGAATAGAAAAAGGAAAGGTAAACATCACTAATGACAGTTGCGGTGCAAAGTGAGTGAGATAAT
                  490       500       510       520       530       540       550

570       580       590       600       610       620
                   :....:....:....:....:....:....:....:....:....:....:....:....:
        AAACATCAGTAATAGACATCACTAACTTTTTATTGGTTTATGTCAAACTCAAAATAAAATTTCTCAACTTGT
        ::::::::::::::::::::::::::::::::::::::::::::::::::::::::::::::::::::::::
        AAACATCAGTAATAGACATCACTAACTTTTTATTGGTTTATGTCAAACTCAAAATAAAATTTCTCAACTTGT
                  560       570       580       590       600       610       620
```

FIG. 5B

```
          640        650        660        670        680        690
TTACGTGCCTATATATACCATGCTTGTTATATGCTCAAAGCACCAACAAAATTTAAAAACAATTTGAACA
: : : : : : : : : : : : : : : : : : : : : : : : : : : : : : : : : : : : : : : : : : : : : : : : : : : : : : : : : : : : : : : : : : : :
TTACGTGCCTATATATACCATGCTTGTTATATGCTCAAAGCACCAACAAAATTTAAAAACAATTTGAACA
          630        640        650        660        670        680        690

710
TTTGCAAAACTAGTATGGG
: : : : : :
TTTGCAAAA
          700 X
```

FIG. 5C

```
X          10         20         30         40         50         60         70
   CTCGAGATTTGTCAAATCAGGCTCAAAGATCGTTTTTCATATCGGAATGAGGATTTTATTTATTCTTTTA
   :::::::::::::::::::::::::::::::::::::::::::::::::::::::::::::::::::::
   ATTTGTCAAATCAGGCTCAAAGATCGTTTTTCATATCGGAATGAGGATTTTATTTATTCTTTTA
X          10         20         30         40         50         60

80         90        100        110        120        130       140
   AAAATAAAGAGGTGGTGAGCTAAACAATTTCAAATCTCATCACACATATGGGGTCAGCCACAAAAATAAA
   :::::::::::::::::::::::::::::::::::::::::::::::::::::::::::::::::::::
   AAAATAAAGAGGTGTTGAGCTAAACAATTTCAAATCTCATCACACATATGGGGTCAGCCACAAAAATAAA
            70         80         90        100        110        120       130

150        160        170        180        190        200       210
   GAACGGTTGGAACGGATCTATTATATAATAATACTAATAATAAAGAATAGAAAAGGAAAAGTGAGTGAGGTGCGAG
   :::::::::::::::::::::::::::::::::::::::::::::::::::::::::::::::::::::
   GAACGGTTGGAACGGATCTATTATATAATAATACTAATAATAAAGAATAGAAAAGGAAAAGTGAGTGAGGTGCGAG
           140        150        160        170        180        190       200

220        230        240        250        260        270       280
   GGAGAGAATTTGTTTAATATCAGAGTCGATCATGTGTCAGTTTTATCGATATGATTCTGACTTCAACTGA
   :::::::::::::::::::::::::::::::::::::::::::::::::::::::::::::::::::::
   GGAGAGAATCTGTTTACTACTAGAGTCGATCATGTGTCAGTTTTATCGATATGACTCTGATTTCAACTGA
           210        220        230        240        250        260       270

FIG. 6A
```

```
              290       300       310       320       330       340
              |         |         |         |         |         |
GTTTAAGCAATTCTGATAAGGCGGAGAAAATCATAGTGCTGAG--TCTAGAAAATCTCATGCAGTGTGAG
:::::::::::::::::::::::::::::::::::::: ::::: :::::::::::::: :::::
GTTTAAGCAATTCTGATAAGGCGGAGAAAATCACACAGTGCTGAAATCTAGAAAATCTCAT--AGTGTGAG
              280       290       300       310       320       330       340

360
                 |
ATAAACCTCAACAAGAAC-------------------------------------------------
:::::  ::::::::::  :::
ATAAGTCTCAACAAAAACGTTGAGTCCATAGAGGGGTGTATGTGACACCCCAACCTCAGCAAAGAAAA
              350       360       370       380       390       400       410

370       380       390       400       410
                                     |         |         |         |         |
-----------------------------------ATTTGCGGTGCTAAACAATTTCAAGTCTTATCACACATATATTATATATT
                                    ::::::::::::::::::::::::::::::::::::::::::::::
CCTCCCCTCAAGAAGGACATTTGCGGTGCTAAACAATTTCAAGTCTCATCACACATATATTTATATAAT
              420       430       440       450       460       470       480

430       440       450       460       470       480
              |         |         |         |         |         |
ACTAATAAAGAATAGAAAAAGGAAAAGTAAACATCACTAATGACAGTTGCGGTGCAAAGTGAGTGAGATA
::::::::::::::::::::::::::::::::::::::::::::::::::::::::::::::::::
ACTAATAAAGAATAGAAAAAGGAAAAGTAAACATCACTAATGACAGTTGCGGTGCAAAGTGAGTGAGATA
              490       500       510       520       530       540       550
```

FIG. 6B

```
       500        510        520        530        540        550
ATAAACATCACTAATAGACATCACTAACTTTTTATTGGTTATGTCAAACTCAAAATAAAATTTCTCAACTT
:::::::::  ::::::::::::::::::::::::::::::::::::::::::::::::::::::::::
ATAAACATCAGTAATAGACATCACTAACTTTTTATTGGTTATGTCAAACTCAAAATAAAATTTCTCAACTT
       560        570        580        590        600        610        620

570        580        590        600        610        620
GTTTACGTGCCTATATATACCATGCTTGTTATATGCTCAAAGCACCAACAAAATTTAAAAACAATTTGAA
:::::::::::::::::::::::::::::::::::::::::::::::::::::::::::::::::::::
GTTTACGTGCCTATATATACCATGCTTGTTATATGCTCAAAGCACCAACAAAATTTAAAAACAATTTGAA
       630        640        650        660        670        680        690

640        650
CATTTGCAAAACTAGTATGGG
:::::::::::
CATTTGCAAAA
       700 X
```

FIG. 6C

```
         10         20         30         40         50         60
X  GGATCCATTAGGACTAGATAATGAAAAGAAACCGTTTTTTAATACCTCGGCTGCTATTG
   |||||||||||||||||||||||||||||||||||||||||||||||||||
   ATTAGGACTAGATAATGAAAAGAAACCGTTTTTTAATACCTCGGCTGCTATTG
X          10         20         30         40         50

70         80         90        100        110        120
   CCATTTCGATTGCATTAAATACTTTTTTTGTAGCATGCAGACGATTGCTGCTGAACCAG
   ||||||||||||||||||||||||||||||||||||||||||||||||||||||
   CCATTTCGATTGCATTAAATACTTTTTTTGTAGCATGCAGACGATTGCTGCTGAACCAG
           60         70         80         90        100        110

130        140        150        160        170        180
   AAGAAACTTATCTTGATTTTCGTAAGGAGACGATATATTTTCTATTCCTTGATCGTTTCA
   ||||||||||||||||||||||||||||||||||||||||||||||||||||||||||
   AAGAAACTTATCTTGATTTTCGTAAGGAGACGATATATTTTCTATTCCTTGATCGTTTCA
          120        130        140        150        160        170

190        200        210        220        230        240
   GCGATGGAGATCCAAGTAATAATGCAGGTTTAATTCTGCAACCTACGATCCTAATAATT
   ||||||||||||||||||||||||||||||||||||||||||||||||||||||||
   GCGATGGAGATCCAAGTAATAATGCAGGTTTAATTCTGCAACCTACGATCCTAATAATT
          180        190        200        210        220        230
```

FIG. 7A

```
       250         260         270         280         290         300
TAAAAAATATACTGGAGGAGATCTCCGGGGTTGATTAATAAACTACCCTATTTAAAAT
|||||||||||||||||||||||||||||||||||||||||||||||||||||||||
TAAAAAATATACTGGAGGAGATCTCCGGGGTTGATTAATAAACTACCCTATTTAAAAT
       240         250         260         270         280         290

310         320         330         340         350         360
CACTTGGTGTTACTTCAATCTGGATTACTCCCCCAATCGATAATGTGAATAATACTGATG
|||||||||||||||||||||||||||||||||||||||||||||||||||||||||||
CACTTGGTGTTACTTCAATCTGGATTACTCCCCCAATCGATAATGTGAATAATACTGATG
       300         310         320         330         340         350

370         380         390         400         410         420
CTGCTGGCAATACTGGATATCATGGTTATTGGGGAAGAGATTATTTTCGTATAGATGAAC
|||||||||||||||||||||||||||||||||||||||||||||||||||||||||||
CTGCTGGCAATACTGGATATCATGGTTATTGGGGAAGAGATTATTTTCGTATAGATGAAC
       360         370         380         390         400         410

430         440         450         460         470         480
ATTTTGGCAATCTCGATGATTTCAAAGAACTGACTAGTTTGATGCATAGTCCTGATTATA
|||||||||||||||||||||||||||||||||||||||||||||||||||||||||||
ATTTTGGCAATCTCGATGATTTCAAAGAACTGACTAGTTTGATGCATAGTCCTGATTATA
       420         430         440         450         460         470
```

FIG. 7B

```
      490       500       510       520       530       540
ATATGAAACTGGTTCTTGATTATGCCCCTAATCATTCGAATGCTAATGATGAAAATGAAT
|||||||||||||||||||||||||||||||||||||||||||||||||||||||||||
ATATGAAACTGGTTCTTGATTATGCCCCTAATCATTCGAATGCTAATGATGAAAATGAAT
      480       490       500       510       520       530

550       560       570       580       590       600
TTGGTGCACTATATCGTGATGGTGTGTTTATTACTGATGATTATCCTACAGATGTTGCCGCCA
|||||||||||||||||||||||||||||||||||||||||||| |||||||||||||||
TTGGTGCACTATATCGTGATGGTGTGTTTATTACTGATGATTATCCTACGAATGTTGCCGCCA
      540       550       560       570       580       590

610       620       630       640       650       660
ATACGGGCTGGTATCATCACAATGGTGGGGTAACGAACTGGAATGATTTCTTCCAAGTGA
|||||||||||||||||||||||||||||||||||||||||||||||||||||||||||
ATACGGGCTGGTATCATCACAATGGTGGGGTAACGAACTGGAATGATTTCTTCCAAGTGA
      600       610       620       630       640       650

670       680       690       700       710       720
AGAATCATAATCTATTCAATCTATCAGACCTCAATCAATCCAATACTGATGTCTACCAGT
|||||||||||||||||||||||||||||||||||||||||||||||||||||||||||
AGAATCATAATCTATTCAATCTATCAGACCTCAATCAATCCAATACTGATGTCTACCAGT
      660       670       680       690       700       710
```

FIG. 7C

```
             730        740        750        760        770        780
       ACTTGTTGGATGGCTTCTAAATTTTGGATCGATGCTGGTGTGTGGATGCTATCAGGATTGATG
       ||||||||||||||||||||||||||||||||||||||||||||||||||||||||||||||||
       ACTTGTTGGATGGTTCTAAATTTTGGATCGATGCTGGTGTGTGGATGCTATCAGGATTGATG
             720        730        740        750        760        770

790        800        810        820        830        840
       CCATCAAGCATATGGACAAGTCTTTTATACAGAAATGGACCAGCGGATATTTATGATTACA
       ||||||||||||||||||||||||||||||||||||||||||||||||||||||||||||||||
       CCATCAAGCATATGGACAAGTCTTTTTATACAGAAATGGACCAGCGGATATTTATGATTACA
             780        790        800        810        820        830

850        860        870        880        890        900
       GTAAGTCTATCGGCCGGGAAGGATTTTTTCTTCGGTGAATGGTTTGGTGCCAGTGCCGA
       ||||||||||||||||||||||||||||||||||||||||||||||||||||||||||||||||
       GTAAGTCTATCGGCCGGGAAGGATTTTTTTTCTTCGGTGAATGGTTTGGTGCCAGTGCCGA
             840        850        860        870        880        890

910        920        930        940        950        960
       ATACTACAACAGGTGTTGATGGTAATGCTATCGATTACGCCAACACTTCCGGGTCAGCGT
       ||||||||||||||||||||||||||||||||||||||||||||||||||||||||||||||||
       ATACTACAACAGGTGTTGATGGTAATGCTATCGATTACGCCAACACTTCCGGGTCAGCGT
             900        910        920        930        940        950
```

FIG. 7D

```
TGCTGGATTTTTGGATTCCGCGATACTTTAGAAAGAGTTTTTGGTAGGACGTAGCGGAAATA
       | | | | | | | | | | | | | | | | | | | | | | | | | | | | | | | | | | | | | | | | | | | | | | | | | | | | | | | | | | | | |
TGCTGGATTTTTGGATTCCGCGATACTTTAGAAAGAGTTTTTGGTAGGACGTAGCGGAAATA
    960       970       980       990       1000      1010
              970       980       990       1000      1010      1020

CAATGAAAAACGTTAAATAGTTTATCTGATAAAAAGACAAACAGTCTTTTACCAGTGATGACT
       | | | | | | | | | | | | | | | | | | | | | | | | | | | | | | | | | | | | | | | | | | | | | | | | | | | | | | | | | | | | |
CAATGAAAAACGTTAAATAGTTTATCTGATAAAAAGACAAACAGTCTTTTACCAGTGATGACT
    1020      1030      1040      1050      1060      1070
              1030      1040      1050      1060      1070      1080

GGCAGGTTGTTTTTATGGATAACCATGATATGGCACGCATTGGTACCGCTCTGCGTTCAA
       | | | | | | | | | | | | | | | | | | | | | | | | | | | | | | | | | | | | | | | | | | | | | | | | | | | | | | | | | | | | |
GGCAGGTTGTTTTTATGGATAACCATGATATGGCACGCATTGGTACCGCTCTGCGTTCAA
    1080      1090      1100      1110      1120      1130
              1090      1100      1110      1120      1130      1140

ACGCCACTACTTTTGGTCCTGGAAATAATGAAACCGGTGGAAGTCAGAGTGAAGCTTTTG
       | | | | | | | | | | | | | | | | | | | | | | | | | | | | | | | | | | | | | | | | | | | | | | | | | | | | | | | | | | | | |
ACGCCACTACTTTTGGTCCTGGAAATAATGAAACCGGTGGAAGTCAGAGTGAAGCTTTTG
    1140      1150      1160      1170      1180      1190
              1150      1160      1170      1180      1190      1200
```

FIG. 7E

```
         1210       1220       1230       1240       1250       1260
CTCAGAAACGTATAGACCTCGGTTGCTGGTTGCGACAATGACTGTACGTGGTATTCCTGCCA
|||||||||||||||||||||||||||||||||||||||||||||||||||||||||||||
CTCAGAAACGTATAGACCTCGGTTGCTGGTTGCGACAATGACTGTACGTGGTATTCCTGCCA
         1200       1210       1220       1230       1240       1250

1270       1280       1290       1300       1310       1320
TTTTATTATGGTACTGAACATTATGCCGCTAACTTTACCTCTAACAGTTTTGGTCAAGTTG
|||||||||||||||||||||||||||||||||||||||||||||||||||||||||||||
TTTTATTATGGTACTGAACATTATGCCGCTAACTTTACCTCTAACAGTTTTGGTCAAGTTG
         1260       1270       1280       1290       1300       1310

1330       1340       1350       1360       1370       1380
GCAGTGATCCTTACAACCGAGAGAAAATGCCAGGATTTGATACGGAAAGTGAGGCTTTCT
|||||||||||||||||||||||||||||||||||||||||||||||||||||||||||||
GCAGTGATCCTTACAACCGAGAGAAAATGCCAGGATTTGATACGGAAAGTGAGGCTTTCT
         1320       1330       1340       1350       1360       1370

1390       1400       1410       1420       1430       1440
CCATTATTAAAACACTGGGTGACCTAAGGAAAAGTAGCCCGGCAATTCAAAATGGAACTT
|||||||||||||||||||||||||||||||||||||||||||||||||||||||||||||
CCATTATTAAAACACTGGGTGACCTAAGGAAAAGTAGCCCGGCAATTCAAAATGGAACTT
         1380       1390       1400       1410       1420       1430
```

FIG. 7F

```
       1450       1460       1470       1480       1490       1500
ATACTGAACTATGGGTTAATGATGATATATTAGTATTTGAGCGGCGTTCTGGGAACGATA
   |||||||||||||||||||||||||||||||||||||||||||||||||||||||||||
ATACTGAACTATGGGTTAATGATGATATATTAGTATTTGAGCGGCGTTCTGGGAACGATA
       1440       1450       1460       1470       1480       1490

1510       1520       1530       1540       1550       1560
TTGTTATTGTTGCACTTAATCGTGGTGAGGCTAACACAATTAATGTTAAAAATATAGCGG
   |||||||||||||||||||||||||||||||||||||||||||||||||||||||||||
TTGTTATTGTTGCACTTAATCGTGGTGAGGCTAACACAATTAATGTTAAAAATATAGCGG
       1500       1510       1520       1530       1540       1550

1570       1580       1590       1600       1610       1620
TTCCTAATGGGGTATATCCGAGTTTGATTGGGAATAATAGTGTTTCAGTAGCAAATAAAC
   |||||||||||||||||||||||||||||||||||||||||||||||||||||||||||
TTCCTAATGGGGTATATCCGAGTTTGATTGGGAATAATAGTGTTTCAGTAGCAAATAAAC
       1560       1570       1580       1590       1600       1610

1630       1640       1650       1660       1670       1680
AGGCAACACTAACACTTATGCAAAATGAAGCTGTTGTCATTCGCTCACAATCAGATGATG
   | |||||||||||||||||||||||||||||||||||||||||||||||||||||||||
GGACAACACTAACACTTATGCAAAATGAAGCTGTTGTCATTCGCTCACAATCAGATGATG
       1620       1630       1640       1650       1660       1670
```

FIG. 7G

```
              1690        1700       1710       1720       1730       1740
     CGGAGAACCCTACAGTACAAAGCATAAACTTCGCATGTAATAACGGTTATACGATTTCAG
     ||||||||||||||||||||||||||||||||||||||||||||||||||||||||||||
     CGGAGAACCCTACAGTACAAAGCATAAACTTCACATGTAATAACGGTTATACGATTTCAG
              1680        1690       1700       1710       1720       1730

1750        1760       1770       1780       1790       1800
     GTCAAAGTGTTTATATTATTGGTAATATACCCTCAGTTAGGTGGTTGGGACTTAACTAAAG
     ||||||||||||||||||||||||||||||||||||||||||||||||||||||||||||
     GTCAAAGTGTTTATATTATTGGTAATATACCCTCAGTTAGGTGGTTGGGACTTAACTAAAG
              1740        1750       1760       1770       1780       1790

1810        1820       1830       1840       1850       1860
     CGGTAAAAATATCACCGACACAATATCCACAATGGAGTGCGAGCTTAGAGCTTCCTTCTG
     ||||||||||||||||||||||||||||||||||||||||||||||||||||||||||||
     CGGTAAAAATATCACCGACACAATATCCACAATGGAGTGCGAGCTTAGAGCTTCCTTCTG
              1800        1810       1820       1830       1840       1850

1870        1880       1890       1900       1910       1920
     ACTTAAATGTTGAATGGAAGTGTGTGAAACGTAATGAAACCAATCCGACGGCTAATGTTG
     ||||||||||||||||||||||||||||||||||||||||||||||||||||||||||||
     ACTTAAATGTTGAATGGAAGTGTGTGAAACGTAATGAAACCAATCCGACGGCTAATGTTG
              1860        1870       1880       1890       1900       1910
```

FIG. 7H

```
         1930       1940       1950       1960       1970       1980
AGTGGCAGTCTGGTGCAAATAACCAGTTCAATAGCAATGACACACAAACAACGAATGGCT
|||||||||||||||||||||||||||||||||||||||||||||||||||||||||||
AGTGGCAGTCTGGTGCAAATAACCAGTTCAATAGCAATGACACACAAACAACGAATGGCT
    1920       1930       1940       1950       1960       1970

1990        X
CGTTTTAATTAAAAGTCGAC
||||||||||||||||
CGTTTTAATTAAAA
    1980        X
```

FIG. 7I

```
X                                                           60
  MKRNRFFNTSAAIAISIALNTFFCSMQTIAAEPEETYLDFRKETIYFLFLDRFSDGDPSN
  |||||||||||||||||||||||||||||||||||||||||||||||||||||||||||
  MKRNRFFNTSAAIAISIALNTFFCSMQTIAAEPEETYLDFRKETIYFLFLDRFSDGDPSN
X                                                           60

120
  NAGFNSATYDPNNLKKYTGGDLRGLINKLPYLKSLGVTSIWITPPIDNVNNTDAAGNTGY
  |||||||||||||||||||||||||||||||||||||||||||||||||||||||||||
  NAGFNSATYDPNNLKKYTGGDLRGLINKLPYLKSLGVTSIWITPPIDNVNNTDAAGNTGY
                                                           120

180
  HGYWGRDYFRIDEHFGNLDDDFKELTSLMHSPDYNMKLVLDYAPNHSNANDENEFGALYRD
  |||||||||||||||||||||||||||||||||||||||||||||||||||||||||||
  HGYWGRDYFRIDEHFGNLDDDFKELTSLMHSPDYNMKLVLDYAPNHSNANDENEFGALYRD
                                                           180

240
  GVFITDYPTDVAANTGWYHHNGGVTNWNDFFQVKNHNLFNLSDLNQSNTDVYQYLLDGSK
  |||||  ||||| ||||||||||||||||||||||||||||||||||||||||||||||
  GVFITDYPTNVAANTGWYHHNGGVTNWNDFFQVKNHNLFNLSDLNQSNTDVYQYLLDGSK
                                                           240
```

FIG. 8A

```
              250          260          270          280          290          300
     FWIDAGVDAIRIDAIKHMDKSFIQKWTSDIYDYSKSIGREGFFFFGEWFGASANTTTGVD
     ||||||||||||||||||||||||||||||||||||||||||||||||||||||||||||
     FWIDAGVDAIRIDAIKHMDKSFIQKWTSDIYDYSKSIGREGFFFFGEWFGASANTTTGVD
              250          260          270          280          290          300

310          320          330          340          350          360
     GNAIDYANTSGSALLDFGFRDTLERVLVGRSGNTMKTLNSYLIKRQTVFTSDDWQVVFMD
     ||||||||||||||||||||||||||||||||||||||||||||||||||||||||||||
     GNAIDYANTSGSALLDFGFRDTLERVLVGRSGNTMKTLNSYLIKRQTVFTSDDWQVVFMD
              310          320          330          340          350          360

370          380          390          400          410          420
     NHDMARIGTALRSNATTFGPGNNETGGSQSEAFAQKRIDLGLVATMTVRGIPAIYYGTEH
     ||||||||||||||||||||||||||||||||||||||||||||||||||||||||||||
     NHDMARIGTALRSNATTFGPGNNETGGSQSEAFAQKRIDLGLVATMTVRGIPAIYYGTEH
              370          380          390          400          410          420

430          440          450          460          470          480
     YAANFTSNSFGQVGSDPYNREKMPGFDTESEAFSIIKTLGDLRKSSPAIQNGTYTELWVN
     ||||||||||||||||||||||||||||||||||||||||||||||||||||||||||||
     YAANFTSNSFGQVGSDPYNREKMPGFDTESEAFSIIKTLGDLRKSSPAIQNGTYTELWVN
              430          440          450          460          470          480
```

FIG. 8B

```
            490         500         510         520         530         540
     DDILVFERRSGNDIVIVALNRGEANTINVKNIAVPNGVYPSLIGNNSVSVANKQATLTLM
     ||||||||||||||||||||||||||||||||||||||||||||||||||||| |||||
     DDILVFERRSGNDIVIVALNRGEANTINVKNIAVPNGVYPSLIGNNSVSVANKRTTLTLM
            490         500         510         520         530         540

550         560         570         580         590         600
     QNEAVVIRSQSDDAENPTVQSINFACNNGYTISGQSVYIIGNIPQLGGWDLTKAVKISPT
     |||||||||||||||||||||||| |||||||||||||||||||||||||||||||||||
     QNEAVVIRSQSDDAENPTVQSINFTCNNGYTISGQSVYIIGNIPQLGGWDLTKAVKISPT
            550         560         570         580         590         600

610         620         630         640         650      X
     QYPQWSASLELPSDLNVEWKCVKRNETNPTANVEWQSGANNQFNSNDTQTTNGSF.
     |||||||||||||||||||||||||||||||||||||||||||||||||||||||
     QYPQWSASLELPSDLNVEWKCVKRNETNPTANVEWQSGANNQFNSNDTQTTNGSF.
            610         620         630         640         650      X
```

FIG. 8C

GLYCOGEN BIOSYNTHETIC ENZYMES IN PLANTS

RELATED APPLICATION DATA

This application is a divisional of application Ser. No. 08/484,434, filed Jun. 7, 1995, now U.S. Pat. No. 5,969,214, which is a continuation of application Ser. No. 08/016,881, filed Feb. 11, 1993, now abandoned, which is a continuation-in-part of application Ser. No. 07/735,065, filed Jul. 24, 1991, now U.S. Pat. No. 5,349,123, which is a continuation-in-part of application Ser. No. 07/731,226 filed Jul. 16, 1991, now abandoned, which is a continuation-in-part of application Ser. No. 07/632,383, filed Dec. 21, 1990, now abandoned. application Ser. No. 08/016,881 is also a continuation-in-part of application Ser. No. 07/536,392, filed Jun. 11, 1990, now abandoned.

TECHNICAL FIELD

This invention relates to transgenic plants and, more particularly, to methods and compositions which modify the biosynthesis and degradation pathways of reserve polysaccharides in plants.

BACKGROUND OF THE INVENTION

In the animal kingdom, nonvascular plants, fungi, yeast and bacteria, the primary reserve polysaccharide is glycogen. Glycogen is a D-glucose polysaccharide containing linear molecules with $\alpha$-1,4 glycosyl linkages and is branched via $\alpha$-1,6 glycosyl linkages. Although glycogen is analogous to starch from a linkage comparison, glycogen exhibits a different chain length and degree of polymerization. In bacteria, for example, the $\alpha$-1,6 glycosyl linkages constitute only approximately 10% of the total linkages, indicating that the majority of the glycogen polymer resides as linear glucose units.

In vascular plants, reserve polysaccharides are stored in roots, tubers and seeds in the form of starch. Starch, a complex polymer of D-glucose, consists of a mixture of linear chain (amylose) and branched chain (amylopectin) glucans. Starches isolated from different plants are found to have distinct proportions of amylose. Typically, amylose comprises from about 10–25% of plant starch, the remainder being the branched polymer amylopectin. Amylopectin contains low molecular weight chains and high molecular weight chains, with the low molecular weight chains ranging from 5–30 glucose units and the high molecular weight chains from 30–100 or more. The ratio of amylose/amylopectin and the distribution of low molecular weight to high molecular weight chains in the amylopectin fraction are known to affect the properties, such as thermal stabilization, retrogradation, and viscosity, and therefore the utility of starch. The highest published low m.w./high m.w. chain ratios (on a weight basis) in amylopectin are 3.9/1 for waxy corn starch, which has unique properties. Additionally, duwx, which has slightly more branch points than waxy, also has further unique properties.

In addition, starches from different plants or plant parts often have different properties. For example, potato starch has different properties than other starches, some of which may be due to the presence of phosphate groups. In some plant species, mutants have been identified which have altered contents of amylose and amylopectin. Mutations that affect the activity of starch-branching enzyme in peas, for example, result in seeds having less starch and a lower proportion of amylopectin. Also, mutations in the waxy locus of maize, which encodes a starch granule bound starch synthase, result in plants which produce amylopectin exclusively. Similarly, a potato mutant has been identified whose starch is amylose-free (Hovenkamp-Hermelink et al. *Theor. Appl. Genet.* (1987) 75:217–221). It has been found that varying the degree of starch branching can confer desirable physical properties; other changes in the characteristics of native starch could result in the production of polymers with new applications.

Cyclodextrins are the products of enzymatic starch degradation by a class of amylases termed cyclodextrin glycosyltransferase (CGT) enzymes. The family of cyclodextrins contains three major and several minor cyclic oligosaccharides which are composed of a number of homogenous cyclic $\alpha$-1,4-linked glucopyranose units. The cyclodextrin having six glucopyranose units is termed $\alpha$-cyclodextrin (also know as Schardinger's $\alpha$-dextrin, cyclomaltohexaose, cyclohexaglucan, cyclohexaamylose, $\alpha$-CD, ACD and C6A). The seven unit cyclodextrin is termed $\beta$-cyclodextrin (also known as Schardinger's $\beta$-dextrin, cyclomaltoheptaose, cycloheptaglucan, $\beta$-CD, BCD and C7A). The eight unit cyclodextrin is termed $\gamma$-cyclodextrin (also known as Schardinger's $\gamma$-dextrin, cyclomaltooctaose, cyclooctaglucan, cyclooctaamylose, $\gamma$-CD, GCD and C8A).

The cyclic nature of cyclodextrins allows them to function as clathrates (inclusion complexes) in which a guest molecule is enclosed in the hydrophobic cavity of the cyclodextrin host without resort to primary valence forces. Thus, the components are bound as a consequence of geometric factors, and the presence of one component does not significantly affect the structure of the other component. Complexing a hydrophobic compound with cyclodextrin increases the stability and solubility of the hydrophobic compound. Applications of this phenomena have been found in many fields including pharmaceuticals, foods cosmetics and pesticides.

In pharmaceutical applications, complexing a drug with cyclodextrins for oral delivery can have many advantages. Among the benefits are the transformation of liquids into solids which can be formed into tablets, stabilization of drugs against volatilization and oxidation, reduction of bad taste or smell, improvement in the rate of dissolution of poorly soluble drugs and increases in blood levels of poorly water soluble drugs (Pitha, in *Controlled Drug Delivery*, Bruck, ed. Vol. 1, p. 125, (1983) CRC Press). From the limited research done on parenteral administration of cyclodextrin-complexed drugs, some of the same advantages found for oral delivery can also be observed. The undesirable side effects of drugs can be reduced with complexation with cyclodextrins. Such side affects include gastric irritation from oral delivery, local irritation and hemorrhagic areas from intramuscular injection, and local irritation from eye-drops (Szejtli, J., *Cyclodextrin Technology*, Kluwer Academic Publications, Boston (1988), pp. 186–306).

The addition of cyclodextrins to food products or cosmetics can also have many effects. In spices, food flavoring or perfume fragrances, cyclodextrins protect against oxidation, volatility, and degradation by heat or light (Hashimoto, H., "Application of Cyclodextrins to Food, Toiletries and Other Products in Japan," in *Proceedings of the Fourth International Symposium of Cyclodextrins*, O. Huber and J. Szejtli, eds. (1988) pp. 533–543). Cyclodextrins can also eliminate or reduce undesirable smells or tastes, and modify food or cosmetic textures.

Complexing pesticides with cyclodextrins can increase the bioavailability of poorly wettable or slightly soluble substances, and transform volatile liquids or sublimable solids into stable solid powders (Szejtli, J. (1988) supra at pp. 335–364; U.S. Pat. No. 4,923,853). Pesticides which are sensitive to light, heat or oxygen degradation can be stabilized by complexing with cyclodextrins.

Currently, production of cyclodextrins begins with the cultivation of an appropriate microorganism, e.g., *Bacillus macerans*, and separation, purification and concentration of the amylase enzyme. The enzyme is then used to convert a starch substrate to a mixture of cyclic and acyclic dextrins. Subsequent separation and purification of cyclodextrins is then required. The bacterial strain from which the enzyme is isolated and the length of time the starch conversion is allowed to progress determines the predominant form of cyclodextrin produced. Manufactures of α-cyclodextrins attempt to manipulate the reaction to preferentially make the specific cyclodextrin, however, the process is not easily controlled, and a mixture of cyclodextrins is obtained. At the present time β-cyclodextrin is the most widely commercialized form of cyclodextrin because the β-form is much cheaper to produce than the α- or γ-cyclodextrins.

In 1987, the U.S. market for cyclodextrins was predicted to reach $50 million per year within 2 years; that figure would double if the U.S. Food and Drug Administration approved the use of cyclodextrins in food (Seltzer, R., *Chem. Eng. News*, (May 1987) pp. 24–25). The world market is estimated to be twice the U.S. figure (Szejtli, J. (1988) supra at p. viii). The potential U.S. market for cyclodextrins has been predicted to reach as high as $245 million per year (Anon., Bioproc. Technol., November 1987). There is potentially a large market waiting to be tapped if the cost of cyclodextrins could be lowered through alternative production methods.

With the development of genetic engineering techniques, it is now possible to transfer genes from a variety of organism into the genome of a large number of different plant species. This process is preferable to plant breeding techniques whereby genes can only be transferred from one plant in a species to another plant in the same or a closely related species. It would thus be desirable to develop plant varieties through genetic engineering, which have increased capacity for starch synthesis, altered amylose/amylopectin ratios, altered distribution of low to high molecular weight chains in the amylopectin fraction and also starches with novel molecular weight characteristics. In this manner, useful starches with a variety of viscosity or texture differences may be obtained.

In addition, recognizing the disadvantages of bacterial-derived CGT-mediated cyclodextrin production, it is considered desirable to produce cyclodextrins where CGT is the expression product of a recombinant gene transferred into a plant host. In this method, generically known as molecular farming, plants are transformed with a structural gene of interest and the product extracted and purified from a harvested field of the transgenic plants. For example, human serum albumin has been produced in transgenic tobacco and potato (Sijmons, P.C. et al., *Bio/Technology* (1990) 8:217–221).

Extending the idea of molecular farming to cyclodextrins provides a means to lower production costs. One particularly desirable host plant for such transformation is potato because of the large amount of starch production in potato tubers. A typical tuber contains approximately 16% of its fresh weight as starch (Burton, W. G., *The Potato* (1966) 3rd Edition, Longman Scientific and Technical Publications, England, p. 361). Transformation of potato plants with the bacterial CGT structural gene linked to a tuber-specific promoter and a leader directing the enzyme, for example, to the amyloplast, provides a means to produce large quantities of clodextrins in tubers.

To this end, nucleic acid sequences which encode glycogen biosynthetic or degradative enzymes are desirable for study and manipulation of the starch biosynthetic pathway. In particular, these enzymes may be expressed in plant cells using plant genetic engineering techniques and targeted to a plastid where starch synthesis occurs. It was therefore considered desirable to apply recombinant deoxyribonucleic acid (rDNA) and related technologies to provide for modified reserve polysaccharides in transgenic plants.

Proceeding from the seminal work of Cohen & Boyer, U.S. Pat. No. 4,237,224, rDNA technology has become available to provide novel DNA sequences and to produce heterologous proteins in transformed cell cultures. In general, the joining of DNA from different organisms relies on the excision of DNA sequences using restriction endonucleases. These enzymes are used to cut donor DNA at very specific locations, resulting in gene fragments which contain the DNA sequences of interest. Alternatively, structural genes coding for desired peptides and regulatory control sequences of interest can now be produced synthetically to form such DNA fragments.

These DNA fragments usually contain short single-stranded tails at each end, termed "sticky-ends". These sticky-ended fragments can then be ligated to complementary fragments in expression vehicles which have been prepared, e.g., by digestion with the same restriction endonucleases. Having created an expression vector which contains the structural gene of interest in proper orientation with the control elements, one can use this vector to transform host cells and express the desired gene product with the cellular machinery available. Recombinant DNA technology provides the opportunity for modifying plants to allow the expression of desirable enzymes in planta.

However, while the general methods are easy to summarize, the construction of an expression vector containing a desired structural gene is a difficult process and the successful expression of the desired gene product in significant amounts while retaining its biological activity is not readily predictable. Frequently, bacterial-derived gene products are not biologically active when expressed in plant systems.

To successfully modify plants using rDNA, one must usually modify the naturally occurring plant cell in a manner in which the cell can be used to generate a plant which retains the modification. Even in successful cases, it is often essential that the modification be subject to regulation. That is, it is desirable that the particular gene be regulated as to the differentiation of the cells and maturation of the plant tissue. In the case of glycogen synthase, ADP-glucose pyrophosphorylase and/or cyclodextrin glycosyltransferase, it is also important that the modification be performed at a site where the product will be directed to contact the reserve polysaccharide regions of the modified plant. Thus, genetic engineering of plants with rDNA presents substantially increased degrees of difficulty.

In addition, the need to regenerate plants from the modified cells greatly extends the period of time before one can establish the utility of the genetic construct. It is also important to establish that the particular constructs will be useful in a variety of different plant species. Furthermore, one may wish to localize the expression of the particular construct in specific sites and it is desirable that the genetically modified plant retain the modification through a number of generations.

Relevant Literature

The structural genes encoding the *E. coli* glycogen biosynthetic enzymes have been cloned (Okita, et al. (1981) *J. Biol. Chem.* 256:6944–6952) and their nucleic acid sequences determined (Preiss, J. (1984) *Ann. Rev. Microbiol.* 38:419–458; Kumar et al. (1986) *J. Biol. Chem.* 261:16256–16259). Genes encoding mammalian glycogen synthases have also been cloned and their nucleic acid sequences determined (Browner, et al. *Proc. Nat. Acad. Sci.* (1989) 86:1443–1447; Bai, et al., *J. Biol Chem.* (1990) 265:7843–7848).

DISCLOSURE OF THE INVENTION

By this invention, nucleic acid constructs comprising at least one chimeric reserve polysaccharide modification enzyme gene sequence and promoter and control sequences operable in plant cells, are provided.

In particular, one aspect of this invention relates to constructs comprising sequences relating to reserve polysaccharide biosynthetic enzymes, such as glycogen biosynthetic enzymes, glycogen synthase and/or ADP-glucose pyrophosphorylase. Another aspect of the invention relates to constructs comprising sequences relating to polysaccharide degradation enzymes, including amylases such as cyclodextrin glycosyltransferases.

In one aspect of the invention, a sequence encoding a desired enzyme is joined to a sequence which encodes a transit peptide that provides for translocation of the enzyme to a plastid.

Other constructs of this invention provide sequences for transcription of the selected enzyme sequences in plant cells. To this end, transcriptional initiation regions that function to regulate expression of genes in plants are considered. Of particular interest are those regulatory regions that preferentially direct expression of genes in roots, tubers, and seeds, or in other plant parts that synthesize reserve starch. In addition, constructs may contain sequences encoding a marker enzyme for selection of transformed cells.

Expression constructs which comprise sequences which provide for transcriptional and translational regulation in plant cells of the sequences encoding the desired enzymes are of special interest. These constructs include, in the 5'-3' direction of transcription, a transcriptional/translational initiation control region, a sequence encoding a selected enzyme in reading frame, and a transcription/translation termination region, wherein the sequence encoding the enzyme is under the regulatory control of the initiation and termination regions. Expression constructs may also contain sequences which encode a transit peptide that provides for translocation of the enzymes to plastids and/or a marker enzyme.

Another aspect of the invention involves vectors which comprise sequences providing for transfer of desired sequences and integration into the genome of a plant cell. For example plant transformation vectors may include Agrobacterium T-DNA border region(s) to provide for transfer of the sequences to the plant cell.

Also considered part of this invention are plant cells containing nucleic acid sequences of the desired enzyme. Such plant cells are obtainable through transformation techniques which utilize, e.g., Agrobacterium to transfer DNA to the plant cells or through direct transfer techniques such as DNA bombardment, electroporation or microinjection. Plant cells containing the desired sequences can be regenerated to yield whole plants containing the sequences.

In yet another aspect of this invention, plant cells containing the,desired enzymes or having reduced or increased starch precursor enzymes are considered. Of particular interest are plant cells in starch storage organs, such as roots, tubers or seeds. It is preferable that the enzyme be located in plastids, where starch synthesis occurs, and more preferably in amyloplasts, where reserve starch is synthesized and stored.

Further, it can be recognized that the modulation of polysaccharide modification enzymes in these plant cells has implications for modifying the starch content and/or composition of these cells. In this manner, plants or plant parts which synthesize and store starch may be obtained which have increased or decreased starch content and modified starch related properties such as specific gravity, free sugar content and/or novel and useful starches. In particular, potato starch having decreased amylose and modified amylopectin may be produced and further applications to modify starches consisting entirely of amylopectin such as that of waxy maize or a mutant potato, are also considered. Similarly, the starch from these plant parts can be harvested for use in commercial applications, or can be modified in planta to produce desired starch degradation products.

BRIEF DESCRIPTION OF THE DRAWINGS

FIGS. 1A–C depicts a DNA sequence (SEQ ID NO: 11) for the *E. coli* glycogen synthase gene, glgA, generated through Polymerase Chain Reaction (PCR) from *E. coli* K-12 618;

FIGS. 2A–E depicts the translated amino acid sequence (SEQ ID NO: 12) of the PCR generated glgA gene;

FIGS. 3A–E depicts DNA sequence (SEQ ID NO: 13) and the translated amino acid sequence (SEQ ID NO: 14) of the PCR generated *E. coli* ADP-glucose pyrophosphorylase gene, glgC, from *E. coli* K-12 618;

FIGS. 4A–B depicts the DNA sequence which encodes a SSU transit peptide from soybean plus 48 bp of DNA which encodes a mature SSU protein from pea, together with the amino acid sequence encoded by the reading frame (upper sequence); the DNA sequence of FIG. 4 and the translated amino acid sequences in three reading frames are represented as SEQ ID NO: 15–20.

FIGS. 5A–C depicts a comparison of DNA sequences from patatin 5' untranslated regions from *Solanum tuberosum* varieties *Kennebec* (top sequence, SEQ ID NO: 21) (generated by PCR) and Maris Piper (bottom sequence, SEQ ID NO: 2; );

FIGS. 6A–C depicts a comparison of DNA sequences from patatin 5' untranslated regions from *Solanum tuberosum* varieties *Russet Burbank* (top sequence, SEQ ID NO: 23) (generated by PCR) and *Maris Piper* (bottom sequence, SEQ ID NO: 24)

FIGS. 7A–I depicts a comparison of DNA sequences for native *Klebsiella pneumoneae* cyclodextrin glycosyltransferase (bottom sequence, SEQ ID NO: 25) and PCR generated pCGT2 cyclodextrin glycosyltransferase (top sequence, SEQ ID NO: 26) (absence of bar between bases indicates difference in the two sequences; and FIGS. 8A–C depicts a comparison of amino acid sequences for native *Klebsiella pneumoneae* cyclodextrin glycosyltransferase (bottom sequence, SEQ ID NO: 27) and pCGT2 cyclodextrin glycosyltranserase (top sequences, SEQ ID NO: 28) (absence of bar between residues indicates difference in the two sequences).

DETAILED DESCRIPTION OF THE INVENTION

The present invention relates to the expression of novel reserve polysaccharide modification enzyme gene sequences in plants. In particular, this invention is directed to a plant cell having nucleic acid sequences encoding such enzymes integrated in its genome as the result of genetic engineering. Cells containing a DNA or RNA (mRNA) sequence encoding the enzyme, as well as cells containing the enzyme, are also provided. Plants and, more particularly, plant parts may also be obtained which contain such enzyme gene sequences and/or such enzymes.

In considering the present reserve polysaccharide modification enzymes, there are two major classes presented: Biosynthetic enzymes which produce novel reserve polysaccharides, and starch degradation enzymes which produce novel starch degradation products. Representative of the first class of such enzymes include glycogen biosynthetic enzymes, which are not known to be endogenous to vascular plants.

The biosynthetic steps involved in glycogen synthesis in *E. coli* include: 1) the formation of ADP-glucose from ATP and glucose 1-phosphate, 2) the transfer of a glucose unit from ADP-glucose to a preformed maltodextrin primer via an $\alpha$-1,4 linkage, and 3) the formation of $\alpha$-1,6 glucosyl linkages from glycogen. The bacterial enzymes which catalyze the above reactions are ADP-glucose pyrophosphorylase (EC 2.7.7.27), glycogen synthase (EC 2.4.1.21), and Q-enzyme or branching enzyme (EC 2.4.1.18), respectively. The genes encoding these enzymes have been cloned and are also known as glgC, glgA, and glgB, respectively.

The pathway of glycogen biosynthesis in mammals is similar to that in bacteria, an exception being that UDP-glucose is the preferred glucose donor. The mammalian enzymes which catalyze glycogen biosynthetic reactions similar to those in bacteria are glucose-1-phosphate uridylyltransferase, glycogen synthase (EC 2.4.1.11), and 1,4-$\alpha$-glucan branching enzyme. Genes encoding human muscle and rat liver glycogen synthases have been cloned and their sequences determined.

In particular, the glycogen biosynthesis enzyme glycogen synthase (glgA) is of special interest. The *E. coli* glycogen synthase is of particular interest in that the enzyme is similar to plant starch synthase with respect to being non-responsive to allosteric effectors or chemical modifications. Expression of a glycogen synthase enzyme in a plant host demonstrates biological activity even within an intact plant cell. Namely, potato plants having glgA expressed in potato tubers result in tubers having a deceased specific gravity;. specific gravity being a commonly used measurement with respect to dry matter and starch contents of potato tubers (W. G,. Burton, in *The Potato*, Third Edition, pub. Longman Scientific & Technical (1989) Appendix II, pp. 599–601). Further analysis of transgenic tubers having decreased specific gravity indicates that the starch in these tubers is modified. In particular, the percentage of amylose is decreased and the ratio of low m.w./high m.w. chains in the amylopectin fraction is increased. This phenotypic effect in planta is indicative of glgA biological activity. Additional disclosure concerning glycogen biosynthetic enzymes can be found in U.S. patent application Ser. No. 07/735,065, filed on Jul. 16, 1991 and U.S. patent application Ser. No. 07/632,383, filed on Dec. 21, 1990, the complete specifications of which are incorporated herein by this reference.

Other phenotypic starch modifications resulting from biological activity of glycogen biosynthetic enzymes in plants are also considered in this invention. Such altered phenotypes may result from enzymatic activity of these proteins on plant starch precursors, or from the inhibition of plant starch biosynthetic enzyme activities. Inhibition of plant enzymes, for example, could result through the production of inactive forms of the plant enzymes as the result of association with the glycogen biosynthetic enzymes. The inhibition of plant enzymes may then lead to plants having altered starch (such as branching patterns or molecular weight) and/or lowered starch levels. In addition, increased plant metabolites, such as sugars, could also result from starch alteration or inhibition caused by expression of glycogen biosynthetic enzymes. For example, transgenic potato tubers described herein are observed to have up to 3-fold increases in free sugar content.

Measurement of specific gravity or free sugar content may be useful to detect modified starch, with other methods, such as HPLC and gel filtration, also being useful. The glycogen synthase sequence may be employed as the sole glycogen biosynthetic enzyme or in conjunction with sequences encoding other glycogen biosynthetic enzymes.

In accordance with an additional aspect of the subject invention, the second class of reserve polysaccharide modification enzymes includes novel starch degradation enzymes which permit modification of the composition of host plants to increase synthesis of starch degradation products. Representative of such enzymes are amylase enzymes such as cyclodextrin glycosyltransferase enzymes, which can provide for the production of cyclodextrins from endogenous starch reserves in a variety of host plants.

As used herein, cyclodextrin glycosyltransferase (CGT) is intended to include any equivalent amylase enzyme capable of degrading starch to one or more forms of cyclodextrin. Considerations for use of a specific CGT in plants for the conversion of starch to cyclodextrin include pH optimum of the enzyme and the availability of substrate and cofactors required by the enzyme. The CGT of interest should have kinetic parameters compatible with the biochemical systems found in the host plant cell. For example, the selected CGT may compete for starch substrate with other enzymes.

The most preferred cyclodextrin forms are the $\alpha$-, $\beta$- or $\gamma$-forms, although other higher forms of cyclodextrins, e.g. $\delta$-, $\epsilon$-, $\zeta$- and $\eta$-forms, are also possible. Different CGT enzymes produce $\alpha$, $\beta$, and $\gamma$ CDs in different ratios. See, Szejtli, J., *Cyclodextrin Technology* (Kluwer Academic Publications, Boston) (1988), pp. 26–33 and Schmid, G., *TIBTECH* (1989) 7:244–248. In addition, various CGT enzymes can preferentially degrade the starch substrate to favor production of a particular cyclodextrin form. Some CGTs produce primarily $\beta$-CDs (Bender, H (1990) *Carb. Res.* 206:257–267; Kimura et al. (1987) *Appl. Microbiol. Biotechnol.* 26:149–153), whereas the Klebsiella CGT described in the following examples, produces $\alpha$- and $\beta$-CDs in vitro at a ratio of 20:1 when potato starch is used as the substrate (Bender, H. (1990) supra). The use of these different CGTs in transgenic plants could result in different CD profiles and thus different utilities. For example, cyclodextrins have been reported as effective in inhibiting apple juice browning, with $\beta$-cyclodextrins producing better results than either $\alpha$- or $\gamma$-cyclodextrins (*Chemistry and Industry*, London (1988) 13:410). In addition, it has been discovered that in vitro application of $\beta$-CDs to potato tuber slices inhibits discoloration, and in vitro application to whole potato tubers prevents a typical blackspot reaction caused by bruising. Additional disclosure concerning cyclydextrin glycosyltransferase enzymes can be found in U.S. patent application Ser. No. 07/536,392, filed on Jun. 11, 1990, the complete specification of which is incorporated herein by this reference.

An enzyme relevant to the present invention as including any sequence of amino acids, such as protein, polypeptide, or peptide fragment, which demonstrates the ability to catalyze a reaction involved in the modification of the reserve polysaccharide content of a transformed host cell.

In one aspect of the invention, the modification will result in the biosynthesis of glycogen. Thus, a glycogen biosynthetic enzyme of this invention will display activity towards a glucan molecule, although it may have preferential activity towards either ADP- or UDP-glucose. In plants, ADP-glucose is the preferred donor for starch biosynthetic reactions. Therefore, of particular interest in this invention are glycogen biosynthesis enzymes which also prefer ADP-glucose. Of special interest are glycogen biosynthesis enzymes obtainable from bacterial sources. Over 40 species of bacteria synthesize glycogen, including Escherichia and Salmonella.

Obtaining glycogen biosynthetic enzymes may be accomplished by a variety of methods known to those skilled in the art. For example, radiolabeled nucleic acid probes may be prepared from a known sequence which will bind to, and thus provide for detection of, other sequences. Glycogen biosynthesis enzymes may be purified and their sequences obtained through biochemical or antibody techniques, polymerase chain reaction (PCR) may be employed based upon known nucleic acid sequences, and the like.

In another aspect of the invention, the modification will result in the production of novel starch degradation products such as, e.g., cyclodextrins. The structural gene for a selected CGT can be derived from cDNA, from chromosomal DNA or may be synthesized, either completely or in part. For example, the desired gene can be obtained by generating a genomic DNA library from a source for CGT, such as a prokaryotic source, e.g. *Bacillus macerans, Bacillus subtilis* or, preferably, from *Klebsiella pneumoneae*.

Typically, a gene sequence obtainable from the use of nucleic acid probes will show 60–70% sequence identity between the target sequence and the given sequence encoding an enzyme of interest. However, lengthy sequences with as little as 50–60% sequence identity may also be obtained. The nucleic acid probes may be a lengthy fragment of the nucleic acid sequence, or may also be a shorter, oligonucleotide probe. Oligonucleotide probes can be considerably shorter than the entire nucleic acid sequence encoding a selected enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Hybridization and washing conditions can be varied to optimize the hybridization of the probe to the sequences of interest. Lower temperatures and higher salt (SSC) concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe. (See, for example, Beltz, et al. *Methods in Enzymologay* (1983) 100:266–285).

It will be recognized by one of ordinary skill in the art that selected enzyme sequences of this invention may be modified using standard techniques of site specific mutation or PCR, or modification of the sequence may be accomplished in producing a synthetic nucleic acid sequence and will still be considered an enzyme nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of an enzyme relevant to the present invention may be a DNA or RNA sequence, derived from genomic DNA, cDNA, mRNA, or may be synthesized in whole or in part. The structural gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene may be synthesized using codons preferred by a selected plant host. Plant-preferred codons may be determined, for example, from the codons used most frequently in the proteins expressed in a particular plant host species. Other modifications of the gene sequences may result in mutants having slightly altered activity. Once obtained, an enzyme nucleic acid sequence of this invention may be combined with other sequences in a variety of ways.

Often, the sequences associated with reserve polysaccharide modification are used in conjunction with endogenous plant sequences. By "endogenous plant sequence" is meant any sequence which can be naturally found in a plant cell. These sequences include native (indigenous) plant sequences as well as sequences from plant viruses or plant pathogenic bacteria, such as Agrobacterium or Rhizobium species that are naturally found and functional in plant cells.

In one aspect of this invention, the selected enzyme sequence will be joined to a sequence encoding a transit peptide or functional portion of a transit peptide which is capable of providing for intracellular transport of a heterologous protein to a plastid in a plant host cell. Chloroplasts are the primary plastid in photosynthetic tissues, although plant cells are likely to have other kinds of plastids, including amyloplasts, chromoplasts, and leucoplasts. Transport into amyloplasts is preferred in this invention as these plastids are associated with reserve starch synthesis and storage. Any transit peptide providing for intracellular transport to a plastid is useful in this invention, such as the transit peptides from the precursor proteins of the small subunit of ribulose bisphosphate carboxylase (RUBISCO), acyl carrier protein (ACP), the waxy locus of maize, or other nuclear-encoded plastid proteins.

In addition to the identified transit peptide portion of a protein, it may be desirable to include sequences encoding a portion of the mature plastid-targeted protein to facilitate the desired intracellular transport of the glycogen biosynthetic enzyme. In one embodiment of this invention, the transit peptide from the small subunit of RUBISCO is utilized along with 48 bp of sequence encoding the amino terminal 16 amino acids of a mature small subunit protein.

Other endogenous plant sequences may be provided in nucleic acid constructs of this invention, for example to provide for transcription of the enzyme sequences. Transcriptional regulatory regions are located immediately 5' to the DNA sequences of the gene of interest, and may be obtained from sequences available in the literature, or identified and characterized by isolating genes having a desirable transcription pattern in plants, and studying the 5' nucleic acid sequences. Numerous transcription initiation regions which provide for a variety of constitutive or regulatable, e.g. inducible, expression in a plant cell are known. Among sequences known to be useful in providing for constitutive gene expression are regulatory regions associated with Agrobacterium genes, such as for nopaline synthase (Nos), mannopine synthase (Mas), or octopine synthase (Ocs), as well as regions coding for expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, patatin, zein, and the like.

Sequences to be transcribed are located 3' to the plant transcription initiation region and may be oriented, in the 5'-3' direction, in the sense orientation or the antisense orientation. In the sense orientation, an mRNA strand is produced which encodes the desired glycogen biosynthetic enzyme, while in antisense constructs, an RNA sequence complementary to an enzyme coding sequence is produced. The sense orientation is desirable when one wishes to produce the selected enzyme in plant cells, whereas the antisense strand may be useful to inhibit production of related plant enzymes. Regions of homology have been observed, for example, upon comparison of *E. coli* glgC sequence to that of a rice ADP glucose pyrophosphorylase. Either method may be useful in obtaining an alteration in the polysaccharide or dry matter content of a plant. The presence of the selected enzyme sequences in the genome of the plant host cell may be confirmed, e.g., by a Southern analysis of DNA or a Northern analysis of RNA sequences or by PCR methods.

In addition to sequences providing for transcriptional initiation in a plant cell, also of interest are sequences which provide for transcriptional and translational initiation of a desired sequence encoding a glycogen biosynthetic enzyme. Translational initiation regions may be provided from the source of the transcriptional initiation region or from the gene of interest. In this manner, expression of the selected enzyme in a plant cell is provided. The presence of the enzyme in the plant host cell may be confirmed by a variety of methods including a immunological analysis of the protein (e.g. Western or ELISA), as a result of phenotypic changes observed in the cell, such as altered starch content, altered starch branching, etc., or by assay for increased enzyme activity, and the like. If desired the enzyme may be harvested from the plant host cell or used to study the effect of the enzyme on plant cell functions, especially in the plastid organelles.

Other sequences may be included in the nucleic acid construct providing for expression of the selected enzymes ("expression constructs") of this invention, including endogenous plant transcription termination regions which will be located 3' to the desired enzyme encoding sequence. In one embodiment of this invention, transcription termination sequences derived from a patatin gene are preferred. Transcription termination regions may also be derived from genes other than those used to regulate the transcription in the nucleic acid constructs of this invention. Transcription termination regions may be derived from a variety of different gene sequences, including the Agrobacterium, viral and plant genes discussed above for their desirable 5' regulatory sequences.

Further constructs are considered which provide for transcription and/or expression of more than one selected enzyme. For example, one may wish to provide enzymes to plant cells which provide for modification of the starch synthesized, as well as for an increase or decrease in overall starch production. Examples of enzymes which may prove useful in modifying starch structure are those which catalyze reactions involving UDP- or ADP-glucose, for example glycogen synthase or branching enzyme. However, to provide for increased or decreased starch production, or the production of starch degradation products, one may wish to utilize sequences encoding enzymes which catalyze formation of the nucleotide-glucose molecule, such as ADP-glucose pyrophosphorylase in bacteria, or glucose-1-phosphate uridylyltransferase in mammals. Although plants typically utilize ADP-glucose, UDP-glucose may also be useful.

In providing for transcription and/or expression of the selected enzyme sequences, one may wish to limit these enzymes to plant cells which synthesize and store reserve starch. Towards this end, one can identify useful transcriptional initiation regions that provide for expression preferentially in the roots, tubers, seeds, or other starch-containing tissues of a desired plant species. These sequences may be identified from cDNA libraries using differential screening techniques, for example, or may be derived from sequences known in the literature of particular interest in a presently preferred embodiment of the invention is a transcriptional initiation region from the patatin gene of potato, which demonstrates preferential expression in the potato tuber. Similarly, other promoters which are preferentially expressed in the starch-containing tissues, such as the zein genes in corn, as opposed to other plant structures are desirable.

In developing the nucleic acid constructs of this invention, the various components of the construct or fragments thereof will normally be inserted into a convenient cloning vector, e.g. a plasmid, which is capable of replication in a bacterial host, e.g. *E. coli*. Numerous vectors exist that have been described in the literature, many of which are commercially available. After each cloning, the cloning vector with the desired insert may be isolated and subjected to further manipulation, such as restriction, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

The constructs of this invention providing for transcription and/or expression of the enzyme sequences of this invention may be utilized as vectors for plant cell transformation. The manner in which nucleic acid sequences are introduced into the plant host cell is not critical to this invention. Direct DNA transfer techniques, such as electroporation, microinjection or DNA bombardment may be useful. To aid in identification of transformed plant cells, the constructs of this invention may be further manipulated to include plant selectable markers. The use of plant selectable markers is preferred in this invention as the amount of experimentation required to detect plant cells is greatly reduced when a selectable marker is expressed. Useful selectable markers include enzymes which provide for resistance to an antibiotic such as gentamicin, hygromycin, kanamycin, and the like. Similarly, enzymes providing for production of a compound identifiable by color change, such as GUS, or luminescence, such as luciferase, are useful.

An alternative method of plant cell transformation employs plant vectors which contain additional sequences which provide for transfer of the desired enzyme sequences to a plant host cell and stable integration of these sequences into the genome of the desired plant host. Selectable markers may also be useful in these nucleic acid constructs to provide for differentiation of plant cells containing the desired sequences from those which have only the native genetic material. Sequences useful in providing for transfer of nucleic acid sequences to host plant cells may be derived from plant pathogenic bacteria, such as Agrobacterium or Rhizogenes, plant pathogenic viruses, or plant transposable elements.

When Agrobacterium is utilized for plant transformation, it may be desirable to have the selected nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri-containing the T-DNA for recombination may be armed (capable of causing gall formation), or disarmed (incapable of causing gall formation), the latter being, permissible so long as a functional complement of the vir genes, which encode trans-acting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the expression vectors in host Agrobacterium cells.

Utilizing vectors such as those described above, which can replicate in Agrobacterium is preferred. In this manner, recombination of plasmids is not required and the host Agrobacterium vir regions can supply transacting factors required for transfer of the T-DNA bordered sequences to plant host cells.

In general, the plant vectors of this invention will contain the selected enzyme sequence(s), alone or in combination with transit peptides, and endogenous plant sequences providing for transcription or expression of these sequences in a plant host cell. The plant vectors containing the desired sequences may be employed with a variety of plant cells, particularly plants which produce and store reserve starch. Plants of interest include, but are not limited to plants which have an abundance of starch in the seed, such as corn (e.g. *Zea mays*), cereal grains (e.g. wheat (*Triticum* spp.), rye (*Secale cereale*), triticale (*Triticum aestium×Secale cereale* hybrid), etc.), waxy maize, sorghum (e.g. *Sorghum bicolor*) and rice (e.g. *Oryza sativa*), in the root structures, such as potato (e.g., Irish (*Solanum tuberosum*), Sweet (*Ipomoea batatas*), and yam (*Discorea* spp.)), tapioca (e.g. cassava (*Manihot esculenta*)) and arrowroot (e.g., Marantaceae spp., Cycadaceae spp., Cannaceae spp., Zingiberaceae spp., etc.), or in the stem, such as sago (e.g. Palmae spp., Cycadales spp.). Starch is also found in botanical fruits, including for example tomato, apple and pear.

Also considered part of this invention are plants containing the nucleic acid sequences of this invention, and following from that, plants containing the selected enzymes as the result of expression of the sequences of this invention in plant cells or having a decreased expression of a native enzyme. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations either from seed or using vegetative propagation techniques.

Of particular interest are plant parts, e.g. tissues or organs, (and corresponding cells) which form and store reserve starch, such as roots, tubers, and seeds. Of more particular interest are potato tubers containing the selected enzymes. It can be recognized that the modification of enzymes in plants may also result in desirable alterations in the plant cells or parts. These alterations may include modification of dry matter content, free sugar content or of starch content and/or structure, or modification of specific gravity. The novel plant cells or plant parts can thus be harvested and used for isolation of the altered material.

Once the cells are transformed, transgenic cells may be selected by means of a marker associated with the expression construct. The expression construct will usually be joined with such a marker to allow for selection of transformed plant cells, as against those cells which are not transformed. As before, the marker will usually provide resistance to an antibiotic, e.g., kanamycin, gentamicin, hygromycin, and the like, or an herbicide, e.g. glyphosate, which is toxic to plant cells at a moderate concentration.

After transformation, the plant cells may be grown in an appropriate medium. In the case of protoplast transformations, the cell wall will be allowed to reform under appropriate osmotic conditions. In the case of seeds or embryos, an appropriate germination or callus initiation medium would be employed. For transformation in explants, an appropriate regeneration medium is used.

The callus which results from transformed cells may be introduced into a nutrient medium which provides for the formation of shoots and roots, and the resulting plantlets planted and allowed to grow to seed. During the growth, tissue may be harvested and screened for the presence of expression products of the expression construct. After growth, the transformed hosts may be collected and replanted. One or more generations may then be grown to establish that the enzyme structural gene is inherited in Mendelian fashion.

The ability to modify the composition of a host plant offers potential means to alter properties of the plant produce, such as, e.g., by the replacement of endogenous starch with oligosaccharides comprising glucopyranose units. These oligosaccharides, cyclodextrins for example, may then be purified away from the other plant components. For example, by modifying crop plant cells by introducing a functional structural gene expressing a selected enzyme, one can provide a wide variety of crops which have the ability to produce starch degradation products, and desirably such production will be effected without damaging the agronomic characteristics of the host plant. In this manner, substantial economies can be achieved in labor and materials for the production of starch degradation products, while minimizing the detrimental effects of starch degradation on the host plants.

Preferably, the activity of the starch degradation enzyme will be localized in the starch storage organelles, tissues or regions of the host plant, e.g., the amyloplast of a host potato tuber. The structural gene will manifest its activity by mediating the production of degradation products in at least one portion of the genetically modified host plant.

The following examples serve to illustrate certain preferred embodiments and aspects of the present invention and are not to be construed as limiting the scope thereof.

EXPERIMENTAL

In the experimental disclosure which follows, the following abbreviations apply: eq (equivalents); M (Molar); mM (millimolar); $\mu$M (micromolar); N (Normal); mol (moles); mmol (millimoles); $\mu$mol (micromoles) nmol (nanomoles); kg (kilograms); g (grams); mg (milligrams); $\mu$g (micrograms); ng (nanograms); L (liters); ml (milliliters); $\mu$l (microliters); cm (centimeters); mm (millimeters); $\mu$m (micrometers); nm (nanometers); V (volts); $\mu$F (microfarads) and °C. (degrees Centigrade).

In order to demonstrate the practice of the present invention in utilizing reserve polysaccharide biosynthetic enzymes, the following examples convey an embodiment for the biosynthesis of glycogen.

EXAMPLE 1

Cloning of Glycogen Biosynthetic Enzyme Genes

A. Cloning and Sequencing of a GlgA Gene From E. coli

Total genomic DNA-is prepared from E. coli K12 618 (Leung et al., J. of Bacteriology (1986) 167:82–88) by growing a 5 ml culture in ECLB (Maniatis, T. et al., Molecular Cloning: A Laboratory Manual, (1982) Cold Spring Harbor, N.Y.) overnight at 37° C. The bacteria are pelleted by centrifugation for 10 minutes at 4500×g, the supernatant is discarded, and the pellet is resuspended in 2.5 ml of 10 mM Tris, 1 mM EDTA buffer. To this suspension is added 500 $\mu$l of a 5 mg/ml Pronase® protease (Calbiochem Brand Biochemicals; La Jolla, Calif.) solution and 2 ml of 2% lauryl sulfate, sodium salt (Sigma; St. Louis, Mo.), with gentle mixing, and the suspension is incubated at 37° C. for 50 minutes. A clear solution indicates that the bacteria have lysed. The solution is then extracted with 5 ml phenol, then 5 ml phenol:chloroform:isoamyl alcohol (25:24:1), followed by 5 ml chloroform. Nucleic acids are precipitated from the aqueous phase with 1/10 volume of 3M sodium acetate and two volumes of 100% ethanol, and the tube is incubated at room temperature for 1 hour. Nucleic acids are removed from solution and resuspended in 1 ml water. A second ethanol precipitation is performed and the nucleic acids are resuspended in 200 $\mu$l of 10 mM Tris, 1 mM EDTA buffer.

Synthetic oligonucleotides, str1 and str2, corresponding to sequences flanking the 1.4 kb glgA (glycogen synthase—EC 2.4.1.21) gene of E. coli (Kumar et al., J. of Biol. Chemistry (1986) 261:16256–16259) and containing restriction sites for BglII (str1) and SalI (str2) are synthesized on an Applied Biosystems 380A DNA synthesizer (Foster City, Calif.) in accordance with the manufacturer's instructions.

The nucleic acid preparation of E. coli is treated with RNAse and the DNA is used as a template in a polymerase chain reaction (PCR) with str1 and str2 as primers. A Perkin-Elmer/Cetus (Norwalk, Conn.) thermal cycler is used with the manufacturer's reagents and in accordance with the manufacturer's instructions. The reaction mixture contains 41.5 $\mu$l H$_2$O, 10 $\mu$l 10×reaction buffer, 16 $\mu$l dNTP's [1.25 mM dCTP, dATP, dGTP & dTTP], 5 $\mu$l str1 (20 mM), 5 $\mu$l str2 (20 mM), 22 $\mu$l total E. coli DNA (0.05 $\mu$g/$\mu$l), and 0.5 $\mu$l Taq polymerase. The reaction is performed for 15 cycles with melting (denaturation) for 1 minute at 94° C., annealing (hybridization) for 2 minutes at 37° C. and chain elongation for 3 minutes at 72° C. The reaction is then performed for an additional 10 cycles with melting for 1 minute at 94° C., annealing for 2 minutes at 37° C. and chain elongation at 72° C. for 3 minutes 15 seconds initially and increasing the time by 15 seconds each cycle so that the last cycle is 5 minutes 45 seconds.

The resulting PCR products (~1.4 kb) are digested with BglII and SalI and ligated into a SalI and BglII digest of pCGN789, a pUC based vector similar to pUC119 with the normal polylinker replaced by a synthetic linker which contains the restriction digest sites EcoRI, SalI, BglII, PstI, XhoI, BamHI, and HindIII. The ligated DNA is transformed into E. coli DH5α. The transformed cells are plated on ECLB containing penicillin (300 mg/L), IPTG and X-Gal (Vieira and Messing, Gene (1982) 19:259–268). White colonies are picked to ECLB containing penicillin (300 mg/L) and flooded with I$_2$/KI (0.2% I$_2$ in 0.4% KI). Clones producing a brown color, which indicates excess starch production, are selected. One clone, glgA-2, is selected and the DNA and translated amino acid sequences are determined (see, FIGS. 1 and 2 and SEQ ID NOS: 1–2). The DNA sequence is 98% homologous to the published sequence (Kumar et al, supra) and 96% homologous at the amino acid level.

B. Cloning and Sequencing of a GlgC Gene From E. coli

Synthetic oligonucleotides, glgC1 and glgC2, corresponding to sequences flanking the 1.3 kb glgC (ADP-glucose pyrophosphorylase—EC 2.7.7.27) gene of E. coli (Baecker et al., J. of Biol. Chemistry (1983) 258:5084–5088) and containing restriction sites for BglII (glgC1) and SalI (glgC2) are synthesized on an Applied Biosystems 380A DNA synthesizer (Foster City, Calif.) in accordance with the manufacturer's instructions.

Total genomic DNA is prepared from E. coli K12 618 as described above. The nucleic acid preparation of E. coli is treated with RNAse and the DNA is used as a template in a polymerase chain reaction (PCR) with glgC1 and glgC2 as primers. A Perkin-Elmer/Cetus (Norwalk, Conn.) thermal cycler is used with the manufacturer's reagents as described above.

The resulting PCR products (~1.3 kb) are digested with BglII and SalI and ligated into a SalI and BglII digest of pCGN789 (described above). The ligated DNA is transformed into *E. coli* DH5α, and the transformed cells are plated as described above. Clones producing excess starch are selected as described above. One clone, pGlgC-37, is selected and the DNA sequence (SEQ ID NO: 3) determined (see, FIG. 3). The DNA sequence is 99% homologous to the published sequence (Baecker et al, supra) of glgC from *E. coli* K-12. The glgC from *E. coli* 618 is a mutant and the amino acid sequence of this mutant differs from that of *E. coli* K-12 at five amino acids (Lee et al., *Nucl. Acids Res.* (1987) 15:10603). The translated amino acid sequence of pGlgC-37 differs from that of the glgC from *E. coli* 618 at a single amino acid; the asparagine (Asn) at position 361 of the *E. coli* 618 mutant is an aspartate (Asp) in the translated amino acid sequence of pGlgC-37 (FIG. 3).

EXAMPLE 2
Attachment of Glycogen Genes to SSU Leader Sequence
A. Construction of SSU+aroA Transit Peptide Plasmid pCGN1132 contains a 35S promoter, ribulosebisphosphate carboxylase small subunit (5'-35S-SSU) leader from soybean plus 48 bp of mature small subunit (SSU) gene from pea, and aroA sequence (the gene locus which encodes 5-enolpyruvyl-3-phosphoshikimate synthetase (EC 2.5.1.19)). It is prepared from pCGN1096, a plasmid containing a hybrid SSU gene, which carries DNA encoding mature SSU protein from pea, and SstI and EcoRI sites 3' of the coding region (used in the preparation of pCGN1115, a plasmid having a 5'-35S-SSU+48-aroA-tml-3'sequence) and pCGN1129, (a plasmid having a 35S promoter in a chloramphenicol resistance gene (Cam$^r$) backbone).
Construction of pCGN1096

The aroA moiety of pCGN1077 is removed by digestion with SphI and SalI. (The construction of pCGN1077 and other constructs hereunder are described in detail in co-pending U.S. application Ser. No. 06/097,498, filed Sep. 16, 1987, which is hereby incorporated by reference). In its place is cloned the region coding for the mature pea SSU protein, as an SphI-PstI fragment, which is then excised with SphI and SalI. The resulting plasmid, pCGN1094, codes for a hybrid SSU protein having the transit peptide of the soybean clone, and the mature portion of the pea clone (SEQ ID NOS: 15–27) and contains SstI and EcoRI sites 3' of the coding region. The HindIII to BamHI region of transposon Tn6 (Jorgensen et al., *Mol. Gen. Genet.* (1979) 177:65) encoding the kanamycin resistance gene (Kan$^r$) is cloned into the same sites of pBR322 (Bolivar et al., *Gene* (1977) 2:95–133) generating pDS7. The BglII site 3' of the Kan$^r$ gene is digested and filled in with the large fragment of *E. coli* DNA polymerase 1 and deoxynucleotides triphosphate. An SstI linker is ligated into the blunted site, generating plasmid pCGN1093. Plasmid pPMG34.3 is digested with SalI, the site filled in as above and EcoRI linkers are ligated into the site resulting in plasmid pCGN1092. The latter plasmid is digested with SstI and SmaI and the Kan$^r$ gene excised from pCGN1093 with SstI and SmaI is ligated in, generating pCGN1095. The Kan$^r$ and aroA genes are excised as a piece from pCGN1095 by digestion with SstI and EcoRI and inserted into the SstI and EcoRI sites of pCGN1094, producing pCGN1096. Summarizing, pCGN1096 contains (5'-3') the following pertinent features: The SSU gene—a polylinker coding for PstI, SalI, SstI, and KpnI—the Kan$^r$ gene—SmaI and BamHI restriction sites—the aroA gene without the original ATG start codon.
Construction of pCGN1115

Plasmid pCGN1096 is digested to completion with SalI and then digested with exonuclease Bal31 (BRL; Gaithersburg, Md.) for 10 minutes, thus deleting a portion of the mature SSU gene. The resulting plasmid is then digested with SmaI to eliminate the Kan$^r$ gene and provide blunt ends, recircularized with T4 DNA ligase and transformed into *E. coli* LC3 (Comai et al., *Science* (1983) 221:370–371), an aroA mutant. DNA isolated from aroA$^+$ and Kan$^r$ colonies is digested with BamHI and SphI and ligated with BamHI- and SphI-digested M13mp18 (Norrander et al., *Gene* (1983) 26:101–106 and Yanisch-Perron et al., *Gene* (1985) 33:103–119) DNA for sequencing. Clone 7 has 48 bp of the mature SSU gene remaining and the 3'-end consists of phe-glu-thr-leu-ser (SEQ ID NO: 1). Clone 7 is transformed into *E. coli* strain 71-18 (Yanish-Perron et al. (1985) supra) and DNA isolated from transformants is digested with SphI and ClaI to remove the 0.65 kb fragment containing the 48 bp of mature protein and the 5'-end of the aroA gene. Plasmid pCGN1106 (Comai, L. et al., *J. Biol. Chem.* (1988) 263:15104–15109) is also digested with SphI and ClaI and the 6.8 kb isolated vector fragment is ligated with the 0.65 kb fragment of clone 7 to yield pCGN1115 (5'-35S-SSU+48-aroA-tml-3')
Construction of pCGN1129

The 7.2 kb plasmid pCGN1180 (35S-SSU+70-aroA-ocs3') (Comai et al. (1988) supra) and the 25.6 kp plasmid pCGN594 (LB-Gent$^r$-ocs5'-Kan$^r$-ocs3'-RB) (construction of pCGN594 is described in co-pending U.S. application Ser. No. 07/382,802, filed Jul. 19, 1989) are digested with HindIII and ligated together to yield the 32.8 kb plasmid pCGN1109 (LB-Gent$^r$-35S-SSU+70-aroA-ocs3'-ocs5'-Kan$^r$-ocs3'-RB).

Plasmid pCGN1109 is digested with EcoRI to delete an internal 9.1 kb fragment containing the SSU leader plus 70 bp of the mature SSU gene, the aroA gene and its ocs3' terminator, the Amp$^r$ backbone from pCGN1180 and ocs5'-Kan$^r$-ocs3' from pCGN594. The EcoRI digest of pCGN1109 is then treated with Klenow fragment to blunt the ends, and an XhoI linker (dCCTCGAGG) (New England Biolabs.; Beverly, Mass.) is ligated in, yielding pCGN1125 (LB-35S-RB).

Plasmid pCGN1125 is digested with HindIII and BglII to delete the 0.72 kb fragment of the 35S promoter. This digest is ligated with HindIII- and BamHI-digested Cam$^r$ vector, pCGN786 (described in co-pending U.S. application Ser. No. 07/382,803, filed Jul. 19, 1989). The resulting 3.22 kb plasmid, pCGN1128, contains the 35S promoter with a 3' multilinker in a Cam$^r$ backbone.

Plasmid pCGN1128 is digested with HindIII, treated with Klenow fragment to blunt the ends, and ligated with BglII linkers to yield pCGN1129, thus changing the HindIII site located 5' to the 35S promoter into a BglII site.
B. Transit Peptide Joined to GlgA Gene Plasmid pCGN1115 is digested with SalI to remove a 1.6 kb fragment containing the SSU leader plus 48 bp of the mature SSU gene and the aroA gene. An XhoI digest of pCGN1129 opens the plasmid 3' to the 35S promoter. Ligation of these two digests yields the 4.8 kb plasmid pCGN1132, containing 5'-35S-SSU leader plus 48 bp of mature SSU-aroA.

Plasmid pGlgA-2 is digested with BglII and SalI and ligated to pCGN1132 that has been digested with BamHI and SalI. A clone containing 5'-35S-SSU+48 bp-glgA-3' is selected and designated pCGN1439.

C. Transit Peptide Joined to GlgC Gene

Plasmid pGlgC-37 is digested with BglII and SalI and ligated to pCGN1132 that has been digested with BamHI and SalI. A clone containing 5'-35S-SSU+48 bp-glgC-3' is selected and designated pCGN1440.

EXAMPLE 3

Cloning of Patatin Regulatory Regions and Preparation of Patatin-5'-nos-3' Expression Cassettes This example describes the cloning of a patatin-5' regulatory region from potato and the preparation of patatin-5'-nos-3' expression cassette pCGN2143.

Genomic DNA is isolated from leaves of *Solanum tuberosum* var. *Kennebec* (SEQ ID NO: 28) as described in Dellaporta et al., *Plant Mol. Biol. Reporter* (1983) 1(4) :19–21), with the following modifications: approximately 9 g fresh weight of leaf tissue is ground, a polytron grinding is not performed and +in the final step the DNA is dissolved in 300 µl of 10 mM Tris, 1 mM EDTA, pH 8.

A synthetic oligonucleotide, pat1, containing digestion sites for NheI, PstI and XhoI with 24 bp of homology to the 5'-region of a 701 bp fragment (coordinates 1611 to 2313) 5' to a class I patatin gene, isolated from *Solanum tuberosum* var. *Maris Piper* (SEQ ID NO: 29), (SEQ ID NO: 31) (Bevan et al., *NAR* (1986) 14:4625–4638), is synthesized (Applied BioSystems 380A DNA synthesizer). A second synthetic oligonucleotide, pat2, containing digestion sites for BamHI and SpeI with 25 bp of homology to the 3' region of the 703 bp piece is also synthesized.

Using the genomic potato DNA as a template, and pat1 and pat2 as primers, a polymerase chain reaction (PCR) is performed in a Perkin-Elmer/Cetus thermal cycler with the manufacturer's reagents and in accordance with the manufacturer's instructions. The reaction contains 62.5 µl H$_2$O, 10 µl 10×Reaction buffer, 16 µl dNTP's [1.25 mM dCTP, that has been linearized with EcoRI and treated with Klenow polymerase to generate blunt ends. A plasmid, pCGN2162 which has the following restriction sites at the 3' end of nos is selected: 5'-EcoRI-NheI-XhoI-PstI-EcoRI.

Construction of pCGN1586/1586N

Plasmid pCGN2113 (6.1 kb) contains a double-35S promoter (D35S) and the tml-3' region with multiple cloning sites between them, contained in a pUC-derived plasmid backbone bearing an ampicillin resistance gene (Amp'). The promoter/tml cassette is bordered by multiple restriction sites for easy removal. Plasmid pCGN2113 is digested with EcoRI and SacI, deleting the 2.2 kb tml-3' region. Plasmid pBI221.1 (Jefferson, R. A., *Plant Mol. Biol. Reporter* (1987) 5:387–405) is digested with EcoRI and SacI to delete the 0.3 kb nos-3' region. The digested pCGN2113 and pBI221.1 DNAs are ligated together, and the resultant 4.2 kb recombinant plasmid with the tml-3' of pCGN2113 replaced by nos-3' is designated pCGN1575 (5'-D35S-nos-3').

Plasmid pCGN1575 is digested with SphI and XbaI, blunt ends generated by treatment with Klenow fragment, and the ends are ligated together. In the resulting plasmid, pCGN1577, the SphI, PstI, SalI and XbaI sites 5' of the D35S promoter are eliminated.

Plasmid pCGN1577 is digested with EcoRI, the sticky ends blunted by treatment with Klenow fragment, and synthetic BglII linkers (d(pCAGATCTG) New England Biolabs, Inc.; Beverly, Mass.) are ligated in. A total of three BglII linkers are ligated into the EcoRI site creating two PstI sites. The resulting plasmid, termed pCGN1579 (D35S-nos-3'), has a 3' polylinker consisting of 5'-EcoRI, BglII, PstI, BglII, PstI, BglII, EcoRI-3'.

A tobacco mosaic virus omega' (TMVΩ') region (Gallie et al., *NAR* (1987) 15(21):8693–8711) with BglII, NcoI, BamHI, SalI and SacI restriction sites:

```
         BglII
5'-CAGGAGATCT TATTTTTACA ACAATTACCA ACAACAACAA ACAACAAACA

ACATTACAAT TACTATTTAC AATTACACCA TGGATCCGTC GACGAGCTC 3'
                                 NcoI  BamHI SalI    SacI
  (SEQ ID NO: 2)
``` dATP, dGTP & dTTP], 5 µl pat1 (20 mM), 5 µl pat2 (20 mM), 1 µl potato genomic DNA (3 µg/µl), 0.5 µl Taq polymerase. The PCR is performed for 25 cycles with melting for 1 minute at 94° C., annealing for 2 minutes at 37° C. and chain elongation for 3 minutes at 72° C. The resulting PCR product fragments (approximately 700 bp) are digested with NheI and BamHI. Plasmid pCGN1586N ('5-D35S-TM Ω'-nos-3'; pCGN1586 (described below) having a NheI site 5' to the 35S region) is digested with NheI and BamHI to delete the D35S-Ω' fragment. Ligation of NheI-BamHI digested pCGN1586N, which contains the nos-3' region, and the PCR fragments yields a patatin-5'-nos3' cassette with SpeI, BamHI, SalI and SstI restriction sites between the 5' and 3' regions for insertion of a DNA sequence of interest.

The 5' region of a clone, designated pCGN2143 is sequenced. Plasmid pCGN2143 has a Kennebec patatin-5' region that is 702 bp in length and 99.7% homologous to the native sequence (as reported by Bevan (1986) supra).

Synthetic oligonucleotides, pat5 and pat6, are prepared as described above. Pat5 and pat6 contain complementary sequences which contain the restriction digest sites NheI, XhoI and PstI. Pat5 and pat6 are annealed to create a synthetic linker. The annealed linker is ligated to pCGN2143 is synthesized on an Applied Biosystems® 380A DNA synthesizer and digested with BglII and SacI. Plasmid pCGN1577 is digested with BamHI and SacI and the synthetic TMVΩ' is ligated in between the 5'-D35S and nos-3' regions. The resulting plasmid is designated pCGN1586 (5'-D35S-TMVΩ'-nos-3'). Plasmid pCGN1586N is made by digesting pCGN1586 with HindIII and filling in the 5' overhang with Klenow fragment, thus forming a NheI site 5' to the D35S region.

Plasmid pCGN2143 is also described in co-pending U.S. application Ser. No. 07/536,392 filed Jun. 1, 1990, which is hereby incorporated by reference.

EXAMPLE 4

Preparation of Binary Vectors

This example describes the construction of a binary vector containing: (1) the patatin-5' region from *Solanum tuberosum* var. *Kennebec*, (2) DNA encoding a transit peptide from soybean RuBisCo SSU protein, (3) 48 bp of DNA encoding 16 amino acids of mature RuBisCo SSU protein. from pea, (4) the glgA coding region from *E. coli* 618 and (5) the nos-3' region.

A. GlgA Construct

Plasmid pCGN2162 prepared as described in Example 3 is digested with SpeI and SalI, opening the plasmid between the patatin-5' region and nos-3' region. Plasmid pCGN1439 (described in Example 2) is digested with XbaI and SalI and ligated with pCGN2162 to yield pCGN1454. Plasmid pCGN1454 consists of 5'-Kennebec patatin-SSU+48-glgA-nos3'.

Plasmid pCGN1454 is digested with XhoI and treated with Klenow polymerase to generate blunt ends. Plasmid pCGN1557 is digested with XbaI and treated with Klenow polymerase to generate blunt ends. The fragments resulting from the digests are ligated together. The transformation is plated onto ECLB containing gentamycin, IPTG and X-Gal. White colonies are picked and screened for ampicillin sensitivity. Gent$^r$, Amp$^s$ clones are analyzed and two clones are selected. Plasmid pCGN1457 has the 5'patatin-SSU+48 bp-glgA-nos3' inserted into pCGN1557 such that it transcribes in the opposite direction from the 35S-Kan$^r$-tml gene. Plasmid pCGN1457B has the 5'patatin-SSU+48 bp-glgA-nos3' inserted into pCGN1557 such that it transcribes in the same direction as the 35S-Kan$^r$-tml gene.

B. GlgC Construct

Plasmid pCGN2162 prepared as described in Example 3 is digested with SpeI and SalI, opening the plasmid between the patatin-5' region and nos-3' region. Plasmid pCGN1440 (described in Example 2) is digested with XbaI and SalI and ligated with pCGN2162 to yield pCGN1453. Plasmid pCGN1453 consists of 5'-Kennebec patatin-SSU+48-glgC-nos3'.

Plasmid pCGN1453 is digested with PstI and ligated to a PstI digest of pCGN1557. The transformation is plated as described above and colonies are screened for ampicillin sensitivity. Gent$^r$, Amp$^s$ clones are analyzed and one clone, pCGN1455, is selected. Plasmid pCGN1455 has the 5'patatin-SSU+48 bp-glgC-nos3' inserted into pCGN1557 such that it transcribes in the same direction as the 35S-Kan$^r$-tml gene.

C. Construction of pCGN1557

Plasmid pCGN155.7 (McBride and Summerfelt, *Plant Mol. Biol.* (1990) 14(27):269–276) is a binary plant transformation vector containing the left and right T-DNA borders of *Agrobacterium tumefaciens* octopine Ti-plasmid pTiA6 (Currier and Nester, *J. Bact.* (1976) 126:157–165), the gentamicin resistance gene (Gen$^r$) of pPH1JI (Hirsch and Beringer, *Plasmid* (1984) 12:139–141), an *Agrobacterium rhizogenes* Ri plasmid origin of replication from pLJbB11 (Jouanin et al., *Mol. Gen. Genet.* (1985) 201:370–374), a 35S promoter-Kan$^r$-tml-3' region capable of conferring kanamycin resistance to transformed plants, a ColE1 origin of replication from pBR322 (Bolivar et al. (1977) supra) and a lacZ' screenable marker gene from pUC18 (Yanisch-Perron et al., (1985) supra). The construction of pCGN1557 is also described in co-pending U.S. application Ser. No. 07/494,722, filed Mar. 16, 1990.

EXAMPLE 5

Preparation of Transgenic Plants

This example describes the transformation of *Agrobacterium tumefaciens* with glycogen biosynthetic enzyme gene nucleic acid constructs in accordance with the present invention and the cocultivation of these *A. tumefaciens* with plant cells to produce transgenic plants containing the glycogen constructs.

A. Transformation of *Agrobacterium tumefaciens*

Cells of *Agrobacterium tumefaciens* strain 2760 (also known as LBA4404, Hoekema et al., *Nature* (1983) 303:179–180) are transformed with binary vectors, such as pCGN1457, pCGN1457B and pCGN1455 (as described in Example 4) using the method of Holsters, et al., (*Mol. Gen. Genet.*, (1978) 163:181–187). The transformed *A. tumefaciens* are then used in the co-cultivation of plants.

The Agrobacterium are grown on AB medium ($K_2HPO_4$ 6 g/L, $NaH_2PO_4 \cdot H_2O$ 2.3 g/L, $NH_4Cl$ 2 g/L, KCl 3 g/L, glucose 5 g/L, $FeSO_4$ 2.5 mg/L, $MgSO_4$ 246 mg/L, $CaCl_2$ 14.7 mg/L, 15 g/L agar), plus 100 µg/L gentamycin sulfate and 100 µg/L streptomycin sulfate for 4–5 days. Single colonies are inoculated into 10 ml of MG/L broth (per liter: 5 g mannitol, 1 g L-Glutamic acid or 1.15 g sodium glutamate, 0.5 g $KH_2PO_4$, 0.10 g NaCl, 0.10 g $MgSO_4 \cdot 7H_2O$, 1 µg biotin, 5 g tryptone, 2.5 g yeast extract; adjust pH to 7.0) and are incubated overnight in a shaker at 30° C. and 180 rpm. Prior to co-cultivation, the Agrobacterium culture is centrifuged at 12,000×g for 10 minutes and resuspended in 20 ml of MS medium (#510-1118, Gibco; Grand Island, N.Y.).

B. Cocultivation with Potato Cells

Feeder plates are prepared by pipetting 0.5 ml of a tobacco suspension culture (~$10^6$cells/ml) onto 0.8% agar co-cultivation medium, containing Murashige and Skoog salts (#510-117, Gibco; Grand Island, N.Y.), thiamine-HCl (1.0 mg/L), nicotinic acid (0.5 mg/L), pyridoxine HCl (0.5 mg/L), sucrose (30 g/L), zeatin riboside (5 µM), 3-indoleacetyl-DL-aspartic acid (3 µM), pH 5.9. The feeder plates are prepared one day in advance and incubated at 25° C. A sterile 3 mm filter paper disk is placed on top of the tobacco cells after the suspension cells have grown for one day.

Tubers of *Solanum tuberosum* var *Russet Burbank* between the age of 1 and 6 months post harvest are peeled and washed in distilled water. All subsequent steps are carried out in a flow hood using sterile techniques. For surface sterilization, tubers are immersed in a solution of 10% commercial bleach (sodium hypochlorite) with 2 drops of Ivory® liquid soap per 100 ml for 10 minutes. Tubers are rinsed six times in sterile distilled water and kept immersed in sterile liquid MS medium (#1118, Gibco; Grand Island; N.Y.) to prevent browning. Tuber discs (1–2 mm-thick) are prepared by cutting columns of potato tuber with a ~1 cm in diameter cork borer and, slicing the columns into discs of the desired thickness. Discs are placed into the liquid MS medium culture of the transformed *Agrobacterium tumefaciens* containing the binary vector of interest ($1\times10^7$–$1\times10^8$ bacteria/ml) until thoroughly wetted. Excess bacteria are removed by blotting discs-on sterile paper towels. The discs are co-cultivated with the bacteria for 48 hours on the feeder plates and then transferred to regeneration medium (co-cultivation medium plus 500 mg/L carbenicillin and 100 mg/L kanamycin). In 3 to 4 weeks, shoots develop from the discs.

When shoots are approximately 1 cm, they are excised and transferred to a 0.8% agar rooting medium containing MS salts, thiamine-HCl (1.0 mg/L), nicotinic acid (0.5 mg/L), pyridoxine-HCl (0.5 mg/L), sucrose (30 g/L), carbenicillin (200 mg/L) and kanamycin (100–200 mg/L) pH 5.9. Plants are rooted two times with at least one rooting taking place on rooting medium with the higher level of kanamycin (200 mg/L). Plants which have rooted twice are then confirmed as transformed by performing NPTII blot activity assays (Radke, S. E. et al, *Theor, Appl. Genet.* (1988) 75:685–694). Plants which are not positive for NPTII activity are discarded.

EXAMPLE 6

Analysis of Tubers from Transformed Potato Plants

In this Example, measurement of specific gravity in tubers from transgenic potato plants is described.

Rooted plants, transformed as described in Example 5, are cut into five sections at the internodes and each section is rooted again, also as described in Example 5. The newly rooted plants are transplanted from rooting medium to soil and placed in a growth chamber (21° C., 16 hour days with 250–300 $\mu E/m^2/sec$). Soil is prepared as follows: For about 340 gallons, combine 800 pounds 20/30 sand (approximately 14 cubic feet), 16 cubic feet Fisons Canadian Peat Moss, 16 cubic feet #3 vermiculite, and approximately 4.5 pounds hydrated lime in a Gleason mixer. The soil is steamed in the mixer for two hours; the mixer mixes for about 15 seconds at intervals of fifteen minutes over a period of one hour to ensure even heating throughout the soil. During and after the process of steaming, the soil reaches temperatures of at least 180° F. for one hour. The soil is left in the mixer until the next day. At that time, hydrated lime is added, if necessary, to adjust the pH to range between 6.30 and 6.80.

The relative humidity of the growth chamber is maintained at 70–90% for 2–4 days, after which the humidity is maintained at 40–60%. When plants are well established in the soil, after approximately two weeks, they are transferred to a greenhouse. In the greenhouse, plants are grown in 6.5 inch pots in a soil mix of peat:perlite:vermiculite (11:1:9), at an average temperature of 24° C. day/12° C. night. Day length is approximately 12 hours and light intensity levels vary from approximately 600 to 1000 $\mu E/m^2/sec$.

Tubers from each plant are harvested and washed 14 weeks after transfer to the greenhouse. Immediately after harvest, three to five uniformly sized tubers from each pot are weighed and their specific gravity determined. In determining specific gravity, the tubers from each plant are first collectively weighed in air and then collectively weighed in water. Specific gravity is determined, where x=the weight of tubers in air and y=the weight of tubers in water, as x/(x−y).

In general, the specific gravities of tubers from five replicates of plants transformed with the glgA constructs (pCGN1457 and pCGN1457B) and of tubers from control plants are determined. Control plants include regenerated non-transformed potato plants and transgenic potato plants which lack the glgA constructs. Controls, are subjected to the transformation and regeneration culture and growth conditions described above in production of glgA transformed plants. To compare values from each tuber sample, the specific gravity measurements are converted to reflect % total solids content of tubers. Percent total solids is calculated as (specific gravity)×(199.63)−194.84 (Porter, et al., Am. Pot. J. (1964) 41:329–336). Differences are detected in percent total solids as determined for tubers from several of the glgA transformed plants as compared to tubers from control plants.

Results are presented in Table 1 which represent average specific gravity of tubers of 5 replicate plants, except as otherwise indicated. Specific gravity measurements are determined for three to five uniformly sized tubers from each plant and the measurements of the tubers from the replicate plants are then averaged to determine average specific gravity (SpGr) of tubers for each transformation event. Values for one set of transformed control plants (Tx) and one set of untransformed/regenerated control plants (Rg) for each construct are shown at the top of their respective columns. Transformed control plants are transformed with a non-carbohydrate-related gene.

TABLE 1

Average Specific Gravity Measurements

| Event | SpGr | Event | SpGr |
|---|---|---|---|
| Controls | | Controls | |
| Tx | 1.079 | Tx | 1.083 |
| Rg | 1.081 | *Rg | 1.077 |
| Transformed Plants | | Transformed Plants | |
| 1457-3 | 1.073 | 1457B-3 | 1.062 |
| 1457-4 | 1.060 | 1457B-4 | 1.075 |
| 1457-6 | 1.076 | 1457B-5 | 1.073 |
| 1457-7 | 1.080 | 1457B-7 | 1.066 |
| 1457-8 | 1.077 | 1457B-8 | 1.066 |
| 1457-9 | 1.067 | 1457B-9 | 1.063 |
| 1457-10 | 1.083 | 1457B-10 | 1.075 |
| 1457-11 | 1.065 | 1457B-12 | 1.065 |
| 1457-12 | 1.066 | 1457B-13 | 1.058 |
| 1457-13 | 1.080 | *1457B-15 | 1.053 |
| 1457-14 | 1.062 | 1457B-16 | 1.075 |
| 1457-15 | 1.064 | 1457B-17 | 1.053 |
| 1457-16 | 1.068 | 1457B-18 | 1.068 |
| 1457-17 | 1.069 | 1457B-21 | 1.081 |
| 1457-18 | 1.060 | 1457B-22 | 1.067 |
| 1457-19 | 1.069 | 1457B-23 | 1.069 |
| 1457-20 | 1.066 | 1457B-24 | 1.068 |
| 1457-22 | 1.068 | | |

*Only 4 replicate plants are available for these samples.

It is readily apparent from the data presented in Table 1 that transgenic plants are obtained which produce tubers having an altered specific gravity as compared to the tubers from control plants.

Statistical analysis is conducted on the specific gravity measurements of tubers from the 5 replicates of one of the transformation events as compared to the specific gravity measurements of tubers from two control events. The event analyzed is 1457-4 which has an average specific gravity of 1.060. The specific gravity measurements of tubers from the individual replicates that are used to calculate the average for this event are 1.059, 1.057, 1.067, 1.066, and 1.053. The specific gravity measurements for replicates of control tubers are as follows. Tx (ave. 1.079): 1.076, 1.082, 1.073, 1.083, and 1.079. Rg (ave. 1.081): 1.076, 1.087, 1.083, 1.082, and 1.077. These measurements are converted to percent solids as described above and the percent solids values are used for statistical analysis as follows.

A comparison of sample means is conducted on the percent solids values calculated for the three events, 1457-4, Tx and Rx, by calculating the t value (Student's t) and determining statistical difference based on a standard table of values for t. (See, for example, Steel and Torrie (1980) *Principles and Procedures of Statistics: A Biometrical Approach* (McGraw-Hill pub.) Chapter 5 and Table A.3). These analyses indicate a significant difference between the average specific gravity measurements of transgenic tubers as compared to control tubers at a confidence level of greater than 99%. The average specific gravity measurements of the two control groups are not significantly different.

Further analysis may be conducted on tubers from selected pCGN1457 and pCGN1457B transformed plants and from non-transformed controls (RB-43) to determine starch content, amylose percentages and to elucidate chain length distribution in the amylopectin component of the starch. Starch granules are isolated as described by Boyer et al. (1976) *Cereal Chemistry* 53:327–337) and starch content estimated on a weight basis (starch wt/fresh wt). Amylose percentages are determined by gel-filtration analysis (Boyer et al. (1985) *Starch/Starke* 37:73–79). Chain length distribution patterns are determined by HPLC analysis as described by Sanders et al. (1990) *Cereal Chemistry* 67:594–602). Amylopectins are characterized by the ratios (on a weight basis) of low molecular weight chains to high molecular weight chains as described by Hizukuri (*Carbohydrate Research* (1985) 141:295–306). Results of these analyses are presented in Table 2.

TABLE 2

Analyses of Trangenic Potato Tuber Starch

| Construct | Spec. Gravity | % Starch | % Amylose | % High M.W. Chains | % Low M.W. Chains | Low M.W./ High M.W. |
|---|---|---|---|---|---|---|
| RB-43 | 1.081 | 17.1 | 23 | 33 | 66 | 2.0 |
| 1457-4 | 1.060 | 11.0 | 12 | 20 | 80 | 4.0 |
| 1457-17 | 1.069 | 14.6 | 24 | 28 | 72 | 2.6 |
| 1457-18 | 1.060 | 11.8 | 8 | 15 | 85 | 5.7 |
| RB-43 | 1.077 | 17.2 | 27 | | | |
| 1457B-15 | 1.053 | 9.0 | 9 | 15 | 85 | 5.7 |
| 1457B-17 | 1.053 | 12.5 | 19 | 26 | 84 | 3.2 |

The data presented in Table 2 indicate that tubers, from transgenic plants which have an altered specific gravity, also have altered starch. In particular, the percentage of amylose in the transgenic potato tubers is decreased. In addition, the amylopectin portion of the starch from transgenic potato tubers has more low molecular weight chains and less high molecular weight chains than wild type potato tuber amylopectin, thus indicating that the amylopectin from transgenic tubers has more branch points.

It is evident from the above results, that plant cells and plants can be produced which have improved properties or may produce a desired product. In accordance with the subject invention, it is now seen that glycogen biosynthesis enzyme sequences may be introduced into a plant host cell and be used to express such enzyme or enzymes or to modify native starch precursors. Moreover, it is seen that such enzymes demonstrate biological activity on plant starch precursors resulting in a demonstrable phenotype in planta, namely altered specific gravity. In addition, the activity of glycogen biosynthetic enzymes in plants has been shown to result in starch having altered properties, in particular altered ratios of amylose/amylopectin and altered distribution of low molecular weight chain lengths to high molecular weight chain lengths in the amylopectin fraction. In this manner, plants, including plant cells and plant parts, having modified starch properties may be obtained, wherein the modified starch has unique and desirous properties.

In order to demonstrate the use of starch degradation product enzymes to produce CGT compounds in accordance with the present invention, the following examples demonstrate the creation of CGT structural gene constructs and the transfer of such constructs into plant expression systems.

EXAMPLE 7

Cloning the CGT Coding Region

This example describes the isolation of the coding region for a cyclodextrin glycosyltransferase (CGT) gene from *Klebsiella pneumoneae* and the engineering of the coding region for subsequent cloning.

Total genomic DNA is prepared from *Klebsiella pneumoneae* M5A1 (Binder et al., *Gene* (1986) 47:269–277) by growing a 5 ml culture in ECLB (Maniatis, T. et al., *Molecular Cloning: A Laboratory Manual*, Cold Spring Harbon, N.Y. (1982)) overnight at 37° C. The bacteria are pelleted by centrifugation for 10 minutes at 4500×g, the supernatant is discarded, and the pellet is resuspended in 2.5 ml of 10 mM Tris, 1 mM EDTA buffer. To this suspension is added 500 µl of a 5 mg/ml Pronase® protease (Calbiochem Brand Biochemials; La Jolla, Calif.) solution and 2 ml of 2% lauryl sulfate, sodium salt (Sigma; St. Louis, Mo.), with gentle mixing and the suspension is incubated at 37° C. for 50 minutes. A clear solution indicates that the bacteria have lysed. The solution is then extracted with 5 ml phenol, then 5 ml phenol:chloroform:isoamyl alcohol (25:24:1:), followed by 5 ml chloroform. Nucelic acids are precipitated from the aqueous phase with 1/10 volume of 3M sodium acetate and two volumes of 100% ethanol, and the tube is incubated at room temperature for 1 hour. Nucleic acids are removed from solution and resuspended in 1 ml water. A second ethonol precipitation is preformed and the nucleic acids are resuspended in 200 µl of 10 mM Tris, 1 mM EDTA buffer.

Oligonucleotide probes flanking the 2 kb cyclodextrin glycosyltransferase (EC 2.4.1.19) gene of *K. pneumoneae* (Bender, H., *Arch. Microbiol.* (1977) 111:271–282) and containing restriction sites for BamHI and SalI are synthesized on an Applied Biosystems 380A DNA synthesizer (Foster City, Calif.) in accordance with the manufacturer's instructions. Specifically the probes are:

```
                  BamHI
str3:  5'ATATAGGATCCATTAGGACTAGATAATGAAAAGAA 3'
(SEQ ID NO: 3)

SalI
str:4  5'AATAAGTCGACTTTTAATTAAAACGAGCCATTCGT 3'
(SEQ ID NO: 4)
```

The nucleic acid preparation of *K. pneumoneae* is treated with RNAse and the DNA is used as a template in a polymerase chain reaction (PCR) with str3 and str4 as primers. A Perkin-Elmer/Cetus (Norwalk, Conn.) thermal cycler is used with the manufacturer's reagents and in accordance with the manufacturer's instructions. The reaction mixture contains 41.5 µl $H_2O$, 10 µl 10×Reaction buffer, 16 µl dNTP's (1.25 mM dCTP, dATP, dGTP & dTTP], 5 µl str3 (20 mM), 5 µl str4 (20 mM), 22 µl total *K. pneumoneae* DNA (0.05 µg/µl) and 0.5 µl Taq polymerase. The reaction is performed for 15 cycles with melting (denaturation) for 1 minute at 94° C., annealing (hybridization) for 2 minutes at 37° C. and chain elongation for 3 minutes at 72° C. The reaction is then performed for an additional 10 cycles with melting for 1 minute at 94° C., annealing or 2 minutes at 37° C. and chain elongation at 72° C. for 3 minutes 15 seconds initially and increasing the time by 15 seconds each cycle so that the last cycle is 5 minutes 45 seconds.

The resulting PCR product fragments (~2 kb) are digested with SalI and BamHI and ligated into a SalI and BamHI digest of pCGN65α3X (see below). Transformed *E. coli* DH5α cells (BRL; Gaithersburg, Md.) containing pCGN65α3X are screened on 1% starch plates (ECLB+1% starch) by flooding with $I_2$/KI and evaluating for clearing of starch from around the edge of the colony.

Clone 1 exhibited a good zone of clearing and is digested with SphI and SalI, ligated into SphI- and SalI-digested pUC19 (Norrander et al., *Gene* (1983) 26:101–106) and Yanisch-Perron et al., *Gene* (1985) 33:103–119), yielding the plasmid pCGT2 (~4.5 kb). Sequence analysis of pCGT2 (FIG. 4A and SEQ ID NO:15) showed six single base changes randomly distributed throughout the CGT gene (99.7% homology) which resulted in three amino acid changes (FIG. 4B and SEQ ID NOS: 16, 18, 20). Plasmid pCGT2 was digested with SphI, treated with the Klenow fragment of DNA polymerase I (Klenow fragment) to generate blunt ends and to ligate in a BglII linker. The resulting plasmid, pCGT4, was sequenced using the Sequenase® DNA sequencing kit (U.S. Biochemical; Cleveland, Ohio) in accordance with the manufacturer's instructions to confirm the correct reading frame:

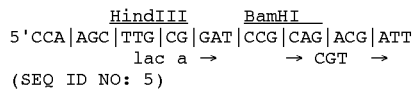

```
          HindIII      BamHI
5'CCA|AGC|TTG|CG|GAT|CCG|CAG|ACG|ATT
         lac a →         → CGT →
(SEQ ID NO: 5)
```

Construction of pCGN65α3X

Plasmid pUC18 (Yanisch-Perron et al., (1985) supra) is digested with HaeII to release the lacZ' fragment, treated with Klenow fragment to create blunt ends, and the lacZ'-containing fragment is ligated into pCGN565RB-H+X (see below), which has been digested with AccI and SphI, and treated with Klenow fragment, resulting in plasmid pCGN565RBα3X. In pCGN565RBα3X, the lac promoter is distal to the T-DNA right border. Both clones are positive for lacZ' expression when plated on an appropriate host. Each clone contains coordinates 13990–14273 of the T-DNA right border fragment (Barker et al., *Plant mol. Biol.* (1983) 2:335–350), having deleted the AccI-SphI fragment (coordinates 13800–13989). The 728 bp BglII-XhoI fragment of pCGN565RBα3X, containing the T-DNA right border piece and the lacZ' gene, is cloned into BglII- and XhoI-digested pCGN65ΔKX-S+X to replace the BglII-XhoI right border fragment of pCGN65ΔKX-S+X and create pCGN65α3X. The construction of pCGN65α3X is described in detail in co-pending U.S. application Ser. No. 07/382,176, filed Jul. 19, 1989.

Construction of PCGN565RB-H+X

Plasmid pCGN451 includes an octopine cassette which contains approximately 1556 bp of the 5' non-coding region fused, via an EcoRI linker, to the 3' non-coding region of the octopinel synthase gene of pTiA6. The pTi coordinates are 11,207 to 12,823 for the 3' region and 13,643 to 15,208 for the 5' region (Barker et al., (1983) supra). Plasmid pCGN451 is digested with HpaI and ligated in the presence of synthetic SphI linker DNA to generate pCGN55. The XhoI-SphI fragment of pCGN55 (coordinates 13800–15208, including the right border of *Agrobacterium tumefaciens* T-DNA (Barker et al., *Gene* (1977) 2:95–113) is cloned into SalI- and SphI-digested pUC19 (Yanisch-Perron et al., (1985) supra) to create pCGN60. The 1.4 kb RindIII-BamHI fragment of pCGN60 is cloned into HindIII- and BamHI-digested with pSP64 (Promega, Inc.) to generate pCGN1039. Plasmid pCGN1039 is digested with SmaI and NruI (deleting coordinates 14273–15208 (Barker et al., (1977) supra) and ligated in the presence of synthetic BglII linker DNA to create pCGN1039ΔNS. The 0.47 kb EcoRI-HindIII fragment of pCGN1039ΔNS is cloned into EcoRI- and HindIII-digested pCGN565 to create pCGN565RB. The HindIII site of pCGN565RB is replaced with an XhoI site by HindIII digestion, treatment with Klenow fragment, and ligation in the presence of synthetic XhoI linker DNA to create pCGN565RB-H+X.

EXAMPLE 8

Plastid Translocating Sequences

This example describes the preparation of DNA sequences encoding transit peptides for use in the delivery of a CGT gene to starch-containing organelles.

Construction of SSU+aroA Transit Peptide

Plasmid pCGN1132 contains a 35S promoter-ribulosebisphosphate carboxylase small subunit (5'-35S-SSU) leader plus 48 bp of mature small subunit (SSU) protein from pea aroA sequence (the gene locus which encodes 5-enolpyruvyl-3-phosphoshikimate synthetase (EC 2.5.1.19)). It is prepared from pCGN1096, a plasmid containing a hybrid SSU protein gene, which carries DNA encoding mature SSU protein from pea, and SstI and EcoRI sites 3' of the coding region (used in the preparation of pCGN1115, a plasmid having a 5'-35S-SSU+48-aroA-tml-3' sequence, and pCGN1129, a plasmid having a 35S promoter in a chloramphenicol resistance gene (Cam') backbone).

Construction of pCGN1096

The aroA moiety of pCGN1077 is removed by digestion with SphI and SalI. In its place is cloned the region coding for the mature pea SSU protein, as an SphI-PstI fragment, which is then excised with SphI and SalI. The resulting plasmid, pCGN1094, codes for a hybrid SSU protein having the transit peptide of the soybean clone, and the mature portion of the pea clone and carrier SstI and EcoRI sites 3' of the coding region. The HindIII to BamHI region of transposon Tn6 (Jorgensen et al., *Mol. Gen. Genet.* (1979) 177:65) encoding the kanamycin resistance gene (Kan') is cloned into the same sites of pBR322 (Bolivar et al., *Gene* (1977) 2:95–133) generating pDS7. The BglII site 3' of the Kan' gene is digested and filled in with the large fragment of *E. coli* DNA polymerase 1 and deoxy-nucleotides triphosphate. An SstI linker is ligated into the blunted site, generating plasmid pCGN1093. Plasmid pPMG34.3 is digested with SalI, the site filled in as above and EcoRI linkers are ligated into the site resulting in plasmid pCGN1092. The latter plasmid is digested with SstI and SmaI and the Kan' gene excised from pCGN1093 with SstI and SmaI is ligated in, generating pCGN1095. The Kan' and aroA genes are excised as a piece from pCGN1095 by digestion with SstI and EcoRI and inserted into the SstI and EcoRI sites of pCGN1094, producing pCGN1096. Summarizing, pCGN1096 contains (5'->3') the following pertinent features: The SSU gene—a polylinker coding for PstI, SalI, SstI, and KpnI—the Kan' gene—SmaI and BamHI restriction sites—the aroA gene without the original ATG start codon. The construction of pCGN1096 is also described in detail in co-pending U.S. application Ser. No. 06/097,498, filed Sep. 16, 1987.

Plasmid pCGN1096 is digested to completion with SalI and then digested with exonuclease Bal31 (BRL; Gaithersburg, Md.) for 10 minutes, thus deleting a portion of the mature SSU gene. The resulting plasmid is then digested with SmaI to eliminate the Kan' gene and provide blunt ends, recircularized with T4 DNA ligase and transformed into *E. coli* LC3 (Comai et al., *Science* (1983) 221:370–371), an aroA mutant. DNA isolated from aroA$^+$ and Kan' colonies is digested with BamHI and SphI and ligated with BamHI- and SphI-digested M13mp18 (Norrander et al., *Gene* (1983) 26:101–106 and Yanisch-Perron et al., *Gene* (1985) 33:103–119) DNA for sequencing. Clone 7 has 48 bp of the mature SSU gene remaining (SEQ ID NO: 1), and the 3' end consists of phe-glu-thr-leu-ser. Clone 7 is transformed into *E. coli* strain 71-18 (Yanisch-Perron et al. (1985) supra) and DNA isolated from transformants is digested with SphI and ClaI to remove the 0.65 kb fragment containing the 48 bp of mature protein and the 5' end of the aroA gene. Plasmid pCGN1106 (Comai et al., *J. Biol. Chem.* (1988) 263:15104–15109) is also digested with SphI and ClaI and the 6.8 kb isolated vector fragment is ligated with the 0.65 kb fragment of clone 7 to yield pCGN1115 (5'-35S-SSU+48-aroA-tml-3').

The 7.2 kb plasmid pCGN1180 (35S-SSU+70-aroA-ocs3') (Comai et al. (*1988*) supra) and the 25.6 kb plasmid pCGN594 (Houck, et al., *Frontiers in Applied Microbiology* (1990) 4:1–17) (LB-Gent^r-ocs5'-Kan^r-ocs3'-RB) (construction of pCGN594 is described in co-pending U.S. application Ser. No. 07/382,802, filed Jul. 19, 1989) are digested with HindIII and ligated together to yield the 32.8 kb plasmid pCGN1109 (LB-Gent^r-35S-SSU+70-aroA-ocs3'-ocs5'-Kan^r-ocs3'-RB).

Plasmid pCGN1109 is digested with EcoRI to delete an internal 9.1 kb fragment containing the SSU leader plus 70 bp of the mature SSU gene, the aroA gene and its ocs3' terminator, the Amp^r backbone from pCGN1180 and ocs5'-Kan^r-ocs3' from pCGN594. The EcoRI digest of pCGN1109 is then treated with Klenow fragment to blunt the ends, and a XhoI linker (dCCTCGAGG) (New England Biolabs Inc.; Beverly, Mass.) is ligated in, yielding pCGN1125 (LB-35S-RB).

Plasmid pCGN1125 is digested with HindIII and BglII to delete the 0.72 kb fragment of the 35S promoter. This digest is ligated with HindIII- and BamHI-digested Cam^r vector, pCGN786. Plasmid pCGN786 is a chloramphenicol resistant pUC based vector formed by insertion of a synthetic linker containing restriction digest sites EcoRI, SalI, BglII, PstI, XhoI, BamHI, and HindIII into pCGN566 (pCGN566 contains the EcoRI-HindIII linker of pUC18 inserted into the EcoKI-HindIII sites of pUC13-cm (K. Buckley (1985) Ph.D. thesis, University of California at San Diego). The resulting 3.22 kb plasmid, pCGN1128, contains the 35S promoter with a 3' multilinker in a Cam^r backbone.

Plasmid pCGN1128 is digested with HindIII, treated with Klenow fragment to blunt the ends and ligated with BglII linkers to yield pCGN1129, thus changing the HindIII site located 5' to the 35S promoter into a BglII site.

Plasmid pCGN1115 is digested with SalI to removed a 1.6 kb fragment containing the SSU leader plus 48 bp of the mature SSU gene and the aroA gene. An XhoI digest of pCGN1129 opened the plasmid 3' to the 35S promoter. Ligation of these two digests yielded the 4.8 kb plasmid pCGN1132, containing 5'-35S-SSU leader plus 48 bp of mature SSU-aroA. Plasmid pCGN1132 is digested with EcoRI, treated with Klenow fragment to form blunt ends, and ligated with SacI linkers (d(CGAGCTCG) New England Biolabs Inc.; Beverly, Mass.) to yield pCGN1132S, thus changing the EcoRI site 3' to the aroA gene to a SacI site.

Transit Peptide+Cyclodextrin Glycosyltransferase Gene

Plasmid pCGT4 (See Example 7) and pCGN1132S are digested with BamHI and SalI and ligated together. The resulting plasmid pCGT5 contains 5'-35S-SSU+48-CGT-3'.

EXAMPLE 9

Cloning of Patatin Regulatory Regions and Preparation of Patatin-5'-nos-3' Expression Cassettes This example describes the cloning of patatin-5' regulatory regions from two potato varieties and the preparation of patatin-5'-nos-3' expression cassettes pCGN2143 and pCGN2144. Also provided is the cloning of patatin-3' regulatory regions and the preparation of patatin-5'-patatin-3' expression cassettes pCGN2173 and pCGN2174.

Genomic DNA is isolated from leaves of *Solanum tuberosum* var. *Russett Burbank* and var. *Kennebec* as described in Dellaporta et al., *Plant Mol. Biol. Reporter* (1983) 1(4) :19–21, with the following modifications: Approximately 9 g fresh weight of leaf tissue is ground, a polytron grinding is not performed and in the final step the DNA is dissolved in 300 μl of 10 mM Tris, 1 mM EDTA, pH 8. A synthetic oligonucleotide, pat1, containing digestion sites for NheI, PstI and XhoI with 24 bp of homology of the 5'-region of a 701 bp fragment (coordinates 1611 to 2312) 5' to a class I patatin gene, isolated from *Solanum tuberosum* var. *Maris Piper* (Bevan et al., *NAR* (1986) 14:4625–4638) is synthesized (Applied BioSystems 380A DNA synthesizer): pat1:

```
            NheI     PstI      XhoI
5'CAGCAGGCTAGCTCGCTGCAGCATCTCGAGATTTGTCAAATCAGGCTCAAAGATC3'
            (SEQ ID NO: 6)
```

A second synthetic oligonucleotide, pat2, containing digestion sites for BamHI and SpeI with 25 bp of homology to the 3' region of the 701 bp piece is also synthesized: pat2:

```
            BamHI      SpeI
5'ACGACGGGATCCCATACTAGTTTTGCAAATGTTCAAATTGTTTTT3'
            (SEQ ID NO: 7)
```

Using the genomic potato DNA as a template, and pat1 and pat2 as primers, a polymerase chain reaction (PCR) is performed in a Perkin-Elmer/Cetus thermal cycler with the manufacturer's reagents and in accordance with the manufacturer's instructions. The reaction contains 62.5 μl H$_2$O, 10 μl 10×Reaction buffer, 16 μl dNTP's (1.25 mM dCTP, dATP, dGTP & dTTP], 5 μl pat1 (20 mM), 5 μl pat2 (20 mM), 1 μl potato genomic DNA (3 μg/μl), 0.5 μl Taq polymerase. The PCR is performed for 25 cycles with melting for 1 minute at 94° C., annealing for 2 minutes at 37° C. and chain elongation for 3 minutes at 72° C. The resulting PCR product fragments (approximately 700 bp) are digested with NheI and BamHI. Plasmid pCGN1586N (5'-D35S-TMVΩ-nos'3'; pCGN1586 (described below) having a NheI site 5' to the 35S region) is digested with NheI and BamHI to delete the D35S-Ω' fragment. Ligation of NheI-BamHI digested pCGN1586N, which contains the nos-3' region, and the PCR fragments yield a patatin-5'-nos-3' cassette with SpeI, BamHI, SalI and SstI restriction sites between the 5' and 3' regions for insertion of a DNA sequence of interest.

The 5' regions of two clones, designated pCGN2143 and pCGN2144, are sequenced. Plasmid pCGN2143 has a Kennebec patatin-5' region that is 702 bp in length and 99.7% homologous to the native sequence (as reported by Bevan (1986) supra) (SEQ ID NO: 2). The 5' region of pCGN2144, from Russet Burbank, is 636 bp in length, containing a 71 bp deletion from coordinate 1971 to coordinate 2040. The remainder of the Russet Burbank clone is 97.0% homologous to the native sequence (as reported by Bevan (1986) supra) (SEQ ID NO: 3) (SEQ ID NO: 30).

A synthetic oligonucleotide, pat3S, with 24 bp of homology to the 5' region of a 804 bp region 3' to a class I patatin gene (Bevan 5000 to 5804): pat3S:

```
            SstI
5'CAGCAGGAGCTCGTACAAGTTGGCGAAACATTATTG3'
            (SEQ ID NO:4)
``` is synthesized. This oligonucleotide contained a restriction enzyme site for SstI. A second oligonucleotide, pat4, with 24 bp of homology to the 3' region of the 804 bp region is also synthesized: pat4:

```
                NheI      XhoI      PstI
5'ACGACGGCTAGCTCGCTCGAGCATCTGCAGTGCATATAAGTTCACATTAATATG3'
(SEQ ID NO:5)
```

It contains digestion sites for the enzymes NheI, XhoI and PstI.

Using Russet Burbank genomic potato DNA as a template, a polymerase chain reaction (PCR) as described above is performed for 25 cycles with melting for 1 minute at 94° C., annealing for 2 minutes at 42° C. and chain elongation for 3 minutes at 72° C. A Perkin-Elmer/Cetus thermal cycler is used with the manufacturer's reagents and in accordance with the manufacturer's instructions. Specifically, the reaction contained 53.5 μl H₂O, 10 μl synthetic BglII linkers (d(pCAGATCTG) New England Biolabs Inc.; Beverly, Mass.) are ligated in. A total of three BglII linkers are ligated into the EcoRI site creating two PstI sites. The resulting plasmid, termed pCGN1579 (D35S-nos-3'), has a 3' polylinker, consisting of 5'-EcoRI, BglII, PstI, BglII, PstI, BglII, EcoRI-3'.

A tobacco Mosaic Virus omega' (TMVΩ') region (Gallie et al., NAR (1987) 15(21):8693–8711) with BglII, NcoI, BamHI, SalI and SacI restriction sites:

```
              BglII
5'CAGGAGATCTTATTTTTACAACAATTACCAACAACCAACAAACAACAACAACATTACAAT
TACTATT TACAATTACACCATGGATCCGTCGACGAGCTC3'
                        NcoI BamHI SalI  SacI
(SEQ ID NO: 10)
```

10×reaction buffer, 16 μl dNTP's [1.25 mM dCTP, dATP, dGTP & dTTP], 5 μl pat3S (20 mM), 5 μl pat4 (20 mM), 10 μl genomic potato DNA (3 μg/μl), 0.5 μl Taq polymerase. The resulting approximately 800 bp PCR product fragments are digested with NheI and SstI and ligated into pCGN1586N (see below). Sequencing of one clone, designated pCGN2159, showed that the 3' fragment is 823 bp in length and 93.6% homologous to Bevan's reported sequence (Bevan (1986) supra).

Cloning of the Patatin Cassettes pCGN2173 and pCGN2174

A patatin cassette consisting of the 5' patatin region from Kennebec and 3' patatin region from Russet Burbank, identified as pCGN2173, is constructed by a three way ligation of the following fragments: The NheI to SstI Kennebec 5' patatin fragment of pCGN2143 (see above), the SstI to NheI Russet Burbank 3' patatin fragment of pCGN2159 and the NheI to NheI pUC backbone of pCGN1599.

A second patatin cassette, identified as pCGN2174, is constructed by a three way ligation of the NheI to SstI Russet Burbank 5' patatin fragment of pCGN2144 (see above), the SstI to NheI Russet Burbank 3' patatin fragment of pCGN2159 and the NheI to NheI pUC backbone of pCGN1599.

Construction of pCGN1586/1586N

Plasmid pCGN2113 (6.1 kb) contains a double-35S promoter (D35S) and the tml-3' region with multiple cloning sites between them, contained in a pUC-derived plasmid backbone bearing an ampicillin resistance gene (Amp^r). The promoter/tml cassette is bordered by multiple restriction sites for easy removal. Plasmid pCGN2113 is digested with EcoRI and SacI, deleting the 2.2 kb tml-3' region. Plasmid pBI221.1 (Jefferson, R. A., Plant Mol. Biol. Reporter (1987) 5:387–405) is digested with EcoRI and SacI to delete the 0.3 kb nos-3' region. The digested pCGN2113 and pBI221.1 DNAs are ligated together, and the resultant 4.2 kb recombinant plasmid with the tml-3' of pCGN2113 replaced by nos-3' is designated pCGN1575 (5'-D35S-nos-3').

Plasmid pCGN1575 is digested with SphI and XbaI, blunt ends generated by treatment with Klenow fragment, and the ends are ligated together. In the resulting plasmid, pCGN1577, the Sph, PstI, SalI and XbaI sites 5' of the D35S promoter are eliminated.

Plasmid pCGN1577 is digested with EcoRI, the sticky ends blunted by treatment with Klenow fragment, and is synthesized on a Applied Biosystems® 380A DNA synthesizer and digested with BglII and SacI. Plasmid pCGN1577 is digested with BamHI and SacI and the synthetic TMVΩ' is ligated in between the 5'-D35S and nos-3' regions. The resulting plasmid is designated pCGN1586 (5'-D35S-TMVΩ'-nos'3'). Plasmid pCGN1586N is made by digesting pCGN1586 with HindIII and filling in the 5' overhang with Klenow fragment, thus forming a NheI site 5' to the D35S region.

EXAMPLE 10
Preparation of Patatin-5'-CGT-Nos-3' Binary Vectors

This example describes the construction of binary vectors containing: (1) the patatin-5' region from either *Solanum tuberosum* var. *Kennebec* or var. *Russet Burbank*, (2) DNA encoding a transit peptide from soybean RuBisCo SSU protein, (3) 48 bp of DNA encoding 16 amino acids of mature RuBisCo SSU protein from pea, (4) the CGT coding region from *Klebsiella pneumoneae*, and (5) the nos-3' region.;

Plasmid pCGN2143 prepared as described in Example 9 is digested with SpeI and SstI, opening the plasmid between the patatin-5' region and nos-3' region. Plasmid pCGT5 (see Example 8) is digested with XbaI and SstI and ligated with pCGN2143 to yield pCGN2151. Plasmid pCGN2151 consists of 5'-Kennebec patatin-SSU+48-CGT-nos3'. Plasmid pCGN2151 is digested with PstI and ligated with PstI-digested pCGN1558 (see below). This yields the binary vectors pCGN2160a and pCGN2160b.

In pCGN2160a, the 5'-patatin-SSU+48 bp-CGT-nos 3' is inserted into pCGN1558 such that it transcribes in the opposite direction as the 35S-Kan^r-tml gene. In pCGN2160b, the 5'-patatin-SSU+48 bp-CGT-nos-3' is inserted into pCGN1558 such that it transcribes in the same direction as the 35S-Kan^r-tml gene.

Plasmid pCGN2144 is digested with SpeI and SstI, opening the plasmid between the patatin-5' and nos-3' regions. Plasmid pCGT5 is digested with XbaI and SstI and ligated with pCGN2144 to yield pCGN2152. Plasmid pCGN2152 consists of 5'-Russet Burbank patatin-SSU+48-CGT-nos3'. Plasmid pCGN2152 is digested with PstI and ligated with pCGN1558 (see below) digested with PstI. This yields the binary vectors pCGN2161a and pCGN2161b. In pCGN2161a, the 5'-patatin-SSU+48 bp-CGT-nos3' is inserted into pCGN1558 such that it transcribes in the opposite direction as the 35S-Kan$^r$-tml gene. In pCGN2161b, the 5'-patatin-SSU+48 bp-CGT-nos-3' is inserted into PCGN1558 such that it transcribes in the same direction as the 35S-Kan$^r$-tml gene.

Construction of pCGN1558

Plasmid pCGN1558 (McBride and Summerfelt, *Plant Mol. Biol.* (1990) 14(27):269–276) is a binary plant transformation vector containing the left and right T-DNA borders of *Agrobacterium tumefaciens* octopine Ti-plasmid pTiA6 (Currier and Nester, *J. Bact.* (1976) 126:157–165), the gentamicin resistance gene (Gen$^r$) of pPH1JI (Hirsch and Beringer, *Plasmid* (1984) 12:139–141) an *Agrobacterium rhizogenes* Ri plasmid origin of replication from pLJbB11 (Jouanin et al., *Mol. Gen. Genet.* (1985) 201:370–374), a 35S promoter-Kan$^r$-tml-3' region capable of conferring kanamycin resistance to transformed plants, a ColE1 origin of replication from pBR322 (Bolivar et al. (1977) supra) and a lacZ' screenable marker gene from pUC18 (Yanish-Perron et al. (1985) supra). The construction of pCGN1558 is described in co-pending U.S. application Ser. No. 07/494,722, filed Mar. 16, 1990.

EXAMPLE 11

Preparation of Transgenic Plants

This example describes the transformation of *Agrobacterium tumefaciens* with a CGT gene DNA construct in accordance with the present invention and the co-cultivation of such *A. tumefaciens* with plant cells to transform host cells and enable the resultant plants to produce cyclodextrins.

Transformation of *Agrobacterium tumefaciens*

Cells of *Agrobacterium tumefaciens* strain 2760 (also known as LBA4404, Hoekema et al., *Nature* (1983) 303:179–180) are transformed with binary vectors, such as pCGN2160a, pCGN2160b, pCGN2161a and pCGN2161b (as described in Example 10) using the method of Holsters et al. (*Mol. Gen. Genet.* (1978) 163:181–187). The transformed *A. tumefaciens* are then used in the co-cultivation of plants, in order to transfer the CGT construct into an expression system.

The Agrobacterium are grown in AB medium (per liter: 6 g $K_2HPO_4$, 2.3 g. $NaH_2PO_4 \cdot H_2O$, 2 g $NH_4Cl$, 3 g KCl, 5 g glucose, 2.5 mg $FeSO_4$, 246 mg $MgSO_4$, 14.7 mg $CaCl_2$, 15 g agar) plus 100 µg/L gentamicin sulfate and 100 µg/L streptomycin sulfate for 4–5 days. Single colonies are inoculated into 10 ml of MG/L broth (per liter: 5 g mannitol, 1 g L-Glutamic acid or 1.15 g sodium glutamate, 0.5 g $KH_2PO_4$, 0.10 g NaCl, 0.10 g $MgSO_4 \cdot 7H_2O$, 1 µg biotin, 5 g tryptone, 2.5 g yeast extract; adjust pH to 7.0) and are incubated overnight in a shaker at 30° C. and 180 rpm. Before co-cultivation, the Agrobacterium culture is centrifuged at 12,000×g for 10 minutes and resuspended in 20 ml MS medium (#510-1118, Gibco; Grand Island, N.Y.).

Cocultivation with Potato Cells

Feeder plates are prepared by pipetting 0.5 ml of a tobacco suspension culture (~$10^6$ cells/ml) onto 0.8% agar co-cultivation medium containing MS salts (#510-117, Gibco; Grand Island, N.Y.), 1.0 mg/L thiamine-HCl, 0.5 mg/L nicotinic acid, 0.5 mg/L pyridoxine-HCl, 30 g/L sucrose, 5 µM zeatin riboside, 3 µM 3-indoleacetyl-DL-aspartic acid, pH 5.9. The feeder plates are prepared one day in advance and incubated at 25° C. A sterile 3 mm filter paper disk is placed on top of the tobacco cells after they have grown for one day.

Tubers of *Solanum tubersoum* var. *Russet Burbank* and var. *Kennebec* between the age of 1 and 6 months post-harvest are peeled and washed in distilled water. All subsequent steps are carried out in a flow hood using sterile techniques. For surface sterilization, tubers are immersed in a solution of 10% commercial bleach (sodium hypochlorite) with 2 drops of Ivory® liquid soap per 100 ml for 10 minutes. Tubers are rinsed six times in sterile distilled water and kept immersed in sterile liquid MS medium (#1118, Gibco; Grand Island; N.Y.) to prevent browning.

Tuber discs (1–2 mm thick) are prepared by cutting columns of potato tuber with a 1 cm cork borer and slicing the columns to the desired thickness. Discs are placed into the liquid MS medium culture of the transformed *A. tumefaciens* containing the binary vector of interest ($1 \times 10^7 – 1 \times 10^8$ bacteria/ml) until thoroughly wetted. Excess bacteria are removed by blotting discs on sterile paper towels. The discs are co-cultivated with the bacteria for 48 hours on the feeder plates and then transferred to regeneration medium (co-cultivation medium plus 500 mg/L carbenicillin and 100 mg/L kanamycin). In 3 to 4 weeks, shoots develop from the discs.

When shoots are approximately 1 cm, they are excised and transferred to a 0.8% agar rooting medium containing MS salts, 1.0 mg/L thiamine-HCl, 0.5 mg/L nicotinic acid, 0.5 mg/L pyridoxine-HCl, 30 g/L sucrose, 200 mg/L carbenicillin and 100–200 mg/L kanamycin at pH 5.9. Plants are rooted two times with at least one rooting taking place on rooting medium with the higher level of kanamycin (200 mg/L). Plants which rooter twice are then confirmed as transformed by performing the NPTII blot activity assays (Radke, S. E. et al., *Theor. Appl. Genet.* (1988) 75:685–694). Plants which are not positive for NPII activity are discarded.

Northern Blot Analysis of Transformed Plants

Total RNA is isolated from 5 g of tuber tissue (as described by Logeman et al., *Anal. Biochem.* (1987) 163:16–20). Poly-(A)+RNA is purified over oligo(dT) cellulose (as described by Maniatis et al. (1982) supra). RNA denaturing gels are run and blotted (as described by Facciotti et al., *Bio/Technology* (1985) 3:241–246). Equivalent amounts of poly-(A)+RNA are run in each lane. A 1.9 kb BamHI fragment of pCGT4 containing the CGT gene is used as a probe in the hybridization. The fragment may be isolated from an agarose gel using the Gene Clean® Kit (Bio 101, Inc.; La Jolla, Calif.) in accordance with the manufacturer's instructions. Nick-translation and hybridization are performed (as described by Shewmaker et al., *Virology* (1985) 140:281–288 except that washes are at 55° C.). The washed blot is autoradiographed on Kodak® X-OMat AR X-ray film (Rochester, N.Y.) at −70° C.

An autoradiogram of Russet Burbank potatoes each transformed with one of pCGN2160a, pCGN2161a or pCGN2161b shows bands in each of the transformant sample lanes. The bands are 2.3 kb in size, corresponding to the size of CGT message RNA. There is no band present in the lane containing RNA from the untransformed control.

EXAMPLE 12

Recovery of Cyclodextrin from Plants

In this example, the recovery and detection of cyclodextrin in transgenic potato tubers is described.

Rooted plants transformed as described in Example 11 are transplanted from rooting medium to a growth chamber (21° C., 16 hour photoperiod with 250–300 µE/m$^2$/sec light intensity) in soil prepared as follows: For about 340 gallons, combine 800 lb 20/30 sand (approximately 14 cubic feet), 16 cubic feet FisonsO Canadian Peat Moss, 16 cubic feet #3 vermiculite, and approximately 4.5 lb hydrated lime in a Gleason® mixer. The soil is steamed in the mixer for two hours; the mixer mixes for about 15 seconds at interval of fifteen minutes over a period of one hour to ensure even heating throughout the soil. During and after the process of steaming, the soil reaches temperatures of at least 180° F. for one hour. The soil then sits in the mixer until the next day. At that time, hydrated lime is added, if necessary, to adjust the pH to range between 6.30 and 6.80.

The relative humidity of the growth chamber is maintained at 70–90% for 2–4 days, after which the humidity is maintained at 40–60%. When plants are well established in the soil, at approximately two weeks, they are transplanted into the greenhouse. Plants are grown in 6.5 inch pots in a soil mix of peat:perlite:vermiculite (11:1:9) at an average temperature of 24° C. day/12° C. night. Day length is approximately 12 hours and light intensity levels varied from approximately 600 to 1000 $\mu E/m^2/sec$.

Tubers are harvested from plants 14 weeks after transplant into the greenhouse. Immediately after harvest, tubers are washed, weighed and their, specific gravity determined. Three representative tubers from each transformant are peeled, rinsed in distilled water, chopped into approximately 0.5 cm cubes, quick frozen in liquid nitrogen, and stored at approximately −70° C. until assayed.

Extraction of Cyclodextrin

To prepare samples for chromatography, cubes of frozen tuber tissue are ground into a powder in a coffee mill (Krups®, Closter, N.J.). For each plant assayed, extracts from tubers are prepared as follows: Five grams of frozen potato powder are ground in a prechilled mortar and pestle with 5 ml 25% ethanol and then frozen at −70° C. for at least overnight. Samples are then centrifuged at 8500×g for 10 minutes, the supernatant transferred to a clean tube, and the ethanol removed by roto-evaporation for 1 hour.

The cyclodextrin is separated from the tissue samples in C18 SEP-PAK columns (Waters Chromatography Div.; Milford, Mass.), previously washed with 5 ml of 100% methanol, followed by 5 ml of 50% methanol, followed 5 ml of water prior to sample application. After the sample is applied, the cartridge is washed with 10 ml of distilled water to remove contaminants, and the cyclodextrins are removed with 0.75 ml of 100% methanol, discarding the first two drops. The sample is then roto-evaporated to dryness, and redissolved in 20 $\mu$l of 30% methanol.

Detection of Cyclodextrin

Thin layer chromatography (TLC) is performed as described by Szejtli (Szejtli, J., *Cyclodextrin Technology* (1988) pp. 20–22, Kluwer Academic Publishers, Boston). Samples are spotted on silicagel G plates (#01011, Analtech; Newark, Del.) and dried. The chromatogram is developed for approximately 3 hours to a height of 13–15 cm, with a n-butanol-ethanol-water (4:3:3) mixture. After drying, the plate is exposed to iodine vapor for 5–10 min. to visualize the chromatogram.

Positive controls of α-cyclodextrin (α-CD) and β-cyclodextrin (β-CD) are run alongside samples from transgenic tissue, and average Rf values for four plates are 0.39 for α-CD and 0.36 for β-CD. The α-CD band stained light violet, while the β-CD band stained yellow. Tuber tissue from 20 transformed plants is screened for the presence of α-CD and β-CD. Tissue of tubers from eight Russet Burbank plants (RB2160a-11, RB2160b-7, RB2160b-9, RB2161a-2, RB2161b-3, RB2161b-5, RB2161b-11) produced bands which stained the same color as the α-CD control bands and had similar Rf values. In addition to the putative α-CD bands, the tubers from two plants (RB2160b-7 and 2160b-9) produced bands with Rf values and color similar to the β-CD control band.

In accordance with one aspect of the subject invention, cyclodextrin can be produced by host plants by incorporation of a cyclodextrin glycosyltransferase structural gene together with the appropriate regulatory sequence. In addition, DNA sequences coding for cyclodextrin glycosyltransferase are provided which can be used for producing cyclodextrin, for example, in methods of the present invention. Thus, plants are grown which can produce cyclodextrin, in order to enhance the utility of the crop plants.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. An isolated polynucleotide sequence comprising the sequence set forth in SEQ ID NO:11.

2. An isolated polynucleotide sequence comprising a sequence encoding the polypeptide sequence set forth in SEQ ID NO:12.

3. A nucleic acid construct comprising a polynucleotide sequence as set forth in SEQ ID NO:11 and a transcriptional and translational initiation region functional in a plant cell.

4. A transformed plant cell comprising a polynucleotide sequence as set forth in SEQ ID NO:11.

5. A transformed plant comprising a polynucleotide sequence as set forth in SEQ ID NO:11.

6. A recombinant DNA construct comprising a nucleotide sequence wherein said sequence comprises the sequence set forth in SEQ ID NO:11.

7. A recombinant DNA construct comprising a nucleotide sequence wherein said sequence encodes the polypeptide sequence set forth in SEQ ID NO:12.

* * * * *

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: unknown
      (D) TOPOLOGY: unknown (ii) MOLECULE TYPE: protein (iii) HYPOTHETICAL: NO (xi) SEQUENCE DESCRIPTION: SEQ ID NO:1:

```
Phe Glu Thr Leu Ser
 1               5
```

(2) INFORMATION FOR SEQ ID NO:2:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:2:

```
CAGGAGATCT TATTTTTACA ACAATTACCA ACAACAACAA ACAACAAACA ACATTACAAT      60

TACTATTTAC AATTACACCA TGGATCCGTC GACGAGCTC                             99
```

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:3:

```
ATATAGGATC CATTAGGACT AGATAATGAA AAGAA                                 35
```

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:4:

```
AATAAGTCGA CTTTTAATTA AAACGAGCCA TTCGT                                 35
```

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:5:

```
CCAAGCTTGC GGATCCGCAG ACGATT                                           26
```

(2) INFORMATION FOR SEQ ID NO:6:

(i) SEQUENCE CHARACTERISTICS:
        (A) LENGTH: 55 base pairs (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:6:

CAGCAGGCTA GCTCGCTGCA GCATCTCGAG ATTTGTCAAA TCAGGCTCAA AGATC       55

(2) INFORMATION FOR SEQ ID NO:7:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:7:

ACGACGGGAT CCCATACTAG TTTTGCAAAT GTTCAAATTG TTTTT                  45

(2) INFORMATION FOR SEQ ID NO:8:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:8:

CAGCAGGAGC TCGTACAAGT TGGCGAAACA TTATTG                            36

(2) INFORMATION FOR SEQ ID NO:9:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:9:

ACGACGGCTA GCTCGCTCGA GCATCTGCAG TGCATATAAG TTCACATTAA TATG        54

(2) INFORMATION FOR SEQ ID NO:10:

(i) SEQUENCE CHARACTERISTICS:
      (A) LENGTH: 99 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO:10:

CAGGAGATCT TATTTTTACA ACAATTACCA ACAACAACAA ACAACAAACA ACATTACAAT  60

TACTATTTAC AATTACACCA TGGATCCGTC GACGAGCTC                          99

(2) INFORMATION FOR SEQ ID NO:11:

(i) SEQUENCE CHARACTERISTICS:
        (A) LENGTH: 1464 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (xi) SEQUENCE DESCRIPTION: SEQ ID NO:11:

```
GATCTAACAG GAGCGATAAT GCAGGTTTTA CATGTATGTT CAGAGATGTT CCCGCTGCTT      60
AAAACCGGCG GTCTGGCTGA TGTTATTGGG GCATTACCCG CAGCACAAAT CGCAGACGGC     120
GTTGACGCTC GCGTACTGTT GCCTGCATTT CCCGATATTC GCCGTGGCGT GACCGATGCG     180
CAGGTAGTAT CCCGTCGTGA TACCTTCGCC GGACATATCA CGCTGTTGTT CGGTCATTAC     240
AACGGGGTTG GCATTTACCT GATTGACGCG CCGCATCTCT ATGATCGTCC GGGAAGCCCG     300
TATCACGATA CCAACTTATT TGCCTATACC GACAACGTAT TGCGTTTTGC GCTGCTGGGG     360
TGGGTTGGGG CAGAAATGGC CAGCGGGCTT GACCCATTCT GGCGTCCTGA TGTGGTGCAT     420
GCGCACGACT GGCATGCAGG CCTTGCGCCT GCGTATCTGG CGGCGCGCGG GCGTCCGGCG     480
AAGTCGGTGT TTACTGGGCA CAACCTGGCC TATCAAGGCA TGTTTTATGC ACATCACATG     540
AATGACATCC AATTGCCATG GTCATTCTTT AATATTCATG GCTGGAATT CAACGGACAA      600
ATCTCTTTCC TGAAGGCCGG TCTGTACTAT GCCGATCACA TTACGGCGGT CAGTCCAACC     660
TACGCTCGCG AGATCACCGA ACCGCAGTTT GCCTACGGTA TGGAAGGTCT GTTGCAACAG     720
CGTCACCGTG AAGGGCGTCT TTCCGGCGTA CTGAACGGCG TGGACGAGAA AATCTGGAGT     780
CCAGAGACGG ACTTACTGTT GGCCTCGCGT TACACCCGCG ATACGTTGGA AGATAAAGCG     840
GAAAATAAGC GCCAGTTACA AATCGCAATG GGGCTTAAGG TTGACGATAA AGTGCCGCTT     900
TTTGCAGTGG TGAGCCGTCT GACCAGCCAG AAAGGTCTCG ACCTGGTGCT GGAAGCCTTA     960
CCGGGTCTTC TGGAGCAGGG CGGGCAGCTG GCGCTACTCG GCGCGGGCGA TCCGGTGCTG    1020
CAGGAAGGTT TCCTTGCGGC GGCAGCGGAA TACCCCGGTC AGGTGGGCGT TCAGATTGGC    1080
TATCACGAAG CATTTTCGCA TCGCATTATG GGCGGCGCGG ACGTCATTCT GGTGCCCAGC    1140
CGTTTTGAAC CGTGCGGCTT AACGCAACTT TATGGATTGA AGTACGGTAC GCTGCCGTTA    1200
GTGCGGCGCA CCGGTGGGCT TGCTGATACG GTTTCTGACT GTTCTCTTGA GAACCTTGCA    1260
GATGGCGTCG CCAGTGGGTT TGTCTTTGAA GATAGTAATG CCTGGTCGCT GTTACGGGCT    1320
ATTCGACGTG CTTTTGTACT GTGGTCCCGT CCTTCACTGT GGCGGTTTGT GCAACGTCAG    1380
GCTATGGCAA TGGATTTTAG CTGGCAGGTC GCGGCGAAGT CGTACCGTGA GCTTTACTAT    1440
CGCTCGAAAT AGTTTTCAGT CGAC                                           1464
```

(2) INFORMATION FOR SEQ ID NO:12:

(i) SEQUENCE CHARACTERISTICS:
        (A) LENGTH: 477 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:12:

```
Met Gln Val Leu His Val Cys Ser Glu Met Phe Pro Leu Leu Lys Thr
1               5                   10                  15

Gly Gly Leu Ala Asp Val Ile Gly Ala Leu Pro Ala Ala Gln Ile Ala
                20                  25                  30

Asp Gly Val Asp Ala Arg Val Leu Leu Pro Ala Phe Pro Asp Ile Arg
            35                  40                  45

Arg Gly Val Thr Asp Ala Gln Val Val Ser Arg Arg Asp Thr Phe Ala
        50                  55                  60

Gly His Ile Thr Leu Leu Phe Gly His Tyr Asn Gly Val Gly Ile Tyr
65                  70                  75                  80

Leu Ile Asp Ala Pro His Leu Tyr Asp Arg Pro Gly Ser Pro Tyr His
                85                  90                  95

Asp Thr Asn Leu Phe Ala Tyr Thr Asp Asn Val Leu Arg Phe Ala Leu
                100                 105                 110

Leu Gly Trp Val Gly Ala Glu Met Ala Ser Gly Leu Asp Pro Phe Trp
            115                 120                 125

Arg Pro Asp Val Val His Ala His Asp Trp His Ala Gly Leu Ala Pro
        130                 135                 140

Ala Tyr Leu Ala Ala Arg Gly Arg Pro Ala Lys Ser Val Phe Thr Gly
145                 150                 155                 160

His Asn Leu Ala Tyr Gln Gly Met Phe Tyr Ala His His Met Asn Asp
                165                 170                 175

Ile Gln Leu Pro Trp Ser Phe Phe Asn Ile His Gly Leu Glu Phe Asn
                180                 185                 190

Gly Gln Ile Ser Phe Leu Lys Ala Gly Leu Tyr Tyr Ala Asp His Ile
            195                 200                 205

Thr Ala Val Ser Pro Thr Tyr Ala Arg Glu Ile Thr Glu Pro Gln Phe
        210                 215                 220

Ala Tyr Gly Met Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
                245                 250                 255

Thr Asp Leu Leu Leu Ala Ser Arg Tyr Thr Arg Asp Thr Leu Glu Asp
                260                 265                 270

Lys Ala Glu Asn Lys Arg Gln Leu Gln Ile Ala Met Gly Leu Lys Val
            275                 280                 285

Asp Asp Lys Val Pro Leu Phe Ala Val Val Ser Arg Leu Thr Ser Gln
        290                 295                 300

Lys Gly Leu Asp Leu Val Leu Glu Ala Leu Pro Gly Leu Leu Glu Gln
305                 310                 315                 320

Gly Gly Gln Leu Ala Leu Leu Gly Ala Gly Asp Pro Val Leu Gln Glu
                325                 330                 335

Gly Phe Leu Ala Ala Ala Glu Tyr Pro Gly Gln Val Gly Val Gln
                340                 345                 350

Ile Gly Tyr His Glu Ala Phe Ser His Arg Ile Met Gly Gly Ala Asp
            355                 360                 365

Val Ile Leu Val Pro Ser Arg Phe Glu Pro Cys Gly Leu Thr Gln Leu
        370                 375                 380

Tyr Gly Leu Lys Tyr Gly Thr Leu Pro Leu Val Arg Arg Thr Gly Gly
385                 390                 395                 400

Leu Ala Asp Thr Val Ser Asp Cys Ser Leu Glu Asn Leu Ala Asp Gly
```

```
                    405                 410                 415
Val Ala Ser Gly Phe Val Phe Glu Asp Ser Asn Ala Trp Ser Leu Leu
            420                 425                 430

Arg Ala Ile Arg Arg Ala Phe Val Leu Trp Ser Arg Pro Ser Leu Trp
            435                 440                 445

Arg Phe Val Gln Arg Gln Ala Met Ala Met Asp Phe Ser Trp Gln Val
    450                 455                 460

Ala Ala Lys Ser Tyr Arg Glu Leu Tyr Tyr Arg Ser Lys
465                 470                 475

(2) INFORMATION FOR SEQ ID NO:13:

(i) SEQUENCE CHARACTERISTICS:
        (A) LENGTH: 1323 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (ix) FEATURE:
        (A) NAME/KEY: CDS
        (B) LOCATION: 16..1308

(xi) SEQUENCE DESCRIPTION: SEQ ID NO:13:

GATCTAGGAG CGATA ATG GTT AGT TTA GAG AAG AAC GAT CAC TTA ATG TTG        51
                Met Val Ser Leu Glu Lys Asn Asp His Leu Met Leu
                  1               5                  10

GCG CGC CAG CTG CCA TTG AAA TCT GTT GCC CTG ATA CTG GCG GGA GGA         99
Ala Arg Gln Leu Pro Leu Lys Ser Val Ala Leu Ile Leu Ala Gly Gly
         15                  20                  25

CGT GGT ACC CGC CTG AAG GAT TTA ACC AAT AAG CGA GCA AAA CCG GCC        147
Arg Gly Thr Arg Leu Lys Asp Leu Thr Asn Lys Arg Ala Lys Pro Ala
 30                  35                  40

GTA CAC TTC GGC GGT AAG TTC CGC ATT ATC GAC TTT GCG CTG TCT AAC        195
Val His Phe Gly Gly Lys Phe Arg Ile Ile Asp Phe Ala Leu Ser Asn
 45                  50                  55                  60

TGC ATC AAC TCC GGG ATC CGT CGT ATG GGC GTG ATC ACC CAG TAC CAG        243
Cys Ile Asn Ser Gly Ile Arg Arg Met Gly Val Ile Thr Gln Tyr Gln
             65                  70                  75

TCC CAC ACT CTG GTG CAG CAC ATT CAG CGC GGC TGG TCA TTC TTC AAT        291
Ser His Thr Leu Val Gln His Ile Gln Arg Gly Trp Ser Phe Phe Asn
         80                  85                  90

GAA GAA ATG AAC GAG TTT GTC GAT CTG CTG CCA GCA CAG CAG AGA ATG        339
Glu Glu Met Asn Glu Phe Val Asp Leu Leu Pro Ala Gln Gln Arg Met
     95                 100                 105

AAA GGG GAA AAC TGG TAT CGC GGC ACC GCA GAT GCG GTC ACC CAA AAC        387
Lys Gly Glu Asn Trp Tyr Arg Gly Thr Ala Asp Ala Val Thr Gln Asn
110                 115                 120

CTC GAC ATT ATC CGC CGT TAT AAA GCG GAA TAC GTG GTG ATC CTG GCG        435
Leu Asp Ile Ile Arg Arg Tyr Lys Ala Glu Tyr Val Val Ile Leu Ala
125                 130                 135                 140

GGC GAC CAT ATC TAC AAG CAA GAC TAC TCG CGT ATG CTT ATC GAT CAC        483
Gly Asp His Ile Tyr Lys Gln Asp Tyr Ser Arg Met Leu Ile Asp His
                145                 150                 155

GTC GAA AAA GGC GCA CGT TGC ACC GTT GCT TGT ATG CCA GTA CCG ATT        531
Val Glu Lys Gly Ala Arg Cys Thr Val Ala Cys Met Pro Val Pro Ile
            160                 165                 170

GAA GAA GCC TCC GCA TTT GGC GTT ATG GCG GTT GAT GAG AAC GAT AAA        579
Glu Glu Ala Ser Ala Phe Gly Val Met Ala Val Asp Glu Asn Asp Lys
```

```
ATT ATC GAA TTC GTT GAA AAA CCT GCT AAC CCG CCG TCA ATG CCG AAC      627
Ile Ile Glu Phe Val Glu Lys Pro Ala Asn Pro Pro Ser Met Pro Asn
    190                 195                 200

GAT CCG AGC AAA TCT CTG GCG AGT ATG GGT ATC TAC GTC TTT GAC GCC      675
Asp Pro Ser Lys Ser Leu Ala Ser Met Gly Ile Tyr Val Phe Asp Ala
205                 210                 215                 220

GAC TAT CTG TAT GAA CTG CTG GAA GAA GAC GAT CGC GAT GAG AAC TCC      723
Asp Tyr Leu Tyr Glu Leu Leu Glu Glu Asp Asp Arg Asp Glu Asn Ser
                225                 230                 235

AGC CAC GAC TTT GGC AAA GAT TTG ATT CCC AAG ATC ACC GAA GCC GGT      771
Ser His Asp Phe Gly Lys Asp Leu Ile Pro Lys Ile Thr Glu Ala Gly
            240                 245                 250

CTG GCC TAT GCG CAC CCG TTC CCG CTC TCT TGC GTA CAA TCC GAC CCG      819
Leu Ala Tyr Ala His Pro Phe Pro Leu Ser Cys Val Gln Ser Asp Pro
        255                 260                 265

GAT GCC GAG CCG TAC TGG CGC GAT GTG GGT ACG CTG GAA GCT TAC TGG      867
Asp Ala Glu Pro Tyr Trp Arg Asp Val Gly Thr Leu Glu Ala Tyr Trp
    270                 275                 280

AAA GCG AAC CTC GAT CTG GCC TCT GTG GTG CCG GAA CTG GAT ATG TAC      915
Lys Ala Asn Leu Asp Leu Ala Ser Val Val Pro Glu Leu Asp Met Tyr
285                 290                 295                 300

GAT CGC AAT TGG CCA ATT CGC ACC TAC AAT GAA TCA TTA CCG CCA GCG      963
Asp Arg Asn Trp Pro Ile Arg Thr Tyr Asn Glu Ser Leu Pro Pro Ala
                305                 310                 315

AAA TTC GTG CAG GAT CGC TCC GGT AGC CAC GGG ATG ACC CTT AAC TCA     1011
Lys Phe Val Gln Asp Arg Ser Gly Ser His Gly Met Thr Leu Asn Ser
            320                 325                 330

CTG GTT TCC GAC GGT TGT GTG ATC TCC GGT TCG GTG GTG GTG CAG TCC     1059
Leu Val Ser Asp Gly Cys Val Ile Ser Gly Ser Val Val Val Gln Ser
        335                 340                 345

GTT CTG TTC TCG CGC GTT CGC GTG AAT TCA TTC TGC GAC ATT GAT TCC     1107
Val Leu Phe Ser Arg Val Arg Val Asn Ser Phe Cys Asp Ile Asp Ser
    350                 355                 360

GCC GTA TTG TTA CCG GAA GTA TGG GTA GGT CGC TCG TGC CGT CTG CGC     1155
Ala Val Leu Leu Pro Glu Val Trp Val Gly Arg Ser Cys Arg Leu Arg
365                 370                 375                 380

CGC TGC GTC ATC GAT CGT GCT TGT GTT ATT CCG GAA GGC ATG GTG ATT     1203
Arg Cys Val Ile Asp Arg Ala Cys Val Ile Pro Glu Gly Met Val Ile
                385                 390                 395

GGT GAA AAC GCA GAG GAA GAT GCA CGT CGT TTC TAT CGT TCA GAA GAA     1251
Gly Glu Asn Ala Glu Glu Asp Ala Arg Arg Phe Tyr Arg Ser Glu Glu
            400                 405                 410

GGC ATC GTG CTG GTA ACG CGC GAA ATG CTA CGG AAG TTA GGG CAT AAA     1299
Gly Ile Val Leu Val Thr Arg Glu Met Leu Arg Lys Leu Gly His Lys
        415                 420                 425

CAG GAG CGA TAATGCAGGG TCGAC                                        1323
Gln Glu Arg
    430
```

(2) INFORMATION FOR SEQ ID NO:14:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:14:

Met Val Ser Leu Glu Lys Asn Asp His Leu Met Leu Ala Arg Gln Leu

```
  1               5                  10                 15
Pro Leu Lys Ser Val Ala Leu Ile Leu Ala Gly Gly Arg Gly Thr Arg
             20                  25                 30
Leu Lys Asp Leu Thr Asn Lys Arg Ala Lys Pro Ala Val His Phe Gly
             35                  40                 45
Gly Lys Phe Arg Ile Ile Asp Phe Ala Leu Ser Asn Cys Ile Asn Ser
             50                  55                 60
Gly Ile Arg Arg Met Gly Val Ile Thr Gln Tyr Gln Ser His Thr Leu
 65                  70                  75                 80
Val Gln His Ile Gln Arg Gly Trp Ser Phe Phe Asn Glu Glu Met Asn
                     85                  90                 95
Glu Phe Val Asp Leu Leu Pro Ala Gln Gln Arg Met Lys Gly Glu Asn
                    100                 105                110
Trp Tyr Arg Gly Thr Ala Asp Ala Val Thr Gln Asn Leu Asp Ile Ile
                    115                 120                125
Arg Arg Tyr Lys Ala Glu Tyr Val Val Ile Leu Ala Gly Asp His Ile
                    130                 135                140
Tyr Lys Gln Asp Tyr Ser Arg Met Leu Ile Asp His Val Glu Lys Gly
145                 150                 155                160
Ala Arg Cys Thr Val Ala Cys Met Pro Val Pro Ile Glu Glu Ala Ser
                    165                 170                175
Ala Phe Gly Val Met Ala Val Asp Glu Asn Asp Lys Ile Ile Glu Phe
                    180                 185                190
Val Glu Lys Pro Ala Asn Pro Pro Ser Met Pro Asn Asp Pro Ser Lys
                    195                 200                205
Ser Leu Ala Ser Met Gly Ile Tyr Val Phe Asp Ala Asp Tyr Leu Tyr
    210                 215                 220
Glu Leu Leu Glu Glu Asp Asp Arg Asp Glu Asn Ser Ser His Asp Phe
225                 230                 235                240
Gly Lys Asp Leu Ile Pro Lys Ile Thr Glu Ala Gly Leu Ala Tyr Ala
                    245                 250                255
His Pro Phe Pro Leu Ser Cys Val Gln Ser Asp Pro Asp Ala Glu Pro
                    260                 265                270
Tyr Trp Arg Asp Val Gly Thr Leu Glu Ala Tyr Trp Lys Ala Asn Leu
                    275                 280                285
Asp Leu Ala Ser Val Val Pro Glu Leu Asp Met Tyr Asp Arg Asn Trp
    290                 295                 300
Pro Ile Arg Thr Tyr Asn Glu Ser Leu Pro Pro Ala Lys Phe Val Gln
305                 310                 315                320
Asp Arg Ser Gly Ser His Gly Met Thr Leu Asn Ser Leu Val Ser Asp
                    325                 330                335
Gly Cys Val Ile Ser Gly Ser Val Val Gln Ser Val Leu Phe Ser
                    340                 345                350
Arg Val Arg Val Asn Ser Phe Cys Asp Ile Asp Ser Ala Val Leu Leu
    355                 360                 365
Pro Glu Val Trp Val Gly Arg Ser Cys Arg Leu Arg Arg Cys Val Ile
    370                 375                 380
Asp Arg Ala Cys Val Ile Pro Glu Gly Met Val Ile Gly Glu Asn Ala
385                 390                 395                400
Glu Glu Asp Ala Arg Arg Phe Tyr Arg Ser Glu Glu Gly Ile Val Leu
                    405                 410                415
Val Thr Arg Glu Met Leu Arg Lys Leu Gly His Lys Gln Glu Arg
                    420                 425                430
```

(2) INFORMATION FOR SEQ ID NO:15:

(i) SEQUENCE CHARACTERISTICS:
        (A) LENGTH: 281 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (ix) FEATURE:
        (A) NAME/KEY: CDS
        (B) LOCATION: join(1..36, 40..279)

(xi) SEQUENCE DESCRIPTION: SEQ ID NO:15:

```
TCT AGA AGC TTG GAT ATC TGG CAG CAG AAA AAC AAG TAG TTG AGA ACT      48
Ser Arg Ser Leu Asp Ile Trp Gln Gln Lys Asn Lys  *  Leu Arg Thr
 1               5                  10                  15

AAG AAG AAG AAA ATG GCT TCC TCA ATG ATC TCC TCC CCA GCT GTT ACC      96
Lys Lys Lys Lys Met Ala Ser Ser Met Ile Ser Ser Pro Ala Val Thr
             20                  25                  30

ACC GTC AAC CGT GCC GGT GCC GGC ATG GTT GCT CCA TTC ACC GGC CTC     144
Thr Val Asn Arg Ala Gly Ala Gly Met Val Ala Pro Phe Thr Gly Leu
         35                  40                  45

AAA TCC ATG GCT GGC TTC CCC ACG AGG AAG ACC AAC AAT GAC ATT ACC     192
Lys Ser Met Ala Gly Phe Pro Thr Arg Lys Thr Asn Asn Asp Ile Thr
     50                  55                  60

TCC ATT GCT AGC AAC GGT GGA AGA GTA CAA TGC ATG CAG GTG TGG CCT     240
Ser Ile Ala Ser Asn Gly Gly Arg Val Gln Cys Met Gln Val Trp Pro
 65                  70                  75                  80

CCA ATT GGA AAG AAG AAG TTT GAG ACT CTT TCC TGG GAT CC              281
Pro Ile Gly Lys Lys Lys Phe Glu Thr Leu Ser Trp Asp
                 85                  90
```

(2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:16:

```
Ser Arg Ser Leu Asp Ile Trp Gln Gln Lys Asn Lys
 1               5                  10
```

(2) INFORMATION FOR SEQ ID NO:17:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:17:

```
Leu Arg Thr Lys Lys Lys Lys Met Ala Ser Ser Met Ile Ser Ser Pro
 1               5                  10                  15

Ala Val Thr Thr Val Asn Arg Ala Gly Ala Gly Met Val Ala Pro Phe
                 20                  25                  30

Thr Gly Leu Lys Ser Met Ala Gly Phe Pro Thr Arg Lys Thr Asn Asn
             35                  40                  45
```

```
Asp Ile Thr Ser Ile Ala Ser Asn Gly Gly Arg Val Gln Cys Met Gln
        50                  55                  60

Val Trp Pro Pro Ile Gly Lys Lys Lys Phe Glu Thr Leu Ser Trp Asp
 65      70      75                  80
```

(2) INFORMATION FOR SEQ ID NO:18:

(i) SEQUENCE CHARACTERISTICS:
        (A) LENGTH: 281 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (ix) FEATURE:
        (A) NAME/KEY: CDS
        (B) LOCATION: join(2..40, 44..73, 77..280)

(xi) SEQUENCE DESCRIPTION: SEQ ID NO:18:

```
T CTA GAA GCT TGG ATA TCT GGC AGC AGA AAA ACA AGT AGT TGA GAA            46
  Leu Glu Ala Trp Ile Ser Gly Ser Arg Lys Thr Ser Ser  *  Glu
   1           5                  10                      15

CTA AGA AGA AGA AAA TGG CTT CCT CAA TGA TCT CCT CCC CAG CTG TTA          94
Leu Arg Arg Arg Lys Trp Leu Pro Gln  *  Ser Pro Pro Gln Leu Leu
                 20                  25                  30

CCA CCG TCA ACC GTG CCG GTG CCG GCA TGG TTG CTC CAT TCA CCG GCC         142
Pro Pro Ser Thr Val Pro Val Pro Ala Trp Leu Leu His Ser Pro Ala
             35                  40                  45

TCA AAT CCA TGG CTG GCT TCC CCA CGA GGA AGA CCA ACA ATG ACA TTA         190
Ser Asn Pro Trp Leu Ala Ser Pro Arg Gly Arg Pro Thr Met Thr Leu
         50                  55                  60

CCT CCA TTG CTA GCA ACG GTG GAA GAG TAC AAT GCA TGC AGG TGT GGC         238
Pro Pro Leu Leu Ala Thr Val Glu Glu Tyr Asn Ala Cys Arg Cys Gly
     65                  70                  75

CTC CAA TTG GAA AGA AGA AGT TTG AGA CTC TTT CCT GGG ATC                 280
Leu Gln Leu Glu Arg Arg Ser Leu Arg Leu Phe Pro Gly Ile
 80                  85                  90

C                                                                       281
```

(2) INFORMATION FOR SEQ ID NO:19:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:19:

```
Leu Glu Ala Trp Ile Ser Gly Ser Arg Lys Thr Ser Ser
 1           5                  10
```

(2) INFORMATION FOR SEQ ID NO:20:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:20:

```
Glu Leu Arg Arg Arg Lys Trp Leu Pro Gln
 1               5                  10
```

(2) INFORMATION FOR SEQ ID NO:21:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:21:

```
Ser Pro Pro Gln Leu Leu Pro Pro Ser Thr Val Pro Val Pro Ala Trp
 1               5                  10                  15

Leu Leu His Ser Pro Ala Ser Asn Pro Trp Leu Ala Ser Pro Arg Gly
                20                  25                  30

Arg Pro Thr Met Thr Leu Pro Pro Leu Leu Ala Thr Val Glu Glu Tyr
            35                  40                  45

Asn Ala Cys Arg Cys Gly Leu Gln Leu Glu Arg Arg Ser Leu Arg Leu
50                  55                  60

Phe Pro Gly Ile
65
```

(2) INFORMATION FOR SEQ ID NO:22:

(i) SEQUENCE CHARACTERISTICS:
        (A) LENGTH: 281 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (ix) FEATURE:
        (A) NAME/KEY: CDS
        (B) LOCATION: join(6..47, 51..182, 186..200, 204..260,
            264..281)

(xi) SEQUENCE DESCRIPTION: SEQ ID NO:22:

```
TCTAG AAG CTT GGA TAT CTG GCA GCA GAA AAA CAA GTA GTT GAG AAC        47
      Lys Leu Gly Tyr Leu Ala Ala Glu Lys Gln Val Val Glu Asn
       1               5                  10

TAA GAA GAA GAA AAT GGC TTC CTC AAT GAT CTC CTC CCC AGC TGT TAC       95
 *  Glu Glu Glu Asn Gly Phe Leu Asn Asp Leu Leu Pro Ser Cys Tyr
        15                  20                  25              30

CAC CGT CAA CCG TGC CGG TGC CGG CAT GGT TGC TCC ATT CAC CGG CCT      143
His Arg Gln Pro Cys Arg Cys Arg His Gly Cys Ser Ile His Arg Pro
                    35                  40                  45

CAA ATC CAT GGC TGG CTT CCC CAC GAG GAA GAC CAA CAA TGA CAT TAC      191
Gln Ile His Gly Trp Leu Pro His Glu Glu Asp Gln Gln  *  His Tyr
                50                  55                  60

CTC CAT TGC TAG CAA CGG TGG AAG AGT ACA ATG CAT GCA GGT GTG GCC      239
Leu His Cys  *  Gln Arg Trp Lys Ser Thr Met His Ala Gly Val Ala
                65                  70                  75

TCC AAT TGG AAA GAA GAA GTT TGA GAC TCT TTC CTG GGA TCC              281
Ser Asn Trp Lys Glu Glu Val  *  Asp Ser Phe Leu Gly Ser
            80                  85                  90
```

(2) INFORMATION FOR SEQ ID NO:23:

(i) SEQUENCE CHARACTERISTICS:

(A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:23:

Lys Leu Gly Tyr Leu Ala Ala Glu Lys Gln Val Val Glu Asn
 1               5                  10

(2) INFORMATION FOR SEQ ID NO:24:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:24:

Glu Glu Glu Asn Gly Phe Leu Asn Asp Leu Leu Pro Ser Cys Tyr His
 1               5                  10                  15

Arg Gln Pro Cys Arg Cys Arg His Gly Cys Ser Ile His Arg Pro Gln
            20                  25                  30

Ile His Gly Trp Leu Pro His Glu Glu Asp Gln Gln
        35                  40

(2) INFORMATION FOR SEQ ID NO:25:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:25:

His Tyr Leu His Cys
 1               5

(2) INFORMATION FOR SEQ ID NO:26:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:26:

Gln Arg Trp Lys Ser Thr Met His Ala Gly Val Ala Ser Asn Trp Lys
 1               5                  10                  15

Glu Glu Val (2) INFORMATION FOR SEQ ID NO:27:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:27:

Asp Ser Phe Leu Gly Ser
 1               5

(2) INFORMATION FOR SEQ ID NO:28:

(i) SEQUENCE CHARACTERISTICS:
        (A) LENGTH: 718 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (xi) SEQUENCE DESCRIPTION: SEQ ID NO:28:

```
CTCGAGATTT GTCAAATCAG GCTCAAAGAT CGTTTTTCAT ATCGGAATGA GGATTTTATT      60
TATTCTTTTA AAAATAAAGA GGTGTTGAGC TAAACAATTT CAAATCTCAT CACACATATG     120
GGGTCAGCCA CAAAAATAAA GAACGGTTGG AACGGATCTA TTATATAATA CTAATAAAGA     180
ATAGAAAAAG GAAAGTGAGT GAGGTGCGAG GGAGAGAATC TGTTTACTAT CAGAGTCGAT     240
CATGTGTCAG TTTTATCGAT ATGACTCTGA CTTCAACTGA GTTTAAGCAA TTCTGATAAG     300
GCGAGGAAAA TCACAGTGCT GAATCTAGAA AAATCTCATA GTGTGAGATA AGTCTCAACA     360
AAAACGTTGA GTCCATAGAG GGGGTGTATG TGACACCCCA ACCTCAGCAA AAGAAAACCT     420
CCCCTCAAGA AGGACATTTG CGGTGCTAAA CAATTTCAAG TCTCATCACA CATATATATT     480
ATATAATACT AATAAAGAAT AGAAAAAGGA AAGGTAAACA TCACTAATGA CAGTTGCGGT     540
GCAAAGTGAG TGAGATAATA AACATCAGTA ATAGACATCA CTAACTTTTA TTGGTTATGT     600
CAAACTCAAA ATAAAATTTC TCAACTTGTT TACGTGCCTA TATATACCAT GCTTGTTATA     660
TGCTCAAAGC ACCAACAAAA TTTAAAAACA ATTTGAACAT TTGCAAAACT AGTATGGG      718
```

(2) INFORMATION FOR SEQ ID NO:29:

(i) SEQUENCE CHARACTERISTICS:
        (A) LENGTH: 703 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (xi) SEQUENCE DESCRIPTION: SEQ ID NO:29:

```
ATTTGTCAAA TCAGGCTCAA AGATCGTTTT TCATATCGGA ATGAGGATTT TATTTATTCT      60
TTTAAAAATA AAGAGGTGTT GAGCTAAACA ATTTCAAATC TCATCACACA TATGGGGTCA     120
GCCACAAAAA TAAAGAACGG TTGGAACGGA TCTATTATAT AATACTAATA AAGAATAGAA     180
AAAGGAAAGT GAGTGAGGTG CGAGGGAGAG AATCTGTTTA CTATCAGAGT CGATCATGTG     240
TCAGTTTTAT CGATATGACT CTGATTTCAA CTGAGTTTAA GCAATTCTGA TAAGGCGAGG     300
AAAATCACAG TGCTGAAATC TAGAAAAATC TCATAGTGTG AGATAAGTCT CAACAAAAAC     360
GTTGAGTCCA TAGAGGGGGT GTATGTGACA CCCCAACCTC AGCAAAAGAA AACCTCCCCT     420
CAAGAAGGAC ATTTGCGGTG CTAAACAATT TCAAGTCTCA TCACACATAT ATATTATATA     480
ATACTAATAA AGAATAGAAA AAGGAAAGGT AAACATCACT AATGACAGTT GCGGTGCAAA     540
GTGAGTGAGA TAATAAACAT CAGTAATAGA CATCACTAAC TTTTATTGGT TATGTCAAAC     600
TCAAAATAAA ATTTCTCAAC TTGTTTACGT GCCTATATAT ACCATGCTTG TTATATGCTC     660
AAAGCACCAA CAAAATTTAA AAACAATTTG AACATTTGCA AAA                      703
```

(2) INFORMATION FOR SEQ ID NO:30:

(i) SEQUENCE CHARACTERISTICS:
        (A) LENGTH: 650 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (vi) ORIGINAL SOURCE:
        (A) ORGANISM: Solanum tuberosum (ix) FEATURE:
        (D) OTHER INFORMATION: Sequence from 5' untranslated regions
            of variety Russet Burbank (xi) SEQUENCE DESCRIPTION: SEQ ID NO:30:

```
CTCGAGATTT GTCAAATCAG GCTCAAAGAT CGTTTTTCAT ATCGGAATGA GGATTTTATT      60

TATTCTTTTA AAAATAAAGA GGTGGTGAGC TAAACAATTT CAAATCTCAT CACACATATG     120

GGGTCAGCCA CAAAAATAAA GAACGGTTGG AACGGATCTA TTATATAATA CTAATAAAGA     180

ATAGGAAAAG GAAAGTGAGT GAGGTGCGAG GGAGAGAATT TGTTTAATAT CAGAGTCGAT     240

CATGTGTCAG TTTTATCGAT ATGATTCTGA CTTCAACTGA GTTTAAGCAA TTCTGATAAG     300

GCGGAGAAAA TCATAGTGCT GAGTCTAGAA AAATCTCATG CAGTGTGAGA TAAACCTCAA     360

CAAGAACATT TGCGGTGCTA AACAATTTCA AGTCTTATCA CACATATATA TTATATATTA     420

CTAATAAAGA ATAGAAAAAG GAAAGGTAAA CATCACTAAT GACAGTTGCG GTGCAAAGTG     480

AGTGAGATAA TAAACATCAC TAATAGACAT CACTAACTTT TATTGGTTAT GTCAAACTCA     540

AAATAAAATT TCTCAACTTG TTTACGTGCC TATATATACC ATGCTTGTTA TATGCTCAAA     600

GCACCAACAA AATTTAAAAA CAATTTGAAC ATTTGCAAAA CTAGTATGGG               650
```

(2) INFORMATION FOR SEQ ID NO:31:

(i) SEQUENCE CHARACTERISTICS:
        (A) LENGTH: 703 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (vi) ORIGINAL SOURCE:
        (A) ORGANISM: Solanum tuberosum (ix) FEATURE:
        (D) OTHER INFORMATION: Sequence from 5' untranslated regions
            of variety Maris Piper (xi) SEQUENCE DESCRIPTION: SEQ ID NO:31:

```
ATTTGTCAAA TCAGGCTCAA AGATCGTTTT TCATATCGGA ATGAGGATTT TATTTATTCT      60

TTTAAAAATA AAGAGGTGTT GAGCTAAACA ATTTCAAATC TCATCACACA TATGGGGTCA     120

GCCACAAAAA TAAAGAACGG TTGGAACGGA TCTATTATAT AATACTAATA AGAATAGAA     180

AAAGGAAAGT GAGTGAGGTG CGAGGGAGAG AATCTGTTTA CTATCAGAGT CGATCATGTG     240

TCAGTTTTAT CGATATGACT CTGATTTCAA CTGAGTTTAA GCAATTCTGA TAAGGCGAGG     300

AAAATCACAG TGCTGAAATC TAGAAAAATC TCATAGTGTG AGATAAGTCT CAACAAAAAC     360

GTTGAGTCCA TAGAGGGGGT GTATGTGACA CCCCAACCTC AGCAAAAGAA AACCTCCCCT     420
```

-continued

| | |
|---|---|
| CAAGAAGGAC ATTTGCGGTG CTAAACAATT TCAAGTCTCA TCACACATAT ATATTATATA | 480 |
| ATACTAATAA AGAATAGAAA AAGGAAAGGT AAACATCACT AATGACAGTT GCGGTGCAAA | 540 |
| GTGAGTGAGA TAATAAACAT CAGTAATAGA CATCACTAAC TTTTATTGGT TATGTCAAAC | 600 |
| TCAAAATAAA ATTTCTCAAC TTGTTTACGT GCCTATATAT ACCATGCTTG TTATATGCTC | 660 |
| AAAGCACCAA CAAAATTTAA AAACAATTTG AACATTTGCA AAA | 703 |

(2) INFORMATION FOR SEQ ID NO:32:

(i) SEQUENCE CHARACTERISTICS:
        (A) LENGTH: 2000 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (xi) SEQUENCE DESCRIPTION: SEQ ID NO:32:

| | |
|---|---|
| GGATCCATTA GGACTAGATA ATGAAAAGAA ACCGTTTTTT TAATACCTCG GCTGCTATTG | 60 |
| CCATTTCGAT TGCATTAAAT ACTTTTTTTT GTAGCATGCA GACGATTGCT GCTGAACCAG | 120 |
| AAGAAACTTA TCTTGATTTT CGTAAGGAGA CGATATATTT TCTATTCCTT GATCGTTTCA | 180 |
| GCGATGGAGA TCCAAGTAAT AATGCAGGGT TTAATTCTGC AACCTACGAT CCTAATAATT | 240 |
| TAAAAAAATA TACTGGAGGA GATCTCCGGG GGTTGATTAA TAAACTACCC TATTTAAAAT | 300 |
| CACTTGGTGT TACTTCAATC TGGATTACTC CCCCAATCGA TAATGTGAAT AATACTGATG | 360 |
| CTGCTGGCAA TACTGGATAT CATGGTTATT GGGGAAGAGA TTATTTTCGT ATAGATGAAC | 420 |
| ATTTTGGCAA TCTCGATGAT TTCAAAGAAC TGACTAGTTT GATGCATAGT CCTGATTATA | 480 |
| ATATGAAACT GGTTCTTGAT TATGCCCCTA ATCATTCGAA TGCTAATGAT GAAAATGAAT | 540 |
| TTGGTGCACT ATATCGTGAT GGTGTGTTTA TTACTGATTA TCCTACAGAT GTTGCCGCCA | 600 |
| ATACGGGCTG GTATCATCAC AATGGTGGGG TAACGAACTG GAATGATTTC TTCCAAGTGA | 660 |
| AGAATCATAA TCTATTCAAT CTATCAGACC TCAATCAATC CAATACTGAT GTCTACCAGT | 720 |
| ACTTGTTGGA TGGCTCTAAA TTTTGGATCG ATGCTGGTGT GGATGCTATC AGGATTGATG | 780 |
| CCATCAAGCA TATGGACAAG TCTTTTATAC AGAAATGGAC CAGCGATATT TATGATTACA | 840 |
| GTAAGTCTAT CGGCCGGGAA GGATTTTTTT TCTTCGGTGA ATGGTTTGGT GCCAGTGCGA | 900 |
| ATACTACAAC AGGTGTTGAT GGTAATGCTA TCGATTACGC CAACACTTCC GGGTCAGCGT | 960 |
| TGCTGGATTT TGGATTCCGC GATACTTTAG AAAGAGTTTT GGTAGGACGT AGCGGAAATA | 1020 |
| CAATGAAAAC GTTAAATAGT TATCTGATAA AAAGACAAAC AGTCTTTACC AGTGATGACT | 1080 |
| GGCAGGTTGT TTTTATGGAT AACCATGATA TGGCACGCAT TGGTACCGCT CTGCGTTCAA | 1140 |
| ACGCCACTAC TTTTGGTCCT GGAAATAATG AAACCGGTGG AAGTCAGAGT GAAGCTTTTG | 1200 |
| CTCAGAAACG TATAGACCTC GGTCTGGTTG CGACAATGAC TGTACGTGGT ATTCCTGCCA | 1260 |
| TTTATTATGG TACTGAACAT TATGCCGCTA ACTTTACCTC TAACAGTTTT GGTCAAGTTG | 1320 |
| GCAGTGATCC TTACAACCGA GAGAAAATGC CAGGATTTGA TACGGAAAGT GAGGCTTTCT | 1380 |
| CCATTATTAA AACACTGGGT GACCTAAGGA AAAGTAGCCC GGCAATTCAA AATGGAACTT | 1440 |
| ATACTGAACT ATGGGTTAAT GATGATATAT TAGTATTTGA GCGGCGTTCT GGGAACGATA | 1500 |
| TTGTTATTGT TGCACTTAAT CGTGGTGAGG CTAACACAAT TAATGTTAAA AATATAGCGG | 1560 |
| TTCCTAATGG GGTATATCCG AGTTTGATTG GGAATAATAG TGTTTCAGTA GCAAATAAAC | 1620 |

-continued

| | |
|---|---|
| AGGCAACACT AACACTTATG CAAAATGAAG CTGTTGTCAT TCGCTCACAA TCAGATGATG | 1680 |
| CGGAGAACCC TACAGTACAA AGCATAAACT TCGCATGTAA TAACGGTTAT ACGATTTCAG | 1740 |
| GTCAAAGTGT TTATATTATT GGTAATATAC CTCAGTTAGG TGGTTGGGAC TTAACTAAAG | 1800 |
| CGGTAAAAAT ATCACCGACA CAATATCCAC AATGGAGTGC GAGCTTAGAG CTTCCTTCTG | 1860 |
| ACTTAAATGT TGAATGGAAG TGTGTGAAAC GTAATGAAAC CAATCCGACG GCTAATGTTG | 1920 |
| AGTGGCAGTC TGGTGCAAAT AACCAGTTCA ATAGCAATGA CACACAAACA ACGAATGGCT | 1980 |
| CGTTTTAATT AAAAGTCGAC | 2000 |

(2) INFORMATION FOR SEQ ID NO:33:

(i) SEQUENCE CHARACTERISTICS:
        (A) LENGTH: 1988 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (xi) SEQUENCE DESCRIPTION: SEQ ID NO:33:

| | |
|---|---|
| ATTAGGACTA GATAATGAAA AGAAACCGTT TTTTTAATAC CTCGGCTGCT ATTGCCATTT | 60 |
| CGATTGCATT AAATACTTTT TTTTGTAGCA TGCAGACGAT TGCTGCTGAA CCAGAAGAAA | 120 |
| CTTATCTTGA TTTTCGTAAG GAGACGATAT ATTTTCTATT CCTTGATCGT TTCAGCGATG | 180 |
| GAGATCCAAG TAATAATGCA GGGTTTAATT CTGCAACCTA CGATCCTAAT AATTTAAAAA | 240 |
| AATATACTGG AGGAGATCTC CGGGGGTTGA TTAATAAACT ACCCTATTTA AAATCACTTG | 300 |
| GTGTTACTTC AATCTGGATT ACTCCCCCAA TCGATAATGT GAATAATACT GATGCTGCTG | 360 |
| GCAATACTGG ATATCATGGT TATTGGGGAA GAGATTATTT TCGTATAGAT GAACATTTTG | 420 |
| GCAATCTCGA TGATTTCAAA GAACTGACTA GTTTGATGCA TAGTCCTGAT TATAATATGA | 480 |
| AACTGGTTCT TGATTATGCC CCTAATCATT CGAATGCTAA TGATGAAAAT GAATTTGGTG | 540 |
| CACTATATCG TGATGGTGTG TTTATTACTG ATTATCCTAC GAATGTTGCC GCCAATACGG | 600 |
| GCTGGTATCA TCACAATGGT GGGGTAACGA ACTGGAATGA TTTCTTCCAA GTGAAGAATC | 660 |
| ATAATCTATT CAATCTATCA GACCTCAATC AATCCAATAC TGATGTCTAC CAGTACTTGT | 720 |
| TGGATGGTTC TAAATTTTGG ATCGATGCTG GTGTGGATGC TATCAGGATT GATGCCATCA | 780 |
| AGCATATGGA CAAGTCTTTT ATACAGAAAT GGACCAGCGA TATTTATGAT TACAGTAAGT | 840 |
| CTATCGGCCG GGAAGGATTT TTTTTCTTCG GTGAATGGTT TGGTGCCAGT GCGAATACTA | 900 |
| CAACAGGTGT TGATGGTAAT GCTATCGATT ACGCCAACAC TTCCGGGTCA GCGTTGCTGG | 960 |
| ATTTTGGATT CCGCGATACT TTAGAAAGAG TTTTGGTAGG ACGTAGCGGA AATACAATGA | 1020 |
| AAACGTTAAA TAGTTATCTG ATAAAAAGAC AAACAGTCTT TACCAGTGAT GACTGGCAGG | 1080 |
| TTGTTTTTAT GGATAACCAT GATATGGCAC GCATTGGTAC CGCTCTGCGT TCAAACGCCA | 1140 |
| CTACTTTTGG TCCTGGAAAT AATGAAACCG GTGGAAGTCA GAGTGAAGCT TTTGCTCAGA | 1200 |
| AACGTATAGA CCTCGGTCTG GTTGCGACAA TGACTGTACG TGGTATTCCT GCCATTTATT | 1260 |
| ATGGTACTGA ACATTATGCC GCTAACTTTA CCTCTAACAG TTTTGGTCAA GTTGGCAGTG | 1320 |
| ATCCTTACAA CCGAGAGAAA ATGCCAGGAT TGATACGGA AAGTGAGGCT TTCTCCATTA | 1380 |
| TTAAAACACT GGGTGACCTA AGGAAAAGTA GCCCGGCAAT TCAAAATGGA ACTTATACTG | 1440 |
| AACTATGGGT TAATGATGAT ATATTAGTAT TTGAGCGGCG TTCTGGGAAC GATATTGTTA | 1500 |

-continued

```
TTGTTGCACT TAATCGTGGT GAGGCTAACA CAATTAATGT TAAAAATATA GCGGTTCCTA    1560

ATGGGGTATA TCCGAGTTTG ATTGGGAATA ATAGTGTTTC AGTAGCAAAT AAACGGACAA    1620

CACTAACACT TATGCAAAAT GAAGCTGTTG TCATTCGCTC ACAATCAGAT GATGCGGAGA    1680

ACCCTACAGT ACAAAGCATA AACTTCACAT GTAATAACGG TTATACGATT TCAGGTCAAA    1740

GTGTTTATAT TATTGGTAAT ATACCTCAGT TAGGTGGTTG GGACTTAACT AAAGCGGTAA    1800

AAATATCACC GACACAATAT CCACAATGGA GTGCGAGCTT AGAGCTTCCT TCTGACTTAA    1860

ATGTTGAATG GAAGTGTGTG AAACGTAATG AAACCAATCC GACGGCTAAT GTTGAGTGGC    1920

AGTCTGGTGC AAATAACCAG TTCAATAGCA ATGACACACA AACAACGAAT GGCTCGTTTT    1980

AATTAAAA                                                              1988
```

(2) INFORMATION FOR SEQ ID NO:34:

(i) SEQUENCE CHARACTERISTICS:
        (A) LENGTH: 655 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:34:

```
Met Lys Arg Asn Arg Phe Phe Asn Thr Ser Ala Ala Ile Ala Ile Ser
1               5                  10                  15

Ile Ala Leu Asn Thr Phe Phe Cys Ser Met Gln Thr Ile Ala Ala Glu
                20                  25                  30

Pro Glu Glu Thr Tyr Leu Asp Phe Arg Lys Glu Thr Ile Tyr Phe Leu
            35                  40                  45

Phe Leu Asp Arg Phe Ser Asp Gly Asp Pro Ser Asn Asn Ala Gly Phe
        50                  55                  60

Asn Ser Ala Thr Tyr Asp Pro Asn Asn Leu Lys Lys Tyr Thr Gly Gly
65                  70                  75                  80

Asp Leu Arg Gly Leu Ile Asn Lys Leu Pro Tyr Leu Lys Ser Leu Gly
                85                  90                  95

Val Thr Ser Ile Trp Ile Thr Pro Pro Ile Asp Asn Val Asn Asn Thr
                100                 105                 110

Asp Ala Ala Gly Asn Thr Gly Tyr His Gly Tyr Trp Gly Arg Asp Tyr
            115                 120                 125

Phe Arg Ile Asp Glu His Phe Gly Asn Leu Asp Asp Phe Lys Glu Leu
        130                 135                 140

Thr Ser Leu Met His Ser Pro Asp Tyr Asn Met Lys Leu Val Leu Asp
145                 150                 155                 160

Tyr Ala Pro Asn His Ser Asn Ala Asn Asp Glu Asn Glu Phe Gly Ala
                165                 170                 175

Leu Tyr Arg Asp Gly Val Phe Ile Thr Asp Tyr Pro Thr Asp Val Ala
            180                 185                 190

Ala Asn Thr Gly Trp Tyr His His Asn Gly Gly Val Thr Asn Trp Asn
        195                 200                 205

Asp Phe Phe Gln Val Lys Asn His Asn Leu Phe Asn Leu Ser Asp Leu
        210                 215                 220

Asn Gln Ser Asn Thr Asp Val Tyr Gln Tyr Leu Leu Asp Gly Ser Lys
225                 230                 235                 240

Phe Trp Ile Asp Ala Gly Val Asp Ala Ile Arg Ile Asp Ala Ile Lys
```

-continued

```
                        245                     250                     255
    His Met Asp Lys Ser Phe Ile Gln Lys Trp Thr Ser Asp Ile Tyr Asp
                    260                     265                     270

Tyr Ser Lys Ser Ile Gly Arg Glu Gly Phe Phe Phe Gly Glu Trp
                275                     280                     285

Phe Gly Ala Ser Ala Asn Thr Thr Gly Val Asp Gly Asn Ala Ile
            290                     295                     300

Asp Tyr Ala Asn Thr Ser Gly Ser Ala Leu Leu Asp Phe Gly Phe Arg
    305                     310                     315                     320

Asp Thr Leu Glu Arg Val Leu Val Gly Arg Ser Gly Asn Thr Met Lys
                        325                     330                     335

Thr Leu Asn Ser Tyr Leu Ile Lys Arg Gln Thr Val Phe Thr Ser Asp
                    340                     345                     350

Asp Trp Gln Val Val Phe Met Asp Asn His Asp Met Ala Arg Ile Gly
                355                     360                     365

Thr Ala Leu Arg Ser Asn Ala Thr Thr Phe Gly Pro Gly Asn Asn Glu
            370                     375                     380

Thr Gly Gly Ser Gln Ser Glu Ala Phe Ala Gln Lys Arg Ile Asp Leu
    385                     390                     395                     400

Gly Leu Val Ala Thr Met Thr Val Arg Gly Ile Pro Ala Ile Tyr Tyr
                        405                     410                     415

Gly Thr Glu His Tyr Ala Ala Asn Phe Thr Ser Asn Ser Phe Gly Gln
                    420                     425                     430

Val Gly Ser Asp Pro Tyr Asn Arg Glu Lys Met Pro Gly Phe Asp Thr
                435                     440                     445

Glu Ser Glu Ala Phe Ser Ile Ile Lys Thr Leu Gly Asp Leu Arg Lys
            450                     455                     460

Ser Ser Pro Ala Ile Gln Asn Gly Thr Tyr Thr Glu Leu Trp Val Asn
    465                     470                     475                     480

Asp Asp Ile Leu Val Phe Glu Arg Arg Ser Gly Asn Asp Ile Val Ile
                        485                     490                     495

Val Ala Leu Asn Arg Gly Glu Ala Asn Thr Ile Asn Val Lys Asn Ile
                    500                     505                     510

Ala Val Pro Asn Gly Val Tyr Pro Ser Leu Ile Gly Asn Asn Ser Val
                515                     520                     525

Ser Val Ala Asn Lys Gln Ala Thr Leu Thr Leu Met Gln Asn Glu Ala
            530                     535                     540

Val Val Ile Arg Ser Gln Ser Asp Asp Ala Glu Asn Pro Thr Val Gln
    545                     550                     555                     560

Ser Ile Asn Phe Ala Cys Asn Asn Gly Tyr Thr Ile Ser Gly Gln Ser
                        565                     570                     575

Val Tyr Ile Ile Gly Asn Ile Pro Gln Leu Gly Gly Trp Asp Leu Thr
                    580                     585                     590

Lys Ala Val Lys Ile Ser Pro Thr Gln Tyr Pro Gln Trp Ser Ala Ser
                595                     600                     605

Leu Glu Leu Pro Ser Asp Leu Asn Val Glu Trp Lys Cys Val Lys Arg
            610                     615                     620

Asn Glu Thr Asn Pro Thr Ala Asn Val Glu Trp Gln Ser Gly Ala Asn
    625                     630                     635                     640

Asn Gln Phe Asn Ser Asn Asp Thr Gln Thr Thr Asn Gly Ser Phe
                        645                     650                     655
```

(2) INFORMATION FOR SEQ ID NO:35:

(i) SEQUENCE CHARACTERISTICS:
    (A) LENGTH: 655 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:35:

```
Met Lys Arg Asn Arg Phe Phe Asn Thr Ser Ala Ala Ile Ala Ile Ser
1               5                  10                  15

Ile Ala Leu Asn Thr Phe Phe Cys Ser Met Gln Thr Ile Ala Ala Glu
                20                  25                  30

Pro Glu Glu Thr Tyr Leu Asp Phe Arg Lys Glu Thr Ile Tyr Phe Leu
                35                  40                  45

Phe Leu Asp Arg Phe Ser Asp Gly Asp Pro Ser Asn Asn Ala Gly Phe
50                      55                  60

Asn Ser Ala Thr Tyr Asp Pro Asn Asn Leu Lys Lys Tyr Thr Gly Gly
65                  70                  75                  80

Asp Leu Arg Gly Leu Ile Asn Lys Leu Pro Tyr Leu Lys Ser Leu Gly
                85                  90                  95

Val Thr Ser Ile Trp Ile Thr Pro Pro Ile Asp Asn Val Asn Asn Thr
                100                 105                 110

Asp Ala Ala Gly Asn Thr Gly Tyr His Gly Tyr Trp Gly Arg Asp Tyr
                115                 120                 125

Phe Arg Ile Asp Glu His Phe Gly Asn Leu Asp Asp Phe Lys Glu Leu
130                     135                 140

Thr Ser Leu Met His Ser Pro Asp Tyr Asn Met Lys Leu Val Leu Asp
145                 150                 155                 160

Tyr Ala Pro Asn His Ser Asn Ala Asn Asp Glu Asn Glu Phe Gly Ala
                165                 170                 175

Leu Tyr Arg Asp Gly Val Phe Ile Thr Asp Tyr Pro Thr Asn Val Ala
                180                 185                 190

Ala Asn Thr Gly Trp Tyr His His Asn Gly Gly Val Thr Asn Trp Asn
                195                 200                 205

Asp Phe Phe Gln Val Lys Asn His Asn Leu Phe Asn Leu Ser Asp Leu
210                 215                 220

Asn Gln Ser Asn Thr Asp Val Tyr Gln Tyr Leu Leu Asp Gly Ser Lys
225                 230                 235                 240

Phe Trp Ile Asp Ala Gly Val Asp Ala Ile Arg Ile Asp Ala Ile Lys
                245                 250                 255

His Met Asp Lys Ser Phe Ile Gln Lys Trp Thr Ser Asp Ile Tyr Asp
                260                 265                 270

Tyr Ser Lys Ser Ile Gly Arg Glu Gly Phe Phe Phe Gly Glu Trp
                275                 280                 285

Phe Gly Ala Ser Ala Asn Thr Thr Gly Val Asp Gly Asn Ala Ile
                290                 295                 300

Asp Tyr Ala Asn Thr Ser Gly Ser Ala Leu Leu Asp Phe Gly Phe Arg
305                 310                 315                 320

Asp Thr Leu Glu Arg Val Leu Val Gly Arg Ser Gly Asn Thr Met Lys
                325                 330                 335

Thr Leu Asn Ser Tyr Leu Ile Lys Arg Gln Thr Val Phe Thr Ser Asp
                340                 345                 350
```

```
Asp Trp Gln Val Val Phe Met Asp Asn His Asp Met Ala Arg Ile Gly
            355                 360                 365

Thr Ala Leu Arg Ser Asn Ala Thr Thr Phe Gly Pro Gly Asn Asn Glu
        370                 375                 380

Thr Gly Gly Ser Gln Ser Glu Ala Phe Ala Gln Lys Arg Ile Asp Leu
385                 390                 395                 400

Gly Leu Val Ala Thr Met Thr Val Arg Gly Ile Pro Ala Ile Tyr Tyr
                405                 410                 415

Gly Thr Glu His Tyr Ala Ala Asn Phe Thr Ser Asn Ser Phe Gly Gln
            420                 425                 430

Val Gly Ser Asp Pro Tyr Asn Arg Glu Lys Met Pro Gly Phe Asp Thr
            435                 440                 445

Glu Ser Glu Ala Phe Ser Ile Ile Lys Thr Leu Gly Asp Leu Arg Lys
    450                 455                 460

Ser Ser Pro Ala Ile Gln Asn Gly Thr Tyr Thr Glu Leu Trp Val Asn
465                 470                 475                 480

Asp Asp Ile Leu Val Phe Glu Arg Arg Ser Gly Asn Asp Ile Val Ile
            485                 490                 495

Val Ala Leu Asn Arg Gly Glu Ala Asn Thr Ile Asn Val Lys Asn Ile
            500                 505                 510

Ala Val Pro Asn Gly Val Tyr Pro Ser Leu Ile Gly Asn Asn Ser Val
        515                 520                 525

Ser Val Ala Asn Lys Arg Thr Thr Leu Thr Leu Met Gln Asn Glu Ala
        530                 535                 540

Val Val Ile Arg Ser Gln Ser Asp Asp Ala Glu Asn Pro Thr Val Gln
545                 550                 555                 560

Ser Ile Asn Phe Thr Cys Asn Asn Gly Tyr Thr Ile Ser Gly Gln Ser
                565                 570                 575

Val Tyr Ile Ile Gly Asn Ile Pro Gln Leu Gly Gly Trp Asp Leu Thr
                580                 585                 590

Lys Ala Val Lys Ile Ser Pro Thr Gln Tyr Pro Gln Trp Ser Ala Ser
            595                 600                 605

Leu Glu Leu Pro Ser Asp Leu Asn Val Glu Trp Lys Cys Val Lys Arg
    610                 615                 620

Asn Glu Thr Asn Pro Thr Ala Asn Val Glu Trp Gln Ser Gly Ala Asn
625                 630                 635                 640

Asn Gln Phe Asn Ser Asn Asp Thr Gln Thr Thr Asn Gly Ser Phe
                645                 650                 655
```